US012765908B2

United States Patent
(12) United States Patent
Preissler et al.

(10) Patent No.: US 12,765,908 B2
(45) Date of Patent: *Oct. 20, 2026

(54) SURGICAL SYSTEM HAVING INTERCHANGEABLE TOOL TIPS AND METHODS OF USE THEREOF

(71) Applicant: Symphera GmbH, Munich (DE)

(72) Inventors: Philipp Preissler, Munich (DE); Thomas Wegele, Munich (DE)

(73) Assignee: Symphera GmbH, Munich (DE)

(*) Notice: Subject to any disclaimer, the term of this patent is extended or adjusted under 35 U.S.C. 154(b) by 0 days.

This patent is subject to a terminal disclaimer.

(21) Appl. No.: 19/438,203

(22) Filed: Dec. 31, 2025

(65) Prior Publication Data

US 2026/0123950 A1 May 7, 2026

Related U.S. Application Data

(63) Continuation-in-part of application No. 19/268,369, filed on Jul. 14, 2025, now Pat. No. 12,533,178, (Continued)

(30) Foreign Application Priority Data

Jan. 15, 2024 (EP) .................................... 24151941
Mar. 27, 2024 (EP) .................................... 24167051

(51) Int. Cl.
*A61B 17/295* (2006.01)
*A61B 17/00* (2006.01)
(Continued)

(52) U.S. Cl.
CPC ........ *A61B 17/295* (2013.01); *A61B 17/3201* (2013.01); *A61B 17/50* (2013.01);
(Continued)

(58) Field of Classification Search
CPC ... A61B 17/295; A61B 17/3201; A61B 17/50; A61B 2017/00115; A61B 2017/00199;
(Continued)

(56) References Cited

U.S. PATENT DOCUMENTS 5,755,713 A 5/1998 Bilof et al.
6,053,906 A 4/2000 Honda et al.
(Continued)

FOREIGN PATENT DOCUMENTS

AU 3513197 A 1/1998
AU 2009243488 A1 12/2009
(Continued)

OTHER PUBLICATIONS

Extended EP Search Report dated Aug. 29, 2024 in EP Patent Appl. Serial No. 24167051.2.

(Continued)

*Primary Examiner* — Michael F Peffley
*Assistant Examiner* — Samantha M Good
(74) *Attorney, Agent, or Firm* — Greenberg Traurig, LLP; Christopher C. Bolten; Albert K. Heng

(57) ABSTRACT

Systems and methods for performing surgery are provided, which permit multiple tool tips to be interchanged within an instrument shaft during a minimally invasive procedure. The surgical device holds a plurality of interchangeable tool tips such that a selected tool tip from a chamber of a magazine can be mounted at the distal end of an elongated shaft for a laparoscopic surgery. In this manner, multiple tool types can be interchanged within a shaft without having to remove the instrument from the patient for tool changes, thereby increasing surgical efficiencies and reducing the number of tools needed for a procedure.

30 Claims, 36 Drawing Sheets

Related U.S. Application Data which is a continuation-in-part of application No. PCT/EP2025/050952, filed on Jan. 15, 2025.

(51) Int. Cl.
*A61B 17/3201* (2006.01)
*A61B 17/50* (2006.01)
*A61B 18/00* (2006.01)
*A61B 18/14* (2006.01)

(52) U.S. Cl.
CPC . *A61B 18/1445* (2013.01); *A61B 2017/00115* (2013.01); *A61B 2017/00199* (2013.01); *A61B 2017/00212* (2013.01); *A61B 2017/00398* (2013.01); *A61B 2017/00477* (2013.01); *A61B 2018/00083* (2013.01); *A61B 2018/00595* (2013.01); *A61B 2018/00982* (2013.01); *A61B 2018/146* (2013.01)

(58) Field of Classification Search
CPC ........... A61B 2017/00212; A61B 2017/00398; A61B 2017/00464; A61B 18/1445; A61B 18/1482
See application file for complete search history.

(56) References Cited

U.S. PATENT DOCUMENTS

| | | | |
|---|---|---|---|
| 6,325,808 B1 | 12/2001 | Bernard et al. | |
| 6,770,081 B1 | 8/2004 | Cooper et al. | |
| 7,686,826 B2 | 3/2010 | Lee et al. | |
| 8,317,777 B2 | 11/2012 | Zubiate et al. | |
| 8,992,421 B2 | 3/2015 | Stand et al. | |
| 9,168,050 B1 | 10/2015 | Peine et al. | |
| 9,572,628 B2 | 2/2017 | Zubiate et al. | |
| 9,649,163 B2 | 5/2017 | Darisse et al. | |
| 9,821,477 B2 | 11/2017 | Anderson et al. | |
| 9,869,339 B2 | 1/2018 | Zimmerman et al. | |
| 10,130,361 B2 | 11/2018 | Yates et al. | |
| 10,143,524 B2 | 12/2018 | Koch et al. | |
| 10,206,710 B2 | 2/2019 | Kern et al. | |
| 10,213,268 B2 | 2/2019 | Dachs, II | |
| 10,258,416 B2 | 4/2019 | Mintz et al. | |
| 10,426,471 B2 | 10/2019 | Shelton, IV et al. | |
| 10,543,044 B2 | 1/2020 | Krimsky | |
| 10,591,032 B2 | 3/2020 | Wixey | |
| 10,617,439 B2 | 4/2020 | Deodhar et al. | |
| 10,667,809 B2 | 6/2020 | Bakos et al. | |
| 10,667,810 B2 | 6/2020 | Shelton, IV et al. | |
| 10,682,138 B2 | 6/2020 | Shelton, IV et al. | |
| 10,716,565 B2 | 7/2020 | Shelton, IV et al. | |
| 10,722,314 B2 | 7/2020 | Danitz et al. | |
| 10,729,509 B2 | 8/2020 | Shelton, IV et al. | |
| 10,729,885 B2 | 8/2020 | Hinman et al. | |
| 10,751,081 B2 | 8/2020 | Skubitz et al. | |
| 10,765,427 B2 | 9/2020 | Shelton, IV et al. | |
| 10,772,629 B2 | 9/2020 | Shelton, IV et al. | |
| 10,779,823 B2 | 9/2020 | Shelton, IV et al. | |
| 10,813,713 B2 | 10/2020 | Koch, Jr. et al. | |
| 10,835,245 B2 | 11/2020 | Swayze et al. | |
| 10,835,330 B2 | 11/2020 | Shelton, IV et al. | |
| 10,856,869 B2 | 12/2020 | Shelton, IV et al. | |
| 10,888,322 B2 | 1/2021 | Morgan et al. | |
| 10,933,230 B2 | 3/2021 | Christie et al. | |
| 10,980,952 B2 | 4/2021 | Wixey et al. | |
| 10,993,716 B2 | 5/2021 | Shelton, IV et al. | |
| 11,020,112 B2 | 6/2021 | Shelton, IV et al. | |
| 11,039,835 B2 | 6/2021 | Wixey et al. | |
| 11,039,896 B2 | 6/2021 | Yates et al. | |
| 11,045,270 B2 | 6/2021 | Shelton, IV et al. | |
| 11,076,926 B2 | 8/2021 | Ragosta et al. | |
| 11,134,984 B2 | 10/2021 | Nikolski et al. | |
| 11,213,270 B2 | 1/2022 | Krimsky | |
| 11,246,592 B2 | 2/2022 | Shelton, IV et al. | |
| 11,259,805 B2 | 3/2022 | Shelton, IV et al. | |
| 11,266,405 B2 | 3/2022 | Shelton, IV et al. | |
| 11,284,957 B2 | 3/2022 | Denlinger et al. | |
| 11,324,503 B2 | 5/2022 | Shelton, IV et al. | |
| 11,331,150 B2 | 5/2022 | Jascob et al. | |
| 11,389,184 B2 | 7/2022 | Schwamb et al. | |
| 11,419,481 B2 | 8/2022 | Inoue | |
| 11,419,606 B2 | 8/2022 | Overmyer et al. | |
| 11,424,027 B2 | 8/2022 | Shelton, IV | |
| 11,471,230 B2 | 10/2022 | Nakashima | |
| 11,490,981 B2 | 11/2022 | Denlinger et al. | |
| 11,510,741 B2 | 11/2022 | Shelton, IV et al. | |
| 11,534,252 B2 | 12/2022 | DiMaio et al. | |
| 11,571,210 B2 | 2/2023 | Shelton, IV et al. | |
| 11,576,647 B2 | 2/2023 | Yuasa et al. | |
| 11,638,590 B2 | 5/2023 | Hinman | |
| 11,678,880 B2 | 6/2023 | Shelton, IV et al. | |
| 11,801,098 B2 | 10/2023 | Stokes et al. | |
| 11,849,948 B2 | 12/2023 | Fanelli et al. | |
| 11,911,045 B2 | 2/2024 | Shelton, IV et al. | |
| 11,931,034 B2 | 3/2024 | Posada et al. | |
| 11,998,193 B2 | 6/2024 | Shelton, IV et al. | |
| 12,023,060 B2 | 7/2024 | Traina | |
| 12,097,000 B2 | 9/2024 | Panescu et al. | |
| 12,161,435 B2 | 12/2024 | Abbott et al. | |
| 12,533,178 B2 * | 1/2026 | Preissler | A61B 17/00234 |
| 2002/0042620 A1 | 4/2002 | Julian et al. | |
| 2002/0045905 A1 | 4/2002 | Gerbi et al. | |
| 2002/0120254 A1 | 8/2002 | Julian et al. | |
| 2002/0143319 A1 | 10/2002 | Brock | |
| 2003/0060809 A1 | 3/2003 | Wang et al. | |
| 2003/0065348 A1 | 4/2003 | Hess et al. | |
| 2003/0120272 A1 | 6/2003 | Schneider et al. | |
| 2003/0158541 A1 | 8/2003 | Cuschieri et al. | |
| 2003/0195544 A1 | 10/2003 | Hess et al. | |
| 2004/0054355 A1 | 3/2004 | Gerbi et al. | |
| 2004/0097921 A1 | 5/2004 | Hess et al. | |
| 2005/0215983 A1 | 9/2005 | Brock | |
| 2006/0025677 A1 | 2/2006 | Verard et al. | |
| 2006/0084867 A1 | 4/2006 | Tremblay et al. | |
| 2006/0161136 A1 | 7/2006 | Anderson et al. | |
| 2006/0161138 A1 | 7/2006 | Orban et al. | |
| 2006/0167441 A1 | 7/2006 | Wang et al. | |
| 2006/0235436 A1 | 10/2006 | Anderson et al. | |
| 2007/0060911 A1 | 3/2007 | Webster et al. | |
| 2007/0123855 A1 | 5/2007 | Morley et al. | |
| 2007/0239186 A1 | 10/2007 | Weitzner et al. | |
| 2008/0119870 A1 | 5/2008 | Williams | |
| 2008/0119875 A1 | 5/2008 | Ino et al. | |
| 2008/0215065 A1 | 9/2008 | Wang et al. | |
| 2008/0262596 A1 | 10/2008 | Xiao | |
| 2008/0269562 A1 | 10/2008 | Marescaux et al. | |
| 2008/0287926 A1 | 11/2008 | Abou El Kheir | |
| 2009/0005638 A1 | 1/2009 | Zwolinski | |
| 2009/0036903 A1 | 2/2009 | Ino et al. | |
| 2009/0054733 A1 | 2/2009 | Marescaux et al. | |
| 2009/0292164 A1 | 11/2009 | Yamatani | |
| 2010/0198218 A1 | 8/2010 | Manzo | |
| 2010/0249759 A1 | 9/2010 | Hinman et al. | |
| 2010/0263500 A1 | 10/2010 | Bannasch et al. | |
| 2011/0208007 A1 | 8/2011 | Shohat et al. | |
| 2012/0083826 A1 | 4/2012 | Chao et al. | |
| 2012/0209305 A1 | 8/2012 | Deodhar et al. | |
| 2012/0239010 A1 | 9/2012 | Shelton, IV et al. | |
| 2013/0066313 A1 | 3/2013 | Arts et al. | |
| 2013/0150871 A1 | 6/2013 | Belson et al. | |
| 2013/0211588 A1 | 8/2013 | Diolaiti | |
| 2013/0231681 A1 | 9/2013 | Robinson et al. | |
| 2013/0253499 A1 | 9/2013 | Kimball et al. | |
| 2013/0304063 A1 | 11/2013 | Bacher et al. | |
| 2014/0005662 A1 | 1/2014 | Shelton, IV | |
| 2014/0005676 A1 | 1/2014 | Shelton, IV et al. | |
| 2014/0005680 A1 | 1/2014 | Shelton, IV et al. | |
| 2014/0005718 A1 | 1/2014 | Shelton, IV et al. | |
| 2014/0100567 A1 | 4/2014 | Edwards et al. | |
| 2014/0135795 A1 | 5/2014 | Yanagihara | |
| 2014/0148692 A1 | 5/2014 | Hartmann et al. | |
| 2014/0148817 A1 | 5/2014 | Hasegawa et al. | |
| 2014/0148818 A1 | 5/2014 | Komuro et al. | |

(56) References Cited

U.S. PATENT DOCUMENTS

| | | | | |
|---|---|---|---|---|
| 2014/0166023 | A1 | 6/2014 | Kishi | |
| 2015/0032112 | A1 | 1/2015 | Milburn et al. | |
| 2015/0088191 | A1 | 3/2015 | Coe et al. | |
| 2015/0150633 | A1 | 6/2015 | Castro et al. | |
| 2015/0173841 | A1 | 6/2015 | Orban | |
| 2015/0216515 | A1 | 8/2015 | Newell et al. | |
| 2016/0038004 | A1 | 2/2016 | Tanaka | |
| 2016/0128547 | A1 | 5/2016 | Ogawa et al. | |
| 2016/0158530 | A1 | 6/2016 | Drake et al. | |
| 2016/0184039 | A1 | 6/2016 | Shelton, IV et al. | |
| 2016/0213363 | A1* | 7/2016 | Knight | A61B 90/98 |
| 2016/0331395 | A1 | 11/2016 | Igov | |
| 2017/0100197 | A1 | 4/2017 | Zubiate et al. | |
| 2017/0128146 | A1 | 5/2017 | Iida et al. | |
| 2017/0156745 | A1 | 6/2017 | Okada | |
| 2018/0116691 | A1 | 5/2018 | Reid | |
| 2018/0168615 | A1 | 6/2018 | Shelton, IV et al. | |
| 2018/0228557 | A1 | 8/2018 | Darisse et al. | |
| 2018/0256269 | A1 | 9/2018 | Johnston et al. | |
| 2018/0368844 | A1 | 12/2018 | Bakos et al. | |
| 2019/0000459 | A1 | 1/2019 | Shelton, IV et al. | |
| 2020/0155183 | A1 | 5/2020 | Castro et al. | |
| 2020/0155196 | A1 | 5/2020 | Darisse et al. | |
| 2020/0222117 | A1 | 7/2020 | Zubiate et al. | |
| 2020/0223070 | A1 | 7/2020 | Flaherty et al. | |
| 2020/0352554 | A1 | 11/2020 | Tully et al. | |
| 2020/0352658 | A1 | 11/2020 | Johnson et al. | |
| 2020/0352662 | A1 | 11/2020 | Mampetta et al. | |
| 2021/0212785 | A1 | 7/2021 | Licht et al. | |
| 2021/0338064 | A1 | 11/2021 | Fitterer et al. | |
| 2022/0047287 | A1 | 2/2022 | Stender et al. | |
| 2022/0167964 | A1 | 6/2022 | Meglan et al. | |
| 2022/0218434 | A1 | 7/2022 | Druma | |
| 2023/0020577 | A1 | 1/2023 | Kerver et al. | |
| 2023/0263546 | A1 | 8/2023 | Fujii | |
| 2023/0346421 | A1 | 11/2023 | Vu et al. | |
| 2023/0389982 | A1 | 12/2023 | Willhite et al. | |
| 2024/0023917 | A1 | 1/2024 | Kopel et al. | |
| 2024/0050078 | A1 | 2/2024 | Murdeshwar et al. | |
| 2024/0123197 | A1 | 4/2024 | Wong et al. | |
| 2024/0156554 | A1 | 5/2024 | DiMaio et al. | |
| 2024/0398434 | A1 | 12/2024 | Vu et al. | |
| 2024/0398505 | A1 | 12/2024 | Vu et al. | |
| 2025/0082313 | A1 | 3/2025 | Cohen et al. | |
| 2025/0120742 | A1 | 4/2025 | Huang Shu et al. | |

FOREIGN PATENT DOCUMENTS

| | | | |
|---|---|---|---|
| BR | PI0505527 | A | 9/2006 |
| CH | 11312022 | A | 9/2022 |
| CN | 101027010 | A | 8/2007 |
| CN | 101554335 | A | 10/2009 |
| CN | 102458293 | A | 5/2012 |
| CN | 104042268 | A | 9/2014 |
| CN | 104939882 | A | 9/2015 |
| CN | 105007837 | A | 10/2015 |
| CN | 105193469 | A | 12/2015 |
| CN | 107735225 | A | 2/2018 |
| CN | 110099624 | A | 8/2019 |
| CN | 110114014 | A | 8/2019 |
| CN | 110167464 | A | 8/2019 |
| CN | 111867492 | A | 10/2020 |
| CN | 111989053 | A | 11/2020 |
| DE | 102009025013 | A1 | 12/2010 |
| DE | 102013224754 | A1 | 6/2015 |
| EP | 0051640 | B1 | 10/1986 |
| EP | 0920280 | A1 | 6/1999 |
| EP | 1685802 | A1 | 8/2006 |
| EP | 1813218 | A1 | 8/2007 |
| EP | 2666420 | A1 | 11/2013 |
| EP | 2799020 | A1 | 11/2014 |
| EP | 2866685 | A1 | 5/2015 |
| EP | 3106118 | A1 | 12/2016 |
| EP | 3193760 | A1 | 7/2017 |
| EP | 3420947 | A1 | 1/2019 |
| EP | 4049594 | A1 | 8/2022 |
| ES | 2588536 | T3 | 11/2016 |
| JP | H11137563 | A | 5/1999 |
| JP | 2000023994 | A | 1/2000 |
| JP | 2001057984 | A | 3/2001 |
| JP | 2003305050 | A | 10/2003 |
| JP | 2004000601 | A | 1/2004 |
| JP | 3571414 | B2 | 9/2004 |
| JP | 2005218497 | A | 8/2005 |
| JP | 2006087687 | A | 4/2006 |
| JP | 2006187446 | A | 7/2006 |
| JP | 2007050181 | A | 3/2007 |
| JP | 2007275565 | A | 10/2007 |
| JP | 2009011809 | A | 1/2009 |
| JP | 2009082700 | A | 4/2009 |
| JP | 2013034859 | A | 2/2013 |
| JP | 2015139552 | A | 8/2015 |
| JP | 2015213746 | A | 12/2015 |
| JP | 2016013437 | A | 1/2016 |
| JP | 2016202898 | A | 12/2016 |
| JP | 2017159029 | A | 9/2017 |
| JP | 2017205562 | A | 11/2017 |
| JP | 2019005601 | A | 1/2019 |
| JP | 2019513067 | A | 5/2019 |
| JP | 2019107442 | A | 7/2019 |
| JP | 2020501794 | A | 1/2020 |
| JP | 2020501817 | A | 1/2020 |
| JP | 2020044327 | A | 3/2020 |
| JP | 2020078581 | A | 5/2020 |
| JP | 2020525136 | A | 8/2020 |
| JP | 2020525202 | A | 8/2020 |
| JP | 2021180895 | A | 11/2021 |
| KR | 20080108906 | A | 12/2008 |
| KR | 102009222 | B1 | 8/2019 |
| KR | 102092384 | B1 | 3/2020 |
| KR | 102107720 | B1 | 5/2020 |
| KR | 102115312 | B1 | 5/2020 |
| KR | 102118008 | B1 | 6/2020 |
| KR | 102437404 | B1 | 8/2022 |
| KR | 102688404 | B1 | 7/2024 |
| KR | 20240135866 | A | 9/2024 |
| WO | WO-2002065933 | A2 | 8/2002 |
| WO | WO-2005099605 | A1 | 10/2005 |
| WO | WO-2005107607 | A1 | 11/2005 |
| WO | WO-2006129726 | A1 | 12/2006 |
| WO | WO-2008121234 | A2 | 10/2008 |
| WO | WO-2010150618 | A1 | 12/2010 |
| WO | WO-2015012184 | A1 | 1/2015 |
| WO | WO-2015045431 | A1 | 4/2015 |
| WO | WO-2015046348 | A1 | 4/2015 |
| WO | WO-2015190412 | A1 | 12/2015 |
| WO | WO-2016079788 | A1 | 5/2016 |
| WO | WO-2016151935 | A1 | 9/2016 |
| WO | WO-2017104015 | A1 | 6/2017 |
| WO | WO-2019003031 | A1 | 1/2019 |
| WO | WO-2020035924 | A1 | 2/2020 |
| WO | WO-2020188391 | A1 | 9/2020 |
| WO | WO-2022094345 | A1 | 5/2022 |
| WO | WO-2023133519 | A1 | 7/2023 |
| WO | WO-2023235498 | A1 | 12/2023 |
| WO | WO-2024068924 | A1 | 4/2024 |
| WO | WO-2024097605 | A1 | 5/2024 |
| WO | WO-2024249982 | A1 | 12/2024 |
| WO | WO-2025153571 | A1 | 7/2025 |
| WO | WO-2025153572 | A1 | 7/2025 |
| WO | WO-2025153573 | A1 | 7/2025 |

OTHER PUBLICATIONS

International Search Report & Written Opinion dated Apr. 28, 2025 in Int'l PCT Patent Appl. Serial No. PCT/EP2025/050952.

International Search Report & Written Opinion dated Dec. 13, 2023 in Int'l PCT Patent Appl. Serial No. PCT/EP2023/077049.

* cited by examiner

SURGICAL SYSTEM HAVING INTERCHANGEABLE TOOL TIPS AND METHODS OF USE THEREOF

CROSS-REFERENCE TO RELATED APPLICATIONS

This application is a continuation-in-part application of U.S. patent application Ser. No. 19/268,369, filed Jul. 14, 2025, now U.S. Pat. No. 12,533,178, which is a continuation-in-part application of PCT/EP2025/050952, filed Jan. 15, 2025, which claims priority to European Patent Appl. No. 24167051.2, filed Mar. 27, 2024, and European Patent Appl. No. 24151941.2, filed Jan. 15, 2024, the entire contents of each of which are incorporated herein by reference.

TECHNICAL FIELD

This technology generally relates to devices for performing surgery, such as microinvasive surgical devices having interchangeable tool tips.

BACKGROUND

During a surgical procedure, e.g., laparoscopy, if a different tool tip is to be used, the handheld surgical device inserted within a patient must be removed and a different handheld surgical device having the desired tool tip must be introduced through the incision into the patient's body, resulting in a prolonged time in operation in which the patient may be under anesthesia. In laparoscopic surgeries, a number of different tools are used, which have to be switched an average of 20 to 50 times during the procedure. This can result in distracting workflows for surgeons and a loss of valuable surgical time.

WO 2002/065933 discloses a remotely controllable surgical instrument comprising an instrument shaft having a proximal end drivably intercoupled to a drive unit and a distal end insertable within a subject for performing a medical procedure at an operative site within the subject, a remotely disposed user interface interconnected to a remotely disposed signal processor which processes commands received from the user interface, the signal processor interconnected to the drive unit for transmitting processed command signals received from the user interface to the drive unit characterized in that the instrument shaft comprises an elongated disposable shaft removably interconnected to the drive unit via a coupling mechanism and a distal instrument drivable via cables.

U.S. 2007/0239186 discloses a method of performing a medical procedure (e.g., a cardiac bypass procedure) on a patient. The method comprises introducing at least one medical instrument into a patient (e.g., percutaneously), conveying control signals from a remote controller to a drive unit, and operating the drive unit in accordance with the control signals to actuate at least one tool respectively located on the medical instrument(s) to transversely secure a first anatomical vessel (e.g., a blood vessel) to a sidewall of a second anatomical vessel (e.g., another blood vessel). In one method, the control signals are conveyed from the remote controller to the drive unit in response to user commands. The user commands may be movements made at a user interface that correspond to movements of the medical instrument(s).

While the prior art approaches may be satisfactory in some regards, they have certain shortcomings and disadvantages.

In view of the foregoing drawbacks of previously known systems and methods, there exists a need for an improved surgical devices and method for use thereof.

For example, there exists a need for surgical devices that allow for improved efficiency of surgery and methods for use of the devices.

Additionally, there exists a need for surgical devices that enable more flexible usage of operating tools and method for using the devices.

SUMMARY

Provided herein are improved systems and methods for performing microinvasive surgery. In accordance with one aspect, a surgical device is provided. The surgical device may comprise a body portion, an elongated shaft having a proximal end coupled to the body portion, a distal end, and a lumen extending therebetween, and a magazine coupled to the body portion and comprising a plurality of chambers, each chamber configured to receive an interchangeable tool tip therein. The magazine may be configured to be selectively actuated to align a selected chamber of the plurality of chambers with the proximal end of the elongated shaft. The surgical device further may comprise a tool activation mechanism comprising a distal region configured to be releasably coupled to the interchangeable tool tip of the selected chamber. The tool activation mechanism may be configured to transition between a retracted configuration within the body portion where the distal region is disposed proximal to the selected chamber, and an extended configuration where the distal region is coupled to the interchangeable tool tip of the selected chamber and extends through the lumen of the elongated shaft such that the interchangeable tool tip is mounted at the distal end of the elongated shaft.

The tool activation mechanism may be substantially rigid against compression and elongation and flexible against bending as the tool activation mechanism transitions from the extended configuration to the retracted configuration. For example, the tool activation mechanism may comprise a rack, and an actuation rod disposed within a lumen of the rack. The rack and the actuation rod may be configured to move together as the tool activation mechanism transitions between the retracted configuration and the extended configuration. In some embodiments, the rack may comprise a plurality of joint-connected rack elements. Moreover, the rack may be configured to substantially bend about a single bend axis. A distal end of the rack may be configured to releasably engage a proximal portion of the interchangeable tool tip, and a distal end of the actuation rod may comprise a coupling element configured to be releasably coupled to an engagement portion of the interchangeable tool tip. In addition, when the coupling element is coupled to the engagement portion, the actuation rod may be configured to be actuated to move axially relative to the rack to thereby actuate the interchangeable tool tip. For example, the interchangeable tool tip may comprise a tool configured to be actuated in an open and close degree of freedom, such that actuation of the actuation rod may actuate the interchangeable tool tip in the open and close degree of freedom.

In addition, the body portion may comprise an actuation bar configured to be releasably coupled to a proximal coupling element of the actuation rod in the extended configuration. The actuation bar may be configured to be actuated to move the actuation rod axially relative to the rack. Further, the body portion may be sized and shaped to be held in a user's palm, and the body portion may comprise an interface operatively coupled to the actuation bar, the interface configured to be actuated by the user to actuate the actuation bar and move the actuation rod axially relative to the rack. Moreover, the rack may comprise a geared outer surface, and the body portion may further comprise a worm gear operatively coupled to a pinion gear operatively coupled to the geared outer surface, the worm gear configured to be actuated to cause rotation of the pinion gear to thereby cause translational movement of the rack via a geared connection between the pinion gear and the geared outer surface.

Each chamber of the plurality of chambers of the magazine may be sized and shaped to prevent proximal movement of the interchangeable tool tip beyond a proximal end of the chamber. Moreover, one or more chambers of the plurality of chambers of the magazine may comprise a geometry configured to receive the interchangeable tool tip in a predetermined aligned manner. For example, the geometry may be configured to prevent rotation of the interchangeable tool tip relative to the chamber. In addition, the body portion may comprise a receptacle sized and shaped to slidably receive the tool activation mechanism in the retracted configuration. For example, the receptacle may be configured to permit the tool activation mechanism to substantially bend about a bend axis as the tool activation mechanism transitions from the extended configuration to the retracted configuration. The bend axis may be substantially orthogonal to a longitudinal axis of the elongated shaft. In some embodiments, the elongated shaft may be configured to transmit electric power from a generator to the interchangeable tool tip mounted at the distal end of the elongated shaft. Accordingly, the interchangeable tool tip may comprise a tool configured for electric cauterization.

The surgical device further may comprise one or more motors operatively coupled to the magazine, the one or more motors configured to be actuated to move the magazine relative to the body portion. Moreover, the surgical device may comprise a user interface operatively coupled to the one or more motors, the user interface configured to receive user input indicative of the selected chamber. Accordingly, the one or more motors may be configured to actuate the magazine to align the selected chamber with the proximal end of the elongated shaft based on the user input. Additionally, the surgical device may comprise an actuator configured to rotate the elongated shaft and the interchangeable tool tip mounted thereon relative to the body portion. The distal end of the elongated shaft may be configured to prevent rotation of the interchangeable tool tip relative to the elongated shaft. For example, the actuator may comprise a rotatable knob disposed on the body portion.

Moreover, the surgical device may comprise a handle at the proximal end of the elongated shaft, the handle configured to be held by the user for performing surgery. In some embodiments, the surgical device may be configured for use with a surgical robot system. Additionally, the surgical device may be configured to be operatively coupled to a display that displays various types of interchangeable tool tips within the plurality of chambers, such that a user may be permitted to select a type of interchangeable tool tip using the display. The interchangeable tool tips within the plurality of chambers may comprise at least one of a hook, a grasper, or scissors. In some embodiments, the magazine may be rotatably coupled to the body portion, and the plurality of chambers may be equally radially disposed about a longitudinal axis of the magazine.

In accordance with some aspects, a method for performing a surgical procedure is provided. The method may comprise positioning a first tool tip of a plurality of interchangeable tool tips at a distal end of an elongated shaft of a surgical device for performing a first type of surgical task, the first tool tip releasably coupled to a distal region of a tool activation mechanism; receiving, via a user interface, user input indicative of a second tool tip of the plurality of interchangeable tool tips for performing a second type of surgical task, the second tool tip disposed within a magazine comprising a plurality of chambers and positioned at a proximal end of the elongated shaft, each chamber of the plurality of chambers configured to receive an interchangeable tool tip therein; retracting the first tool tip into a first chamber of the plurality of chambers using the tool activation mechanism; selectively actuating, via at least one motor operatively coupled to the magazine, the magazine to align a second chamber of the plurality of chambers with the proximal end of the elongated shaft based on the user input, the second chamber having the second tool tip therein; and transitioning the tool activation mechanism between a retracted configuration where the distal region of the tool activation mechanism is disposed proximal to the second chamber and an extended configuration where the distal region is releasably coupled to the second tool tip and advanced such that the second tool tip is mounted at the distal end of the elongated shaft for performing the second type of surgical task.

The surgical device may comprise a body portion coupled to the proximal end of the elongated shaft, and the magazine may be coupled to the body portion. Moreover, the plurality of chambers may be equally radially disposed about a longitudinal axis of the magazine, such that selectively actuating the magazine may comprise rotating the magazine relative to the body portion about the longitudinal axis. Further, transitioning the tool activation mechanism to the retracted configuration may comprise receiving the tool activation mechanism within a receptacle of the body portion. For example, receiving the tool activation mechanism within the receptacle of the body portion may comprise substantially bending the tool activation mechanism about a bend axis, the bend axis substantially orthogonal to a longitudinal axis of the elongated shaft.

In addition, the method further may comprise actuating an actuator to rotate the elongated shaft and the second tool tip mounted thereon relative to the body portion. The distal end of the elongated shaft may be configured to prevent rotation of the second tool tip relative to the elongated shaft. For example, the actuator may comprise a rotatable knob disposed on the body portion, such that actuating the actuator may comprise rotating the knob to rotate the elongated shaft and the second tool tip mounted thereon relative to the body portion. Moreover, the tool activation mechanism may be substantially rigid against compression and elongation and flexible against bending as the tool activation mechanism transitions between retracted the configuration and the extended configuration. Additionally, selectively actuating the magazine may comprise selectively actuating the magazine via a first motor of the at least one motor, and transitioning the tool activation mechanism between the retracted configuration and the extended configuration may comprise actuating the tool activation mechanism via a second motor of the at least one motor.

The tool activation mechanism may comprise a rack and an actuation rod disposed within a lumen of the rack, such that transitioning the tool activation mechanism between the retracted configuration and the extended configuration may comprise moving the rack and the actuation rod together. For example, the rack may comprise a plurality of joint-connected rack elements. Accordingly, releasably coupling the distal region of the tool activation mechanism to the second tool tip may comprise releasably engaging a distal end of the rack with a proximal portion of the second tool tip and releasably coupling a coupling element at a distal end of the actuation rod to an engagement portion of the second tool tip. The method further may comprise moving the actuation rod axially relative to the rack when the coupling element is coupled to the engagement portion to thereby actuate the second tool tip. For example, moving the actuation rod axially relative to the rack may comprise actuating, in the extended configuration, an actuation bar releasably coupled to a proximal coupling element of the actuation rod. Further, actuating the actuation bar may comprise actuating an interface of the surgical device to move the actuation rod axially relative to the rack. In some embodiments, moving the rack may comprise substantially bending the rack about a single bend axis. Additionally, or alternatively, moving the rack may comprise actuating a worm gear to cause rotation of a pinion gear operatively coupled to a geared outer surface of the rack to thereby cause translational movement of the rack via a geared connection between the pinion gear and the geared outer surface.

Moreover, transitioning the tool activation mechanism between the retracted configuration and the extended configuration may comprise advancing the tool activation mechanism through a lumen of the elongated shaft. Additionally, transitioning the tool activation mechanism between the retracted configuration and the extended configuration to retract the first tool tip into the first chamber and to mount the second tool tip at the distal end of the elongated shaft may occur while the distal end of the elongated shaft remains inserted in a patient via a trocar port. The method further may comprise receiving an interchangeable tool tip of the plurality of interchangeable tool tips within a chamber of the plurality of chambers. Proximal movement of the interchangeable tool tip may be prevented beyond a proximal end of the chamber. In addition, the method may comprise receiving an interchangeable tool tip of the plurality of interchangeable tool tips within a chamber of the plurality of chambers in a predetermined aligned manner. For example, the predetermined aligned manner may prevent rotation of the interchangeable tool tip relative to the chamber. Moreover, the method may comprise actuating, when an interchangeable tool tip of the plurality of interchangeable tool tips is mounted at the distal end of the elongated shaft, the interchangeable tool tip in an open and close degree of freedom. The method further may comprise transmitting, when an interchangeable tool tip of the plurality of interchangeable tool tips is mounted at the distal end of the elongated shaft, electric power from a generator to the interchangeable tool tip. Accordingly, the method further may comprise performing electric cauterization via the interchangeable tool tip.

In addition, the surgical device may comprise a handle at the proximal end of the elongated shaft, the handle configured to be held by a user for performing surgery. The method further may comprise using the surgical device with a surgical robot system for performing robot-assisted surgery. In addition, the method may comprise displaying, via a display, various types of interchangeable tool tips within the plurality of chambers. Moreover, the display may display a selection of a type of interchangeable tool tip based on the user input. For example, displaying various types of interchangeable tool tips within the plurality of chambers may comprise displaying, via the display, at least one of a hook, a grasper, or scissors. In some embodiments, the first tool tip may comprise a hook or a grasper and the second tool tip may comprise scissors.

DETAILED DESCRIPTION

Embodiments of this technology are directed to exemplary systems and methods for performing surgical procedures, particularly via a surgical device configured to change tool tips while the operating end of the surgical device remains within the patient's body. As used herein, the term "distal" may refer to a side of the surgical device facing a patient, e.g., when a tool tip mounted to the surgical device and/or the elongated shaft of the surgical device is inserted into a body of the patient, and/or a direction towards this side. The term "proximal" may refer to a side of the surgical device opposite to a side facing the patient and/or to a corresponding direction. The term "user interface" refers to any interface enabling user interaction with the system, including but not limited to displays, physical input elements, voice interfaces, gesture-based inputs, and combinations thereof.

Figure 1:
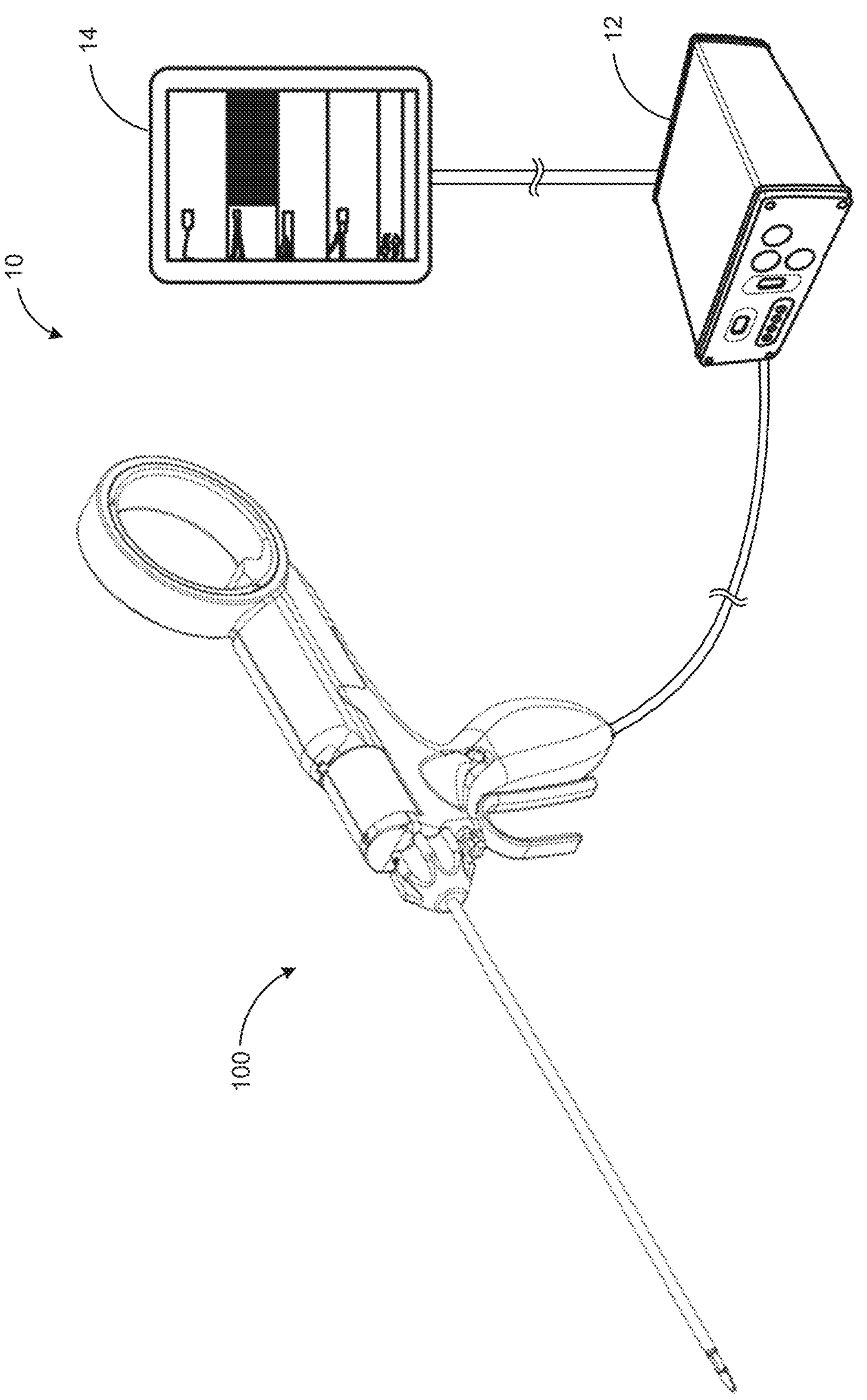
FIG. 1 illustrates an exemplary system for performing microinvasive surgery in accordance with some embodiments.

Referring now to FIG. 1, an exemplary system for performing surgery is provided. System 10 may include surgical device 100 configured for performing surgical procedures, controller 12 operatively coupled to surgical device 100, and user interface 14 having a display configured to display a plurality of interchangeable tool tips to facilitate selection of a desired tool tip for use with surgical device 100 by a user. Selection of the desired tool tip may be based on user input (e.g., touch, movement, audio, etc.) received at the user interface. For example, selection of the desired tool tip may be provided by the user via actuation of one or more actuators of surgical device 100, e.g., actuator 113*b*, as described in further detail below with regard to FIG. 3A. Alternatively, or additionally, in some embodiments, user interface 14 may comprise a graphical user interface configured to receive user input indicative of the desired tool tip selection via the graphical user interface as an actuator, and/or controller 12 may be configured to receive user input indicative of the desired tool tip selection via voice command.

Controller 12 may be configured to generate and store data to keep track of which interchangeable tool tips have been selected by the user during a surgical procedure, as well as the sequence/order in which the tool tips are selected during the surgical procedure. Accordingly, in some embodiments, controller 12 may be programmed to suggest a next interchangeable tool tip for a given surgical procedure based on the stored data. For example, controller 12 may be programmed to execute an artificial intelligence technique, e.g., machine learning algorithm, to identify the current surgical phase of the surgical procedure, e.g., via pattern recognition techniques based on the known type of surgical procedure, the current selected tool tip, and/or the sequence of tool tip selections, and to suggest the next interchangeable tool tip based on the identified current surgical phase of the surgical procedure, e.g., via the display of user interface 14. The user may select whether or not to accept the tool tip suggestion.

In some embodiments, controller 12 may be operatively coupled to a visualization system to thereby receive image data, e.g., endoscopic video feed, of the surgical site as an input, and may be programmed to suggest the next interchangeable tool tip for the given surgical procedure based on the endoscopic video feed. For example, controller 12 may be programmed to execute an image segmentation technique to identify, e.g., the surgical procedure, the current surgical phase of the surgical procedure, and/or the selected tool tip, based on the received image data. In addition, controller 12 may be operatively coupled to a power generator for providing electrosurgical power to surgical device 100 to operate surgical device 100 and/or the selected tool tip mounted thereto, e.g., when the selected tool tip is configured for electric cauterization, as described in further detail below.

Figure 2A:
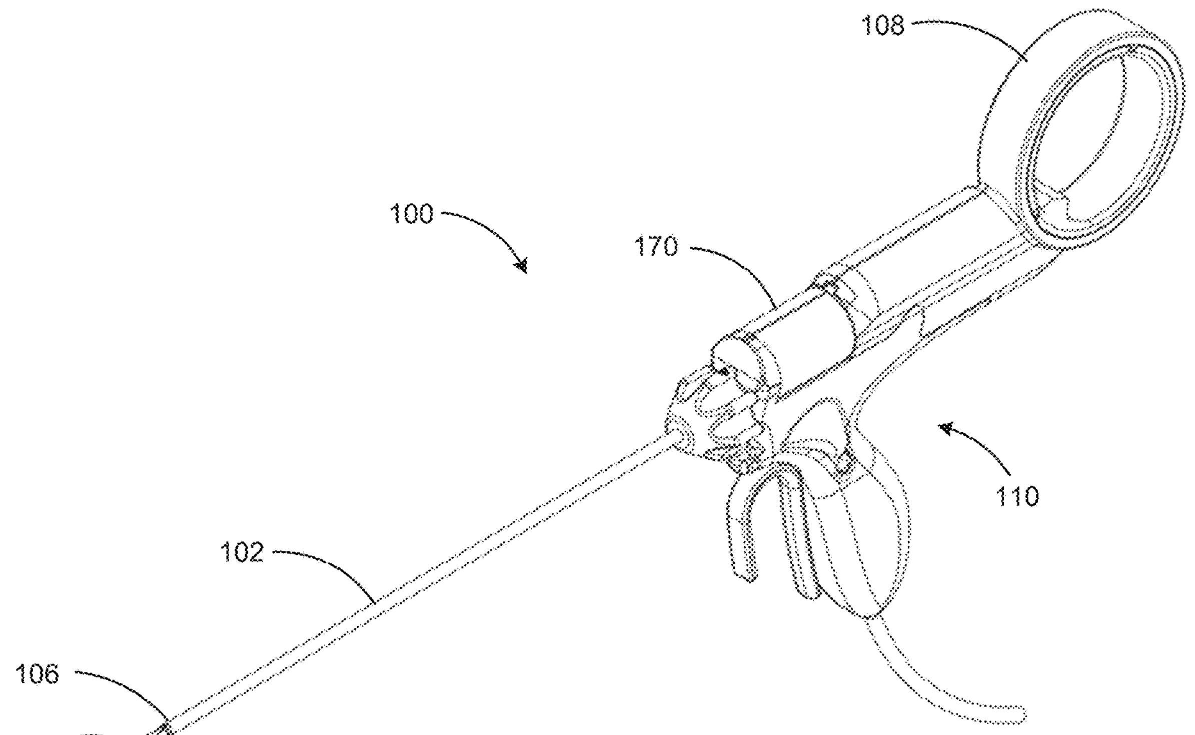
FIG. 2A illustrates an exemplary surgical device of the system of FIG. 1.
Figure 2B:
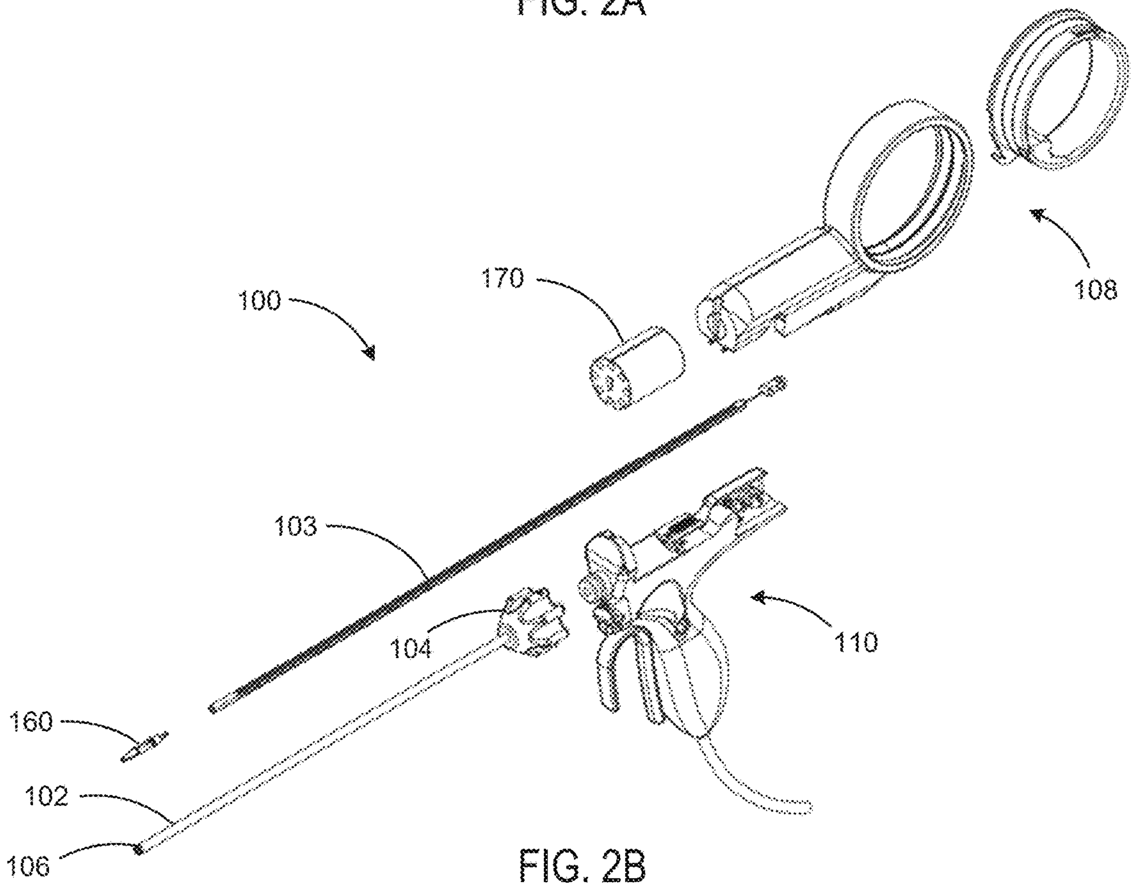
FIG. 2B is an exploded view of the surgical device of FIG. 2A.
Figure 2C:
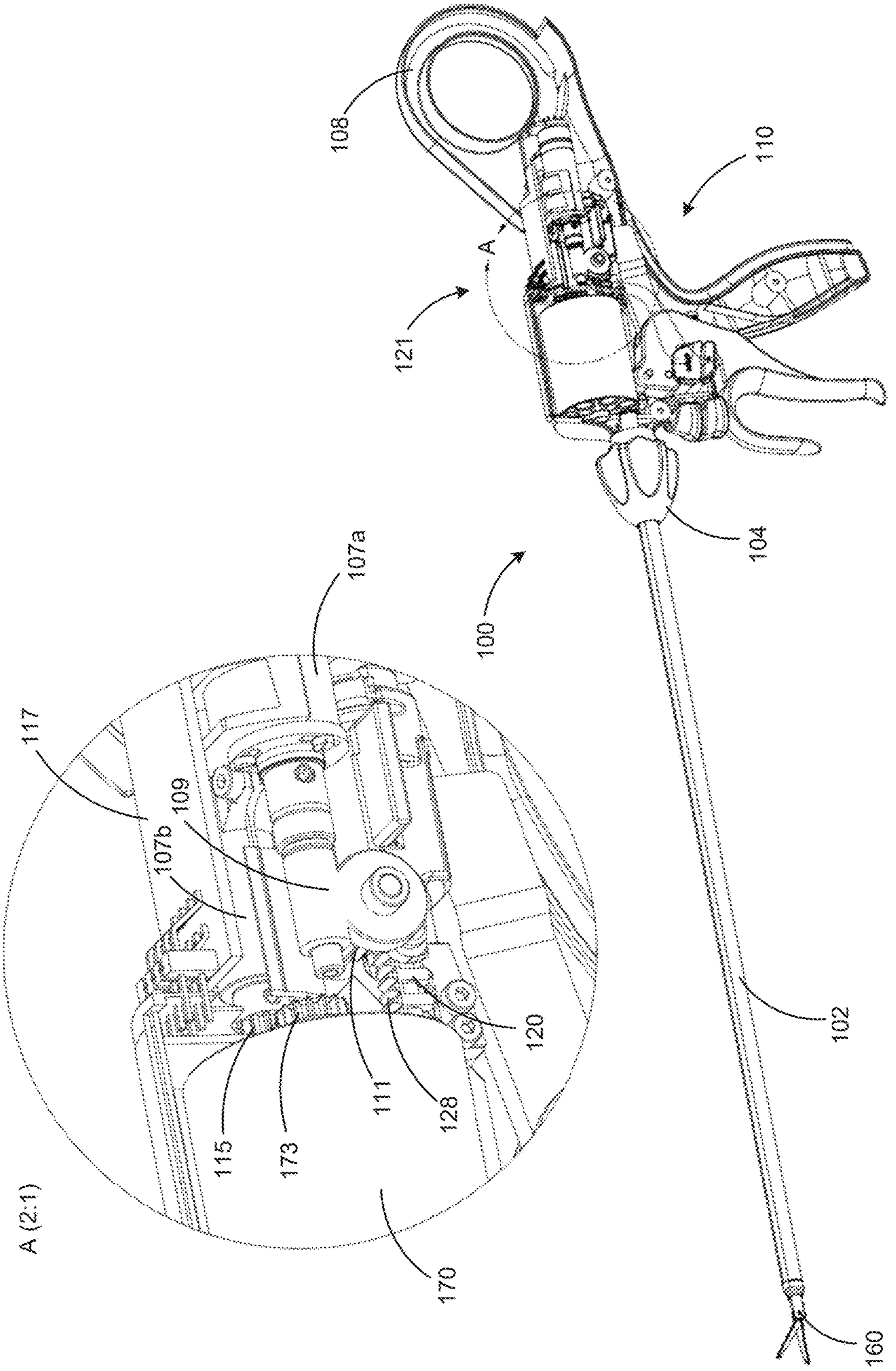
FIG. 2C illustrates exemplary components of a rack drive and a magazine drive of an exemplary surgical device.

Referring now to FIGS. 2A to 2C, an exemplary surgical device for performing microinvasive surgical procedures including, for example, laparoscopy, is provided. Surgical device 100 may be a handheld surgical device configured for introducing a selected tool tip, e.g., tool tip 160 configured for microinvasive surgery, into a body, e.g., of a human, or in another example, into a body of an animal. One or more of the interchangeable tool tips may be configured for different surgical tasks, such as cutting, grasping, hooking, or electric cauterization, as described in further detail below with regard to FIG. 13, etc. Surgical device 100 may include body portion 110, which may be sized and shaped to be held in a user's palm and/or integrated into a surgical robot system, elongated shaft 102 having a proximal end coupled to body portion 110, distal end 106, and a lumen extending therebetween forming an internal channel, and magazine 170 comprising a plurality of chambers, e.g., tool receiving locations, each chamber sized and shaped to removably receive an interchangeable tool tip, e.g., tool tip 160, therein. As will be understood by a person having ordinary skill in the art, the chambers of magazine 170 may comprise any structure, e.g., fully or partially enclosed, configured to receive an interchangeable tool tip therein.

Accordingly, magazine 170 may be configured to hold multiple interchangeable tool tips simultaneously. Magazine 170 may be selectively actuated to align a desired chamber with the lumen of elongated shaft 102, such that a desired tool tip within the desired chamber may be advanced from magazine 170, e.g., via tool activation mechanism 103, and interchangeably mounted to distal end 106 of elongated shaft 102, e.g., in a mounted configuration, as described in further detail below. Accordingly, elongated shaft 102, particularly distal end 106 of elongated shaft 102, may be configured for insertion into the patient's body, allowing distal end 106 to reach a point of surgery remote from an incision through which the tool is introduced. Unlike other commercially available handheld surgical devices where, if a different tool tip is to be used, the handheld surgical device inserted within a patient must be removed and a different handheld surgical device having the desired tool tip must be introduced through the incision into the patient's body, resulting in a prolonged time in operation in which the patient may be under anesthesia, handheld surgical device 100 may be configured to change the tool tip mounted at distal end 106 of elongated shaft 102 while distal end 106 is located inside the patient's body, e.g., in a surgery configuration, without removing and reinserting the surgical device into the patient's body.

As shown in FIG. 2B, an exploded view of surgical device 100, surgical device 100 may include tool activation mechanism 103 slidably disposed therein and transitionable between a retracted configuration within body portion 110, e.g., within receptacle 108 of body portion 110, and an extended configuration to thereby mount the selected tool tip 160 to distal end 106 of elongated shaft 102. For example, in the retracted configuration, at least the proximal portion of tool activation mechanism 103 may be in a rolled configuration within receptacle 108, such that the distal end of tool activation mechanism 103 is disposed proximal to magazine 170, e.g., proximal to the select chamber of magazine 170 that is aligned with the lumen of elongated shaft 102. Accordingly, receptacle 108 may be configured to store rack 120 in a spirally or circularly bent shape. Moreover, surgical device 100 may include a track sized and shaped to slidably receive tool activation mechanism 103 therein, the track including the lumen of elongated shaft 102 and extending through receptacle 108 such that tool activation mechanism 103 may move between the retracted configuration within receptacle 108 and the extended configuration within the lumen of elongated shaft 102.

Thus, tool activation mechanism 103 may be configured to bend about a bend axis, e.g., the central axis of receptacle 108 orthogonal to the longitudinal axis of the track of surgical device 100, as tool activation mechanism 103 transitions to the retracted configuration. The bend axis and the longitudinal axis of track 101 within body portion 100 may be spaced apart from each other, e.g., by a distance substantially identical to a bending radius of the proximal section of tool activation mechanism 103 received in receptacle 108. In other words, a longitudinal axis of track 101 may be substantially identical to a tangent of tool activation mechanism 103 when rolled in receptacle 108. Advantageously, bending of tool activation mechanism 103 may be reduced, e.g., compared to receptacles comprising a bending axis that intersect with the longitudinal axis of track 101. When transitioning from the retracted configuration to the extended configuration, the distal end of tool activation mechanism 103 may engage with the tool tip disposed within the chamber of magazine 170 that is aligned with the track of surgical device 100, and advance the tool tip from magazine 170 and through the lumen of elongated shaft 102 for mounting at distal end 106 of elongated shaft 102. Accordingly, tool activation mechanism 103 may be configured to transfer tension and compression forces to tool tip 160.

As shown in FIG. 2C, surgical device 100 may include rack drive 121 disposed on body portion 110, and configured to be actuated to move tool activation mechanism 103 between the retracted and extended positions. Rack drive 121 may comprise a rack-drive-motor and a rack-drive-transmission. For example, rack drive 121 may include one or more motors, e.g., motor 107*a*, operatively coupled to worm drive 109 having pinion gear 111, which may be operatively coupled to tool activation mechanism 103, e.g., via a geared connection, such that actuation of motor 107*a* causes worm drive 109 to rotate pinion gear 111, which causes translational movement of tool activation mechanism 103, as described in further detail below. Rack drive 121 may be self-locking, e.g., not back-drivable. In other words, if the rack-drive-motor does not apply a torque to a motor-side of the rack-drive-transmission, a force applied to rack 120 may not result in a movement of the rack-drive-transmission, e.g., rack drive 121 inhibits movement of rack 120 apart from deformation of rack 120 due to external forces. Accordingly, tool tip 160 may be held in a safe manner when mounted to distal end 106 of elongated shaft 102, providing for reliable mounting of the tool tip. In addition, worm drive 109 may comprise a self-locking worm-gear unit, thereby allowing for a compact and simple solution without requiring additional parts for locking rack drive 121. Accordingly, rack drive 121 may remain locked in case of an interruption of electrical power, thus providing for a defined position of tool 160 and increased safety in case of an electrical fault. Additionally, or alternatively, the rack-drive-transmission may comprise an automatic locking mechanism. For example, the rack-drive-transmission may comprise a pin for locking the transmission when motor 107*a* does not drive rack 120. In some embodiments, motor 107*a* may apply a holding torque, e.g., by means of a position control activated once tool tip 160 is mounted to distal end 106 of elongated shaft 102.

Moreover, surgical device 100 may comprise a magazine drive configured to be actuated to selectively rotate magazine 170 to a select angular position relative to body portion 110, to thereby align the select chamber of magazine 170 with the track of surgical device 100, and accordingly, the lumen of elongated shaft 102, as described above. The magazine drive may comprise, for example, a stepper motor, and/or a BLDC-motor with a position sensor, such as a hall sensor, and an appropriate position control, such as a PID-control, as well as a gear stage, such as a planetary gear. For example, as shown in FIG. 2C, the magazine drive may include one or more motors, e.g., motor 107*b*, operatively coupled to a switchable gear, e.g., drive gear 115, which may be operatively coupled to driven gear 173 of magazine 170, e.g., via a geared connection to connect motor 107*b* and magazine 170, such that actuation of motor 107*b* causes rotation of drive gear 115, which causes rotation of driven gear 173, and accordingly, magazine 170 relative to body portion 110.

In addition, the magazine drive may comprise one or more sensors configured for sensing a position of magazine 170, such as an angular position and/or a translational position of magazine 170. For example, in case of the rotatable magazine 170, the sensor may be configured for sensing the angular position of magazine 170, and in case of magazine 170 configured to be moved along the translation axis, the sensor may be configured for sensing a translational position of magazine 170. The one or more sensors configured for sensing the position of magazine 170 may comprise at least one of an incremental encoder or a reference sensor, such as reference switch, e.g., a proximity sensor. Alternatively, the one or more sensors may comprise an absolute encoder. Alternatively, in some embodiments, the one or more sensors may comprise a simple switch configured to be triggered every time the angular position of magazine 170 is such that a chamber of magazine 170 is aligned with the track of surgical device 100.

As shown in FIG. 2C, the proximal end of elongated shaft 102 may be coupled to body portion 110, and may comprise actuator 104, e.g., an orientating formation, configured to, upon actuation, rotate elongated shaft 102, and accordingly tool tip 160 mounted to distal end 106 of elongated shaft 102, about its longitudinal axis relative to body portion 110.

For example, actuator 104 may be a knob fixedly coupled to elongated shaft 102, and rotatably coupled to body portion 110, such that a user may actuate actuator 104 by rotating actuator 104 relative to body portion 110.

Figure 3A:
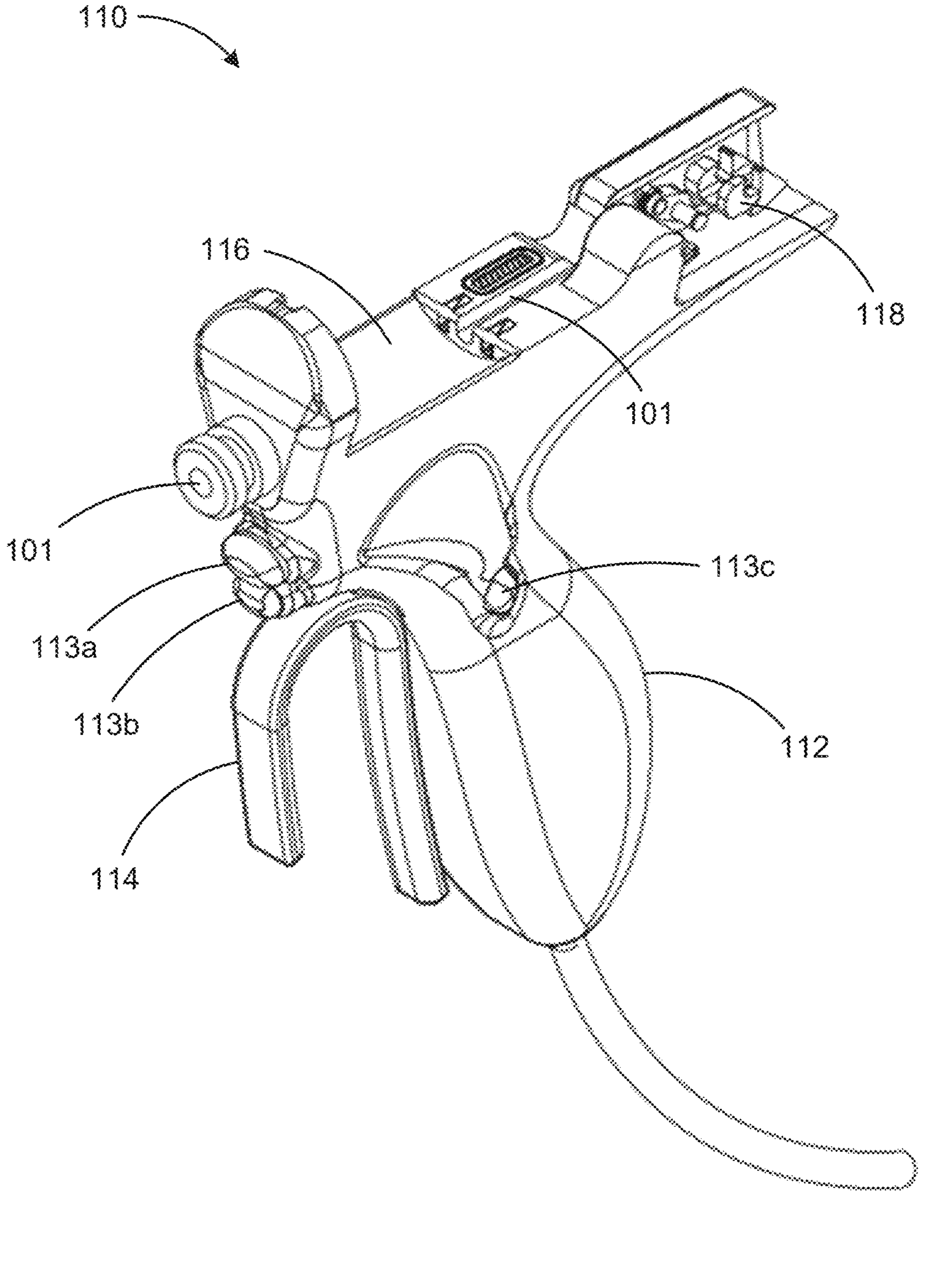
FIG. 3A illustrates an exemplary body portion of the surgical device of FIGS. 2A and 2B constructed in accordance with some embodiments.

FIG. 3A illustrates body portion 110, with magazine 170, drive rack 121, and receptacle 108 omitted for clarity. As shown in FIG. 3A, body portion 110 may include handle portion 112 sized and shaped to be held by a user's palm, and a connection cable configured to electrically couple surgical device 100 to a control unit, e.g., controller 12, as shown in FIG. 1, to thereby provide electrical power to surgical device 100. As shown in FIG. 3A, body portion 110 may include frame 116 sized and shaped to rotatably receive magazine 170 therein, and disposed proximal to elongated shaft 102, such that magazine 170 is in communication with the proximal portion of elongated shaft 102. In addition, the track of surgical device 100, e.g., track 101, may extend through body portion 110, such that the longitudinal axis of track 101 may be aligned with the longitudinal axis of the selected chamber of magazine 170.

Moreover, body portion 110 may include one or more actuators configured to be actuated by the user to control one or more functions of surgical device 100. For example, body portion 110 may include actuator 113*a*, which may be actuated to apply electrical energy to the select tool tip, e.g., when tool tip 160 comprises an electrical tool tip, as described in further detail below. In some embodiments, actuator 113*a* may comprise two distinct actuators, for example, a first actuator configured to be actuated to apply electrical energy with normal frequency, e.g., to coagulate tissue with normally bipolar energy via a bipolar grasper tool tip, and a second actuator configured to be actuated to apply electrical energy with high frequency, e.g., to cut through tissue with normally monopolar energy via a monopolar L-hook tool tip.

In addition, body portion 110 may include actuator 113*b*, which may be actuated to select the desired tool tip from a plurality of available tool tips. For example, the plurality of available tool tips may be displayed via display 14, such that actuation of actuator 113*b* permits the user to select the desired tool tip displayed on display 14. Body portion 110 further may include safety actuator 113*c*, which may be required to be actuated, e.g., continuously pressed, during the tool selection process to avoid accidental tool selection. For example, actuator 113*c* may be required to be actuated in order to permit actuation of actuator 113*b*. As shown in FIG. 3A, body portion 110 further may include actuator 114, e.g., an operating lever, configured to be manually actuated by the user to actuate tool activation mechanism 103 to thereby actuate the tool tip mounted at distal end 106 of elongated shaft 102. For example, actuator 114 may be operatively coupled to actuation bar end piece 118, which may be configured to releasably engage tool activation mechanism 103 when the select tool tip is mounted at distal end 106 of elongated shaft 102 via tool activation mechanism 103, such that actuation of actuator 114 causes actuation of tool activation mechanism 103, as described in further detail below. For example, actuation bar end piece 118 may be configured to releasably engage the proximal coupling element of the rod of tool activation mechanism 103, e.g., coupling element 132 of rod 130, as described in further detail below with regard to FIG. 4C.

Figure 3B:
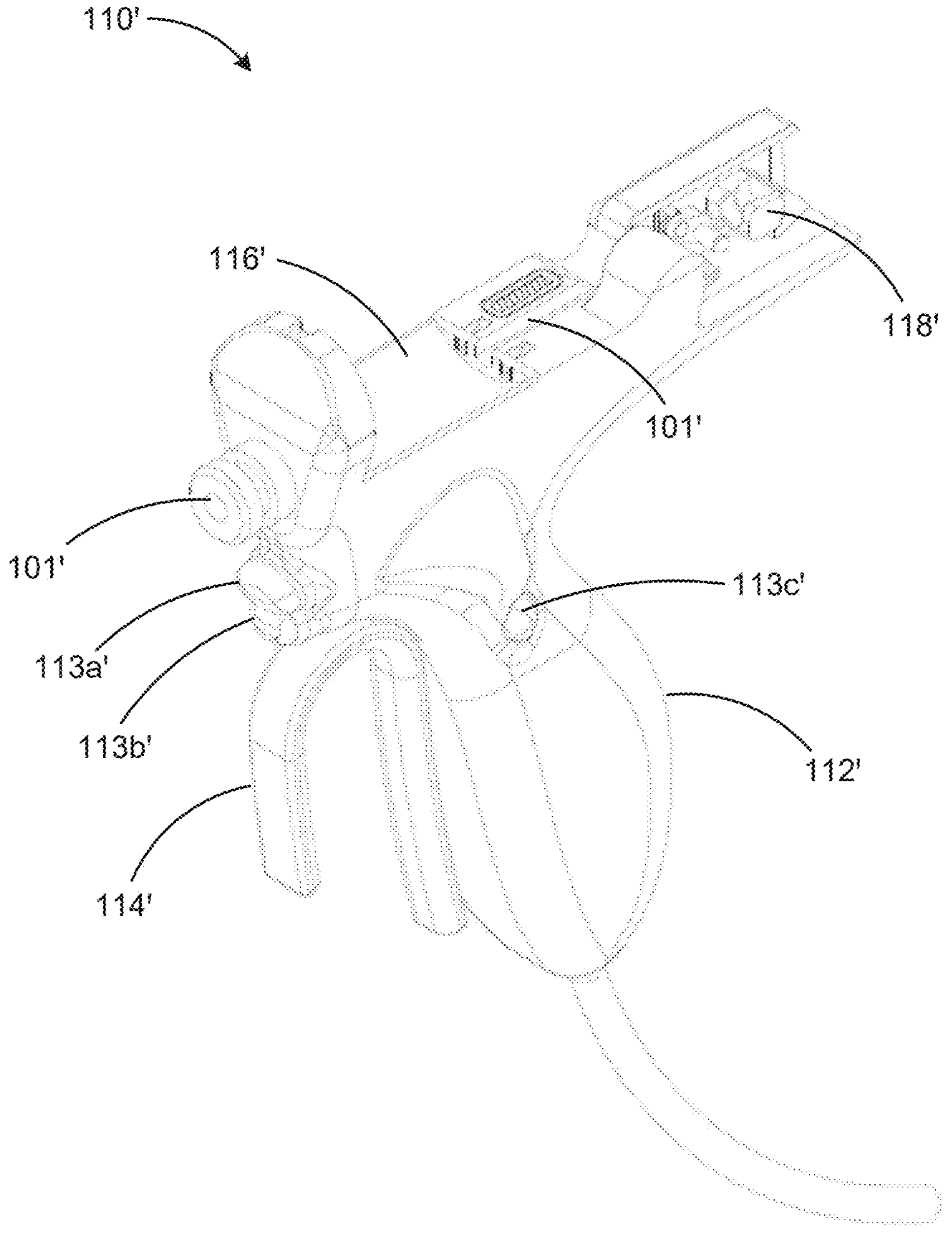
FIG. 3B illustrates an alternative exemplary body portion of the surgical device constructed in accordance with some embodiments.

As described in further detail below with regard to FIG. 4D, the coupling element of the rod of the tool activation mechanism may comprise different shaped profiles for releasable engagement with the actuation bar end piece of the body portion of the surgical device. Accordingly, the actuation bar end piece may have a corresponding geometry for releasably engaging with the coupling element of the rod, as shown in FIG. 3B. Body portion 110' may be constructed similar to body portion 110, with similar components having like prime reference numerals. For example, track 101', handle portion 112', actuators 113*a*'-113*c*', operative lever 114', and frame 116' correspond with track 101, handle portion 112, actuators 113*a*-113*c*, operative lever 114, and frame 116 of body portion 110. Body portion 110' differs from body portion 110 in that actuation bar end piece 118' comprises a geometry configured to releasably engage with coupling element 132' of rod 130', as described in further detail below with regard to FIG. 4D.

Alternatively, in some embodiments, surgical device 100 may be configured to be robotically operated, e.g., via a linear drive and/or an excentre, for robot-assisted surgery, as described in EP 24167051, the entire contents of which is incorporated herein by reference.

Figure 4A:
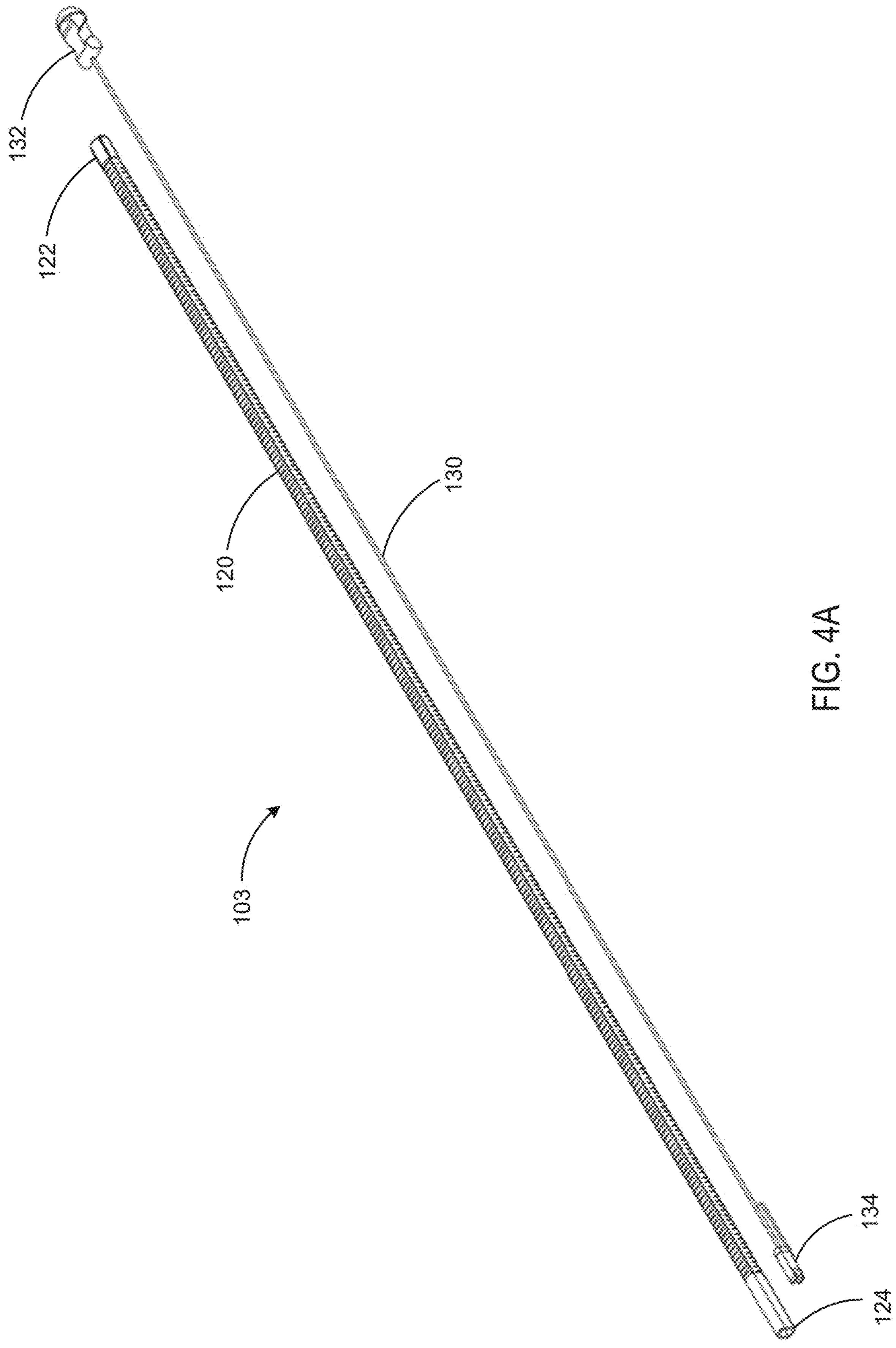
FIG. 4A illustrates an exemplary tool activation mechanism comprising a rack and rod in accordance with some embodiments.

Referring now to FIG. 4A, an exemplary tool activation mechanism 103 is provided. As shown in FIG. 4A, tool activation mechanism 103 may comprise rack 120 having proximal end 122, distal end 124 configured to releasably engage with a proximal end of tool tip 160, and a lumen extending therebetween, the lumen sized and shaped to slidably receive rod 130 therein. Rack 120 is configured to move the select tool tip from the chamber of magazine 170 that is aligned with track 101 of surgical device 100 along the longitudinal axis of elongated shaft 102 to distal end 106 of elongated shaft 102, as well as from distal end 106 back to the chamber of magazine 170. Accordingly, rack 120 is configured to transmit compressive forces to tool tip 160. Rack 120 may be configured such that rack 120 is substantially rigid against compression. For example, in an unbiased configuration of rack 120, adjacent windings of the metal wire may be in contact with each other, thus providing for an increased stiffness against compression of rack 120.

In some embodiments, rack 120 may comprise a stiffness against compression of, e.g., at least 300 N/mm, at least 600 N/mm, or at least 1000 N/mm. Moreover, rack 120 may be configured such that rack 120 is flexible against bending, e.g., rack 120 may have a sufficiently low stiffness against bending such that it may be bendable about the bend axis of receptacle 108. In other words, rack 120 may be configured for transmitting compressive forces and may tolerate being bent about at least one bend axis. Preferably, rack 120 may only bend about a single bend axis. For example, in some embodiments, rack 120 may comprise a stiffness against bending of at most 600 $N/mm^2$, at most 500 $N/mm^2$, or preferably at most 470 $N/mm^2$. Thus, rolled storage of rack 120 and rod 130 within receptacle 108 is enabled, e.g. storage with a bending radius of at most 60 mm, at most 50 mm, or at most 40 mm. In some embodiments, the track extending through receptacle 108 may comprise a spiral configuration such that in the retracted configuration, tool activation mechanism 103 may be spirally wounded within receptacle 108. Accordingly, when spirally wounded, rack 120 may only substantially bend about a single bend axis as the spirally configuration is not aligned in a single plane.

Rod 130 may be configured to transmit tensile and compressive forces to tool tip 160, to thereby mechanically actuate a multi-part tool tip 160, as described in further detail below. As shown in FIG. 4A, the proximal end of rod 130 may comprise a proximal coupling element 132 configured to releasably engage with actuation bar end piece 118, and distal coupling element 134 configured to be releasably coupled to a base of tool tip 160. Rod 130 may be substantially rigid in tension and compression, and flexible against bending. For example, rod 130 may be a push-pull cable, a metal rod, e.g., a steel cable comprising a steel filament. In some embodiments, rod 130 may be formed by a plurality of pieces operatively coupled together.

Figure 4B:
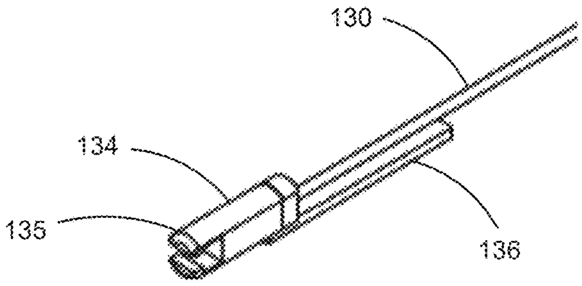
FIG. 4B illustrates the distal portion of the exemplary rod of the tool activation mechanism of FIG. 4A.

As shown in FIG. 4B, distal coupling element 134 may comprise a claw, e.g., one or more fingers 135, configured to releasably engage the base of tool tip 160. For example, fingers 135 may define a cavity sized and shaped to releasably receive the base of tool tip 160 therein. As shown in FIG. 4B, the cavity defined by fingers 135 may be open on its lateral sides to thereby permit the base of tool tip 160 to enter the cavity from the side, e.g., as magazine 170 is rotated relative to distal coupling element 134, as described in further detail below. For example, the cavity defined by fingers 135 may have a smaller width at its distal end compared with the middle and/or proximal portion of the cavity, the middle and/or proximal portion of the cavity having a geometry that corresponds with the base of tool tip 160. Alternatively, in some embodiments, distal coupling element 134 may be coupled to the base of tool tip 160 via, e.g., a magnetic connection. In some embodiments, e.g., when the selected tool tip is configured for electric cauterization as described in further detail below, distal coupling element 134 further may include sliding member 136. For example, sliding member 136 may be formed of a non-conductive material, and configured to facilitate transmission of one pole line for electrosurgical energy through the rod by isolating rod 130 and distal coupling element 134 from the inner wall of elongated shaft 102.

Figure 4C:
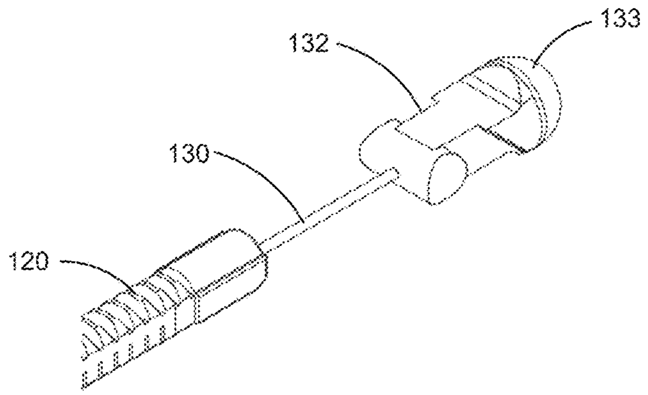
FIG. 4C illustrates the proximal portion of the exemplary rod of the tool activation mechanism of FIG. 4A.
Figure 4D:
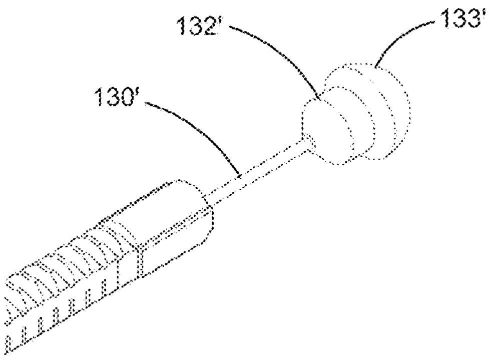
FIG. 4D illustrates the proximal portion of an alternative exemplary rod constructed in accordance with some embodiments.
Figure 4E:
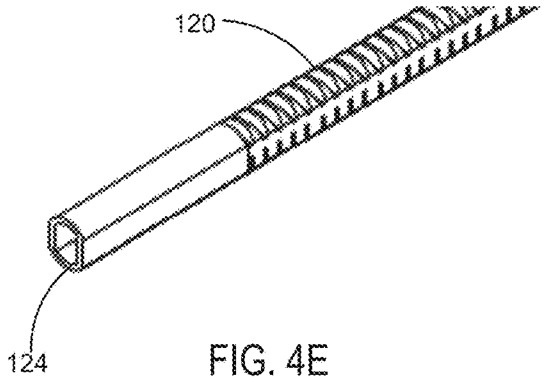
FIG. 4E illustrates the distal portion of the exemplary rack of the tool activation mechanism of FIG. 4A.
Figure 4F:
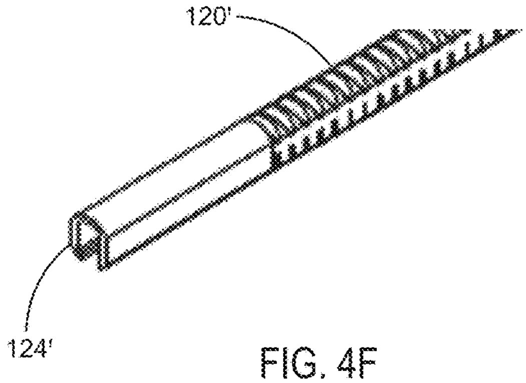
FIG. 4F illustrates the distal portion of an alternative exemplary rack constructed in accordance with some embodiments.

As shown in FIG. 4C, proximal coupling element 132 may be sized and shaped to facilitate a locking engagement between proximal coupling element 132 and actuation bar end piece 118. Moreover, proximal coupling element 132 may comprise a dome shaped section 133 configured to facilitate insertion into receptacle 108. Alternatively, in some embodiments, the proximal coupling element of the rod may comprise a rotationally symmetrical profile, e.g., symmetrical about a longitudinal axis of the rod, as shown in FIG. 4D. For example, rod 130' may be constructed similar to rod 130, except that proximal coupling element 132' having dome shaped section 133' of rod 130' comprises a rotationally symmetrical profile. Accordingly, proximal coupling element 132' of rod 130' may be configured to releasably engage with actuation bar end piece 118' of body portion 110' of FIG. 3B, as described above. As will be understood by a person having ordinary skill in the art, the proximal coupling element of the rod may have a configuration other than those illustrated in FIGS. 4C and 4D, and the actuation bar end piece of the body portion of the surgical device may have a corresponding geometry to releasably engage with the proximal coupling element. As shown in FIG. 4E, distal end 124 of rack 120 may comprise an enclosed profile. Alternatively, in some embodiments, the distal end of the rack may comprise a U-shaped or C-shaped profile, as shown in FIG. 4F. For example, rack 120' may be constructed similar to rack 120, except that distal end 124' of rack 120' comprises a U-shaped profile.

Figures 5A, 5B, 5C, 5D:
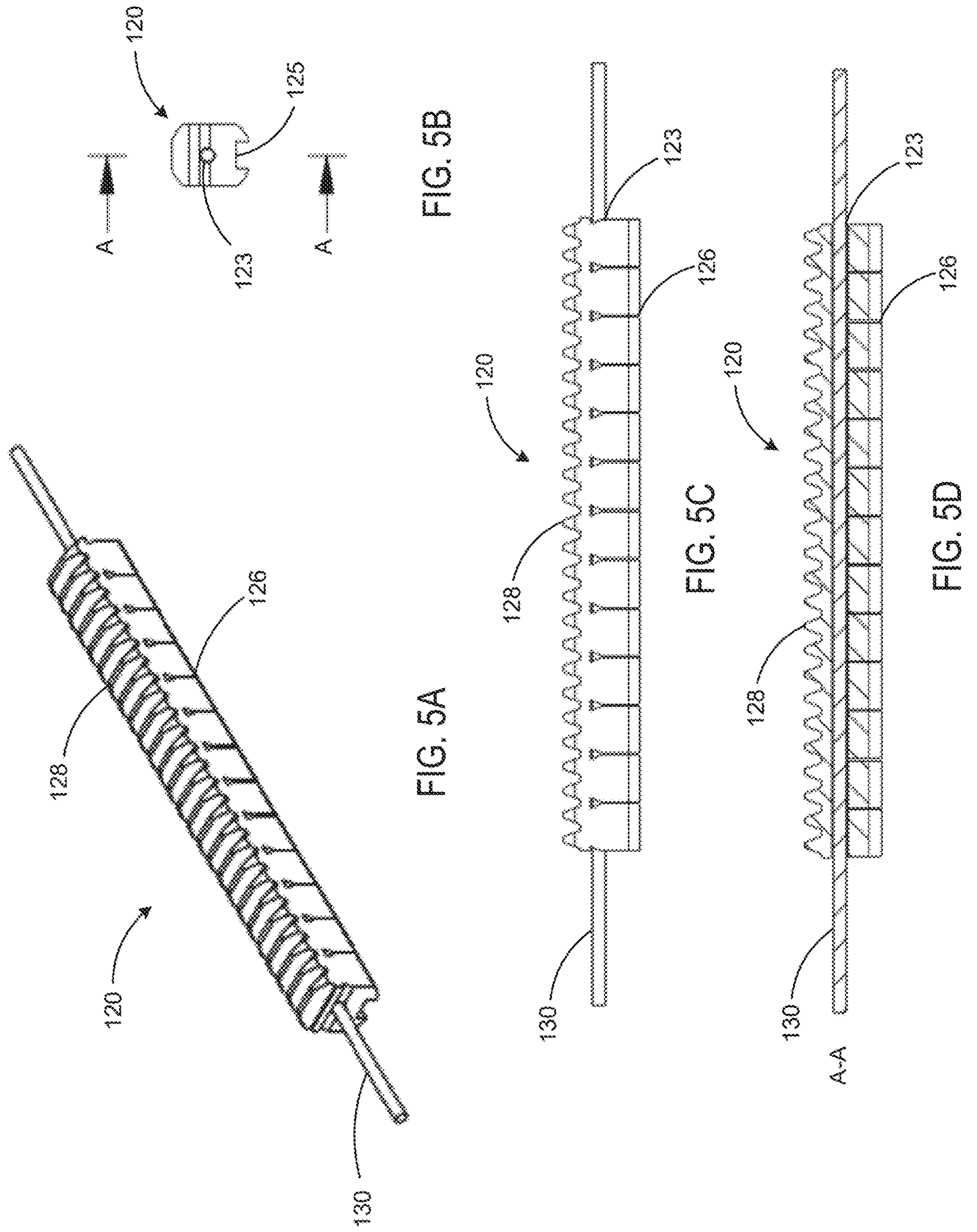
FIGS. 5A to 5D illustrate an exemplary rack constructed in accordance with some embodiments.
Figures 6A, 6B, 6C, 6D:
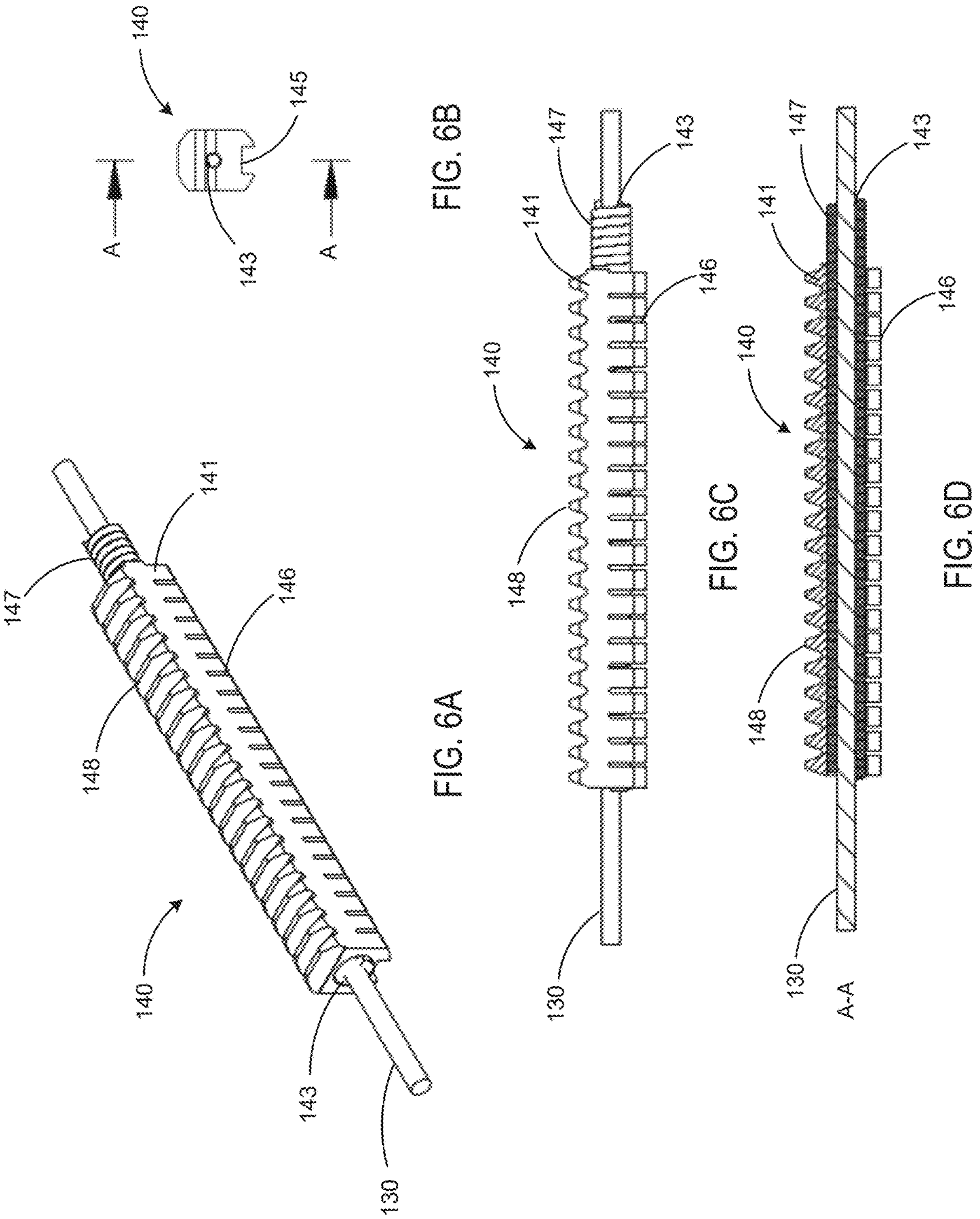
FIGS. 6A to 6D illustrates an alternative exemplary rack comprising an inner metal portion and an outer polymer layer in accordance with some embodiments.
Figure 7B:
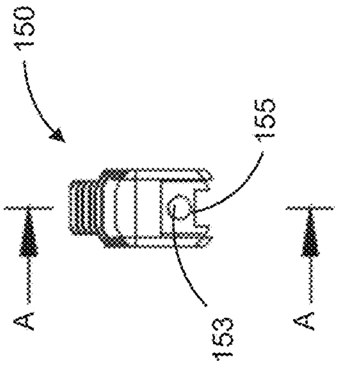
FIGS. 7A to 7D illustrates another alternative exemplary rack comprising a plurality of joint-connected rack elements in accordance with some embodiments.
Figure 7A:
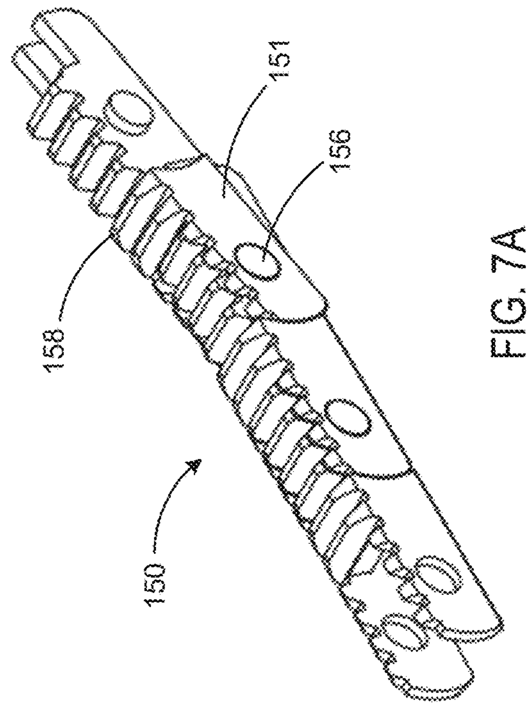
Figure 7C:
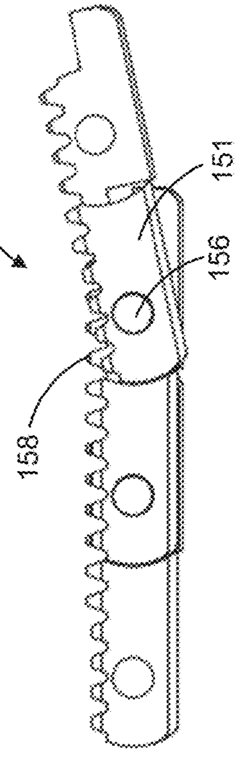
Figure 7D:
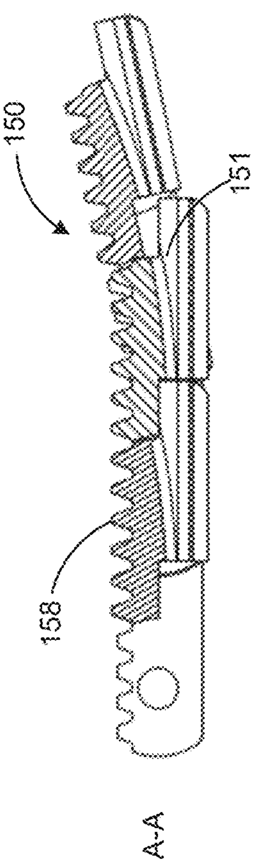

Referring now to FIGS. 5A to 5D, an exemplary body of rack 120 is provided. As shown in FIG. 5B, rack 120 may include lumen 123 extending therethrough and sized and shaped to slidably receive rod 130 therethrough. In addition, the lower surface of rack 120 may include track 125 sized and shaped to facilitate movement of rack 120 through track 101 of surgical device 100, e.g., when at least a portion of track 101 comprises a rail sized and shaped to slidably receive track 125. Moreover, rack 120 may be a gear rack. For example, as shown in FIGS. 5A, 5C, and 5D, the upper surface of the body of rack 120, e.g., the middle region of rack 120 between proximal end 122 and distal end 124, may comprise a linear gear section, e.g., geared surface 128 sized and shaped to be operatively coupled to pinion gear 111, e.g., via a geared connection, as described above. For example, geared surface 128 may comprise a plurality of teeth disposed along the upper surface of rack 120. Accordingly, actuation of worm gear 109 via motor 107*a* causes rotation of pinion gear 111, which causes translational movement of rack 120 via the geared connection between geared surface 128 and pinion gear 111. In addition, the lower portion of rack 120 opposite geared surface 128 may comprise a plurality of slits 126 configured to improve flexibility of rack 120 and facilitate bending of rack 120 about a bend axis, which may be orthogonal to the longitudinal axis of lumen 123 of rack 120. For example, upon bending of rack 120, the upper surface of rack 120 may form a concave shape, while the lower surface of rack 120 may form a convex shape, e.g., via opening of slits 126.

Referring now to FIGS. 6A to 6D, an alternative exemplary rack is provided. Rack 140 may be constructed similar to rack 120. For example, rack 140 may comprise lumen 143 sized and shaped to slidably receive rod 130 therethrough, track 145, geared upper surface 148, and plurality of slits 146, which correspond with lumen 123, track 125, geared upper surface 128, and plurality of slits 126 of rack 120. Rack 140 differs from rack 120 in that rack 140 may be formed of inner metal portion 147, e.g., a wound metal wire, such as a steel spring, and outer polymer layer 141, e.g., form of polypropylene. Accordingly, outer polymer layer 141 may define track 145, geared upper surface 148, and plurality of slits 146, and inner metal portion 147 may define lumen 145.

Referring now to FIGS. 7A to 7D, another alternative exemplary rack is provided. Articulated rack 150 may be constructed similar to rack 120. For example, articulated rack 150 may comprise lumen 153 sized and shaped to slidably receive rod 130 therethrough, track 155, and geared upper surface 158, which correspond with lumen 123, track 125, and geared upper surface 128 of rack 120. Articulated rack 150 differs from rack 120 in that instead of a plurality slits disposed along the lower portion, articulated rack 150 may be formed of a plurality of rack elements 151 connected to one another via a plurality of joints or bolts, e.g., joints 156. Each rack element 151 may provide at least one rotational degree of freedom about the corresponding joint 156. Accordingly, articulated rack 150 may bend about its bend axis via plurality of joints 156. For example, plurality of rack elements 151 may be connected to one another via plurality of joints 156 in a manner such that articulated rack 150 may only bend about a single bend axis and only in a single direction.

Figure 8:
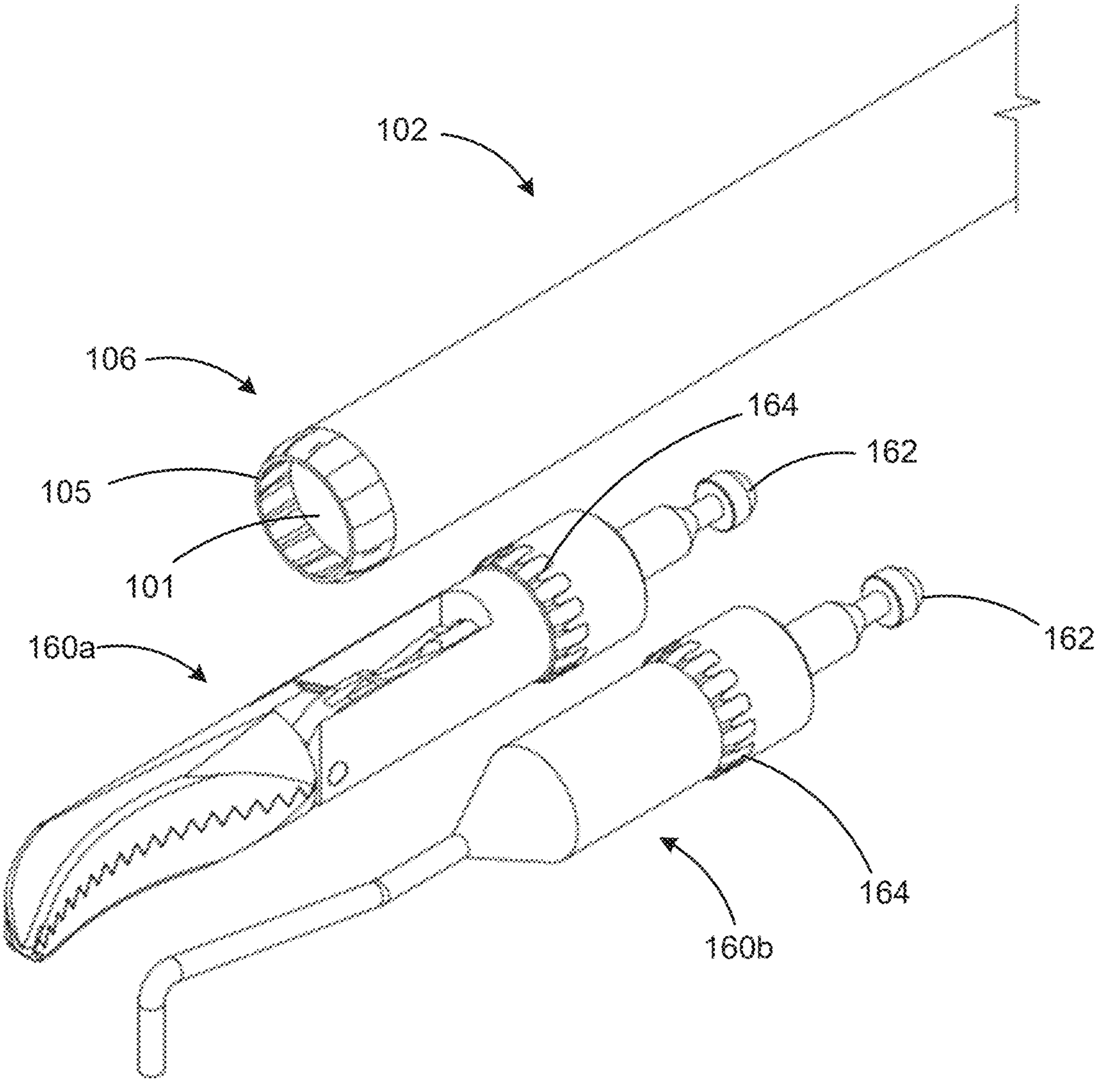
FIG. 8 illustrates the distal end of the surgical device and various interchangeable tool tips.

Referring now to FIG. 8, exemplary tool tips are provided. As shown in FIG. 8, distal end 106 of elongated shaft 102 of surgical device 100 may comprise tool rotating structure 105 configured to mate with the select tool tip 160 in a manner such that tool tip 160 cannot rotate relative to elongated shaft 102 when tool tip 160 is mounted thereto, e.g., via a positive form-fitting connection. For example, tool rotating structure 105 may comprise a plurality of indentations disposed along an inner surface of elongated shaft 102 at distal end 106. Accordingly, as shown in FIG. 8, each tool tip, e.g., grasper tool tip 160*a* and hook tool tip 160*b*, includes proximal portion 164 having a corresponding geometry configured to mate with tool rotating structure 105 at distal end 106 of elongated shaft 102 in a manner such that rotary movement of tool tip 160 relative to elongated shaft 102 is inhibited when tool tip 160 is mounted thereto. For example, the outer surface of proximal portion 164 may comprise a plurality of indentations, e.g., inverted indentations, that correspond with the plurality of indentations of tool rotating structure 105. Accordingly, as described above, actuation of actuator 104 at the proximal end of elongated shaft 102 causes rotation of elongated shaft 102, and accordingly tool tip 160 mounted thereto, relative to body portion 110.

In addition, each tool tip further may include base 162 sized and shaped to be releasably coupled to coupling element 134 of rod 130, e.g., inserted into the cavity defined by fingers 135 of rod 130, as described above. Base 162 may be rotationally symmetrical, e.g., symmetrical about a longitudinal axis of tool tip 160. For example, base 162 may comprise a mushroom shape, e.g., a bulbous portion extending from the proximal portion of the tool top via an elongated portion having an outer diameter that is less than the outer diameter of the bulbous portion. As described above, the cavity defined by fingers 135 of rod 135 may have a smaller width at its distal end compared with its middle and/or proximal portions, and may be open at the lateral sides of coupling element 134. Moreover, when tool activation mechanism 103 is in its fully retracted position, coupling element 134 of rod 130 may be positioned relative to magazine 170 such that the distal end of the cavity defined by fingers 135 is aligned with the elongated portion of base 162 and the bulbous portion of base 162 is aligned with the middle and/or proximal portions of the cavity. Accordingly, as magazine 170 rotates about its longitudinal axis to align the chamber holding the selected tool tip therein with track 101, and accordingly tool activation mechanism 103, the base of the non-selected tool tips disposed within the chambers of magazine 170 between track 101 and the chamber holding the selected tool tip may pass laterally through the cavity defined by fingers 135 until the base of the selected tool tip is disposed within the cavity, e.g., when the chamber holding the selected tool tip is aligned with tool activation mechanism 103. Further, when base 162 is disposed within the cavity of coupling element 134 and both base 162 and coupling element 134 are advanced through the lumen of elongated shaft 102, the inner wall of the lumen of elongated shaft 102 may be sized and shaped to prevent disengagement of base 162 from coupling element 134.

Figure 11A:
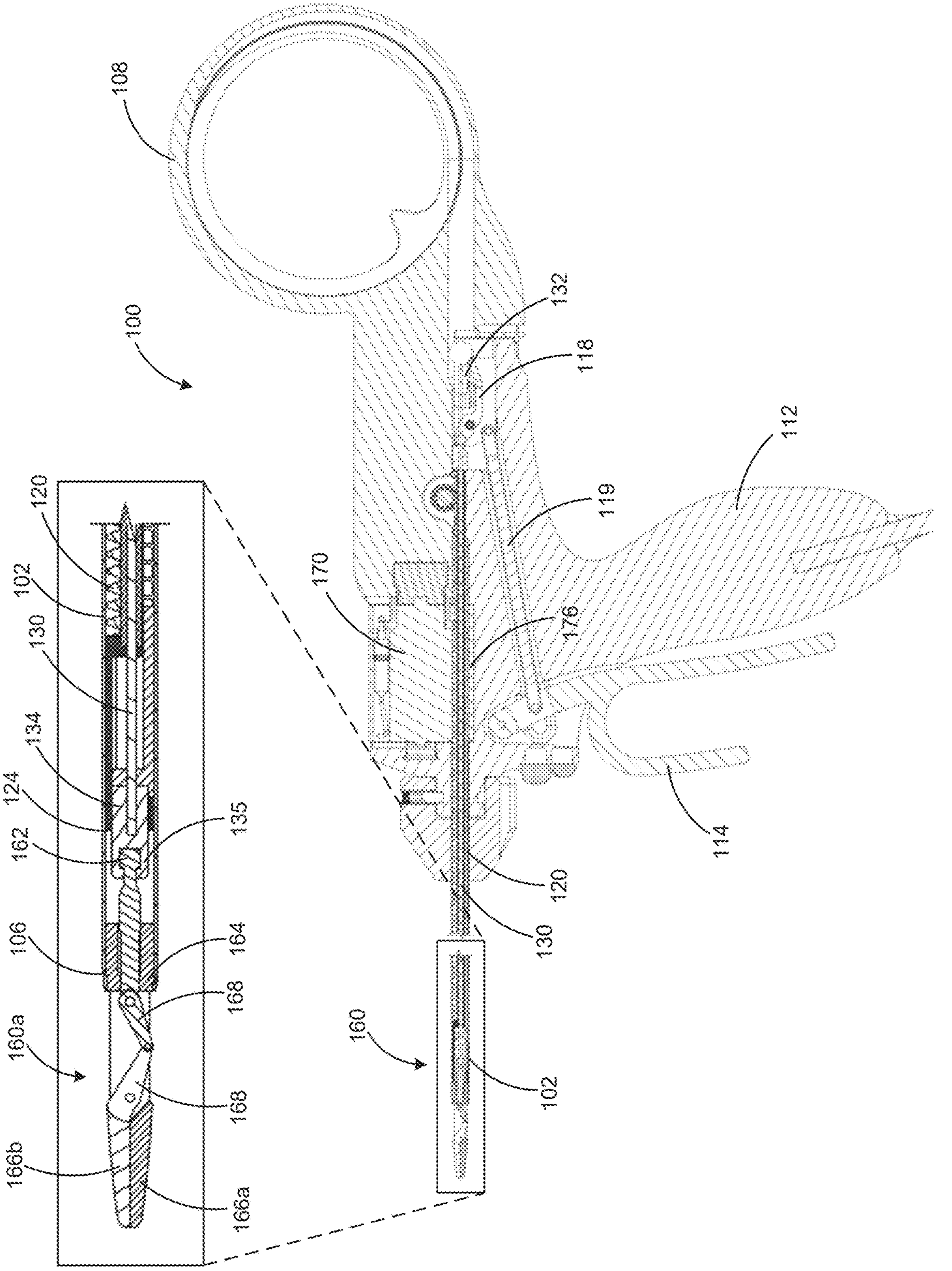
FIGS. 11A and 11B illustrate actuation of the tool activation mechanism of the surgical device in accordance with some embodiments.
Figure 11B:
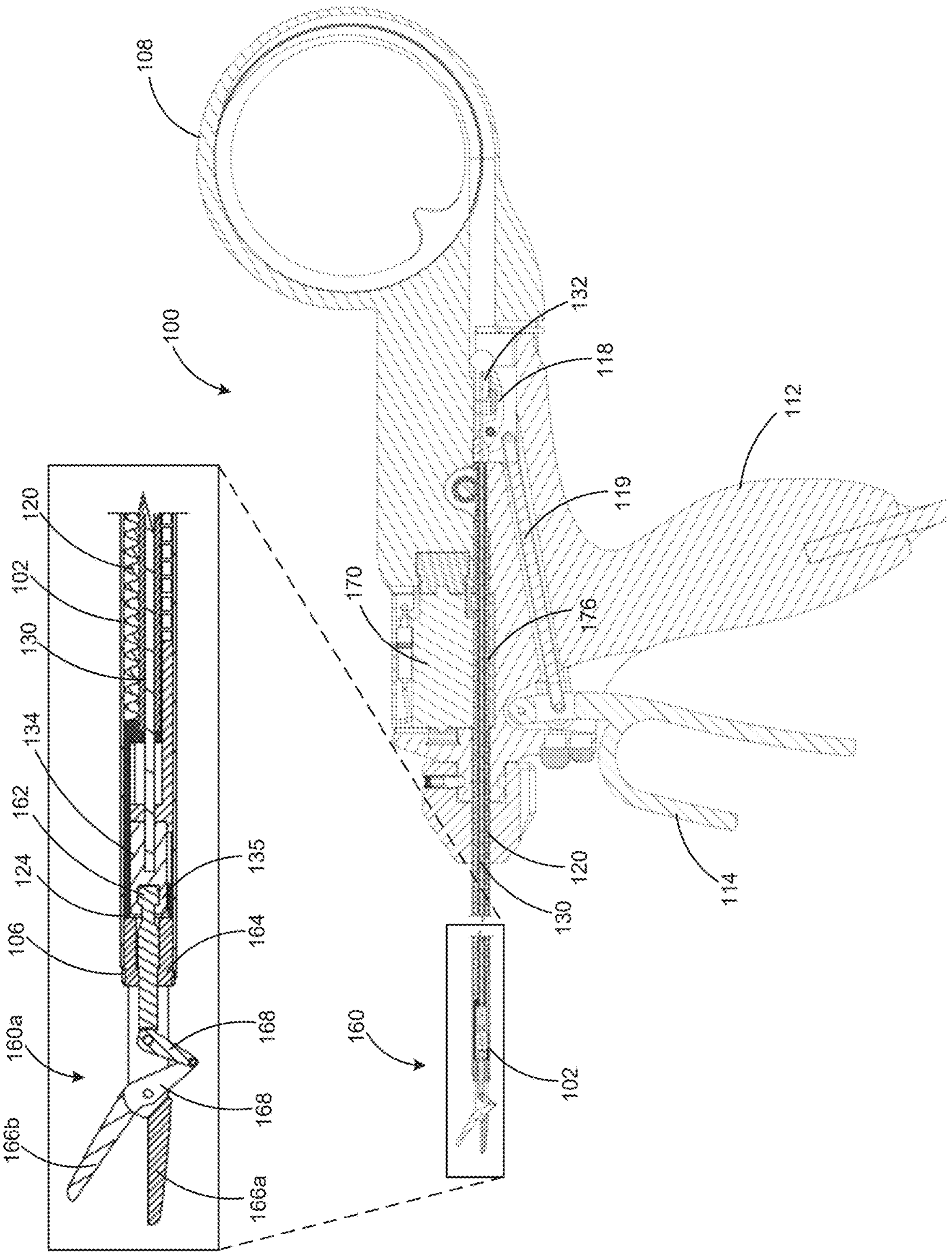

Accordingly, when base 162 is releasably coupled to coupling element 134 of rod 130, proximal coupling element 132 is releasably engaged with actuation end piece 118, and tool tip 160 is held in place via rack 120 and elongated shaft 102, actuation of rod 130, e.g., via actuator 114, in a first direction may cause rod 130 to move distally relative to rack 120 and apply a compressive force to base 162 to actuate tool tip 160 in a first degree of freedom, e.g., cause forceps tool tip 160*a* to open, and actuation of rod 130, e.g., via actuator 114, in a second direction opposite the first direction may cause rod 130 to move proximally relative to rack 120 and apply a tensile force to base 162 to actuate tool tip 160 in a second degree of freedom, e.g., cause forceps tool tip 160*a* to close, as described in further detail below with regard to FIGS. 11A and 11B. Accordingly, forceps tool tip 160*a* may be actuated to open/close without having to rely on a spring of the tool tip configured to facilitate opening of the forceps tool tip 160*a*. In some embodiments, coupling element 134 of rod 130 may be configured for providing a rotational degree of freedom with respect to the mounted tool tip, e.g., a rotational degree of freedom of rod 130 and/or rack 120 with respect to mounted tool tip 160.

Figure 9A:
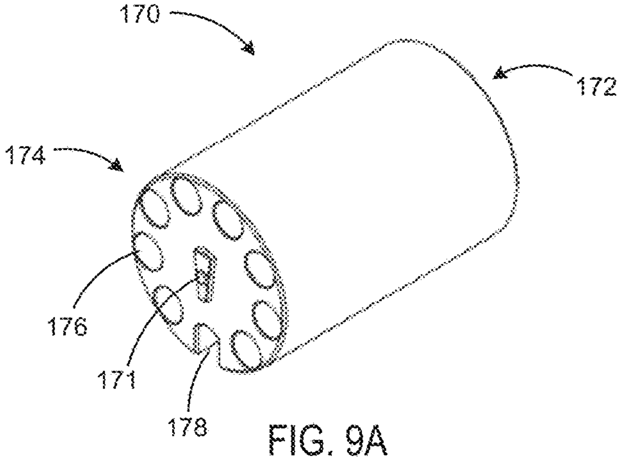
FIGS. 9A to 9F illustrate an exemplary magazine of the surgical device constructed in accordance with some embodiments.
Figure 9B:
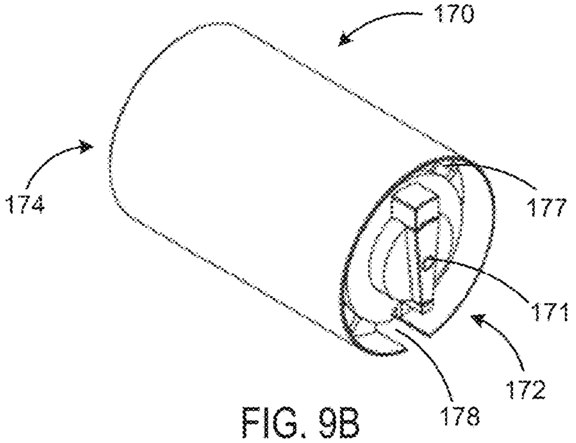
Figure 9C:
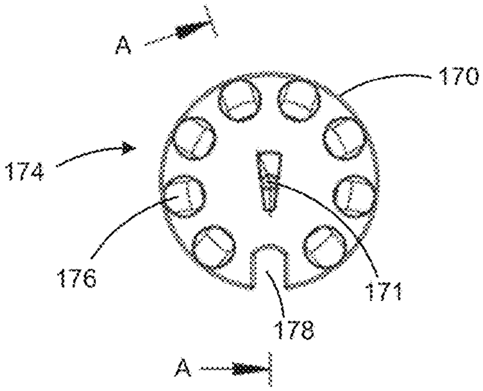
Figure 9D:
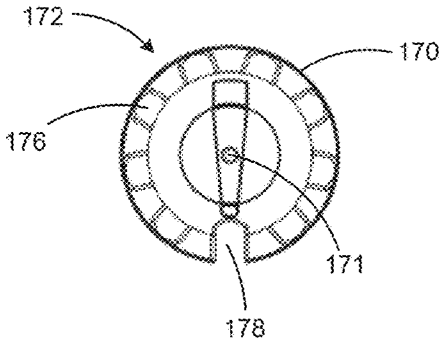
Figure 9E:
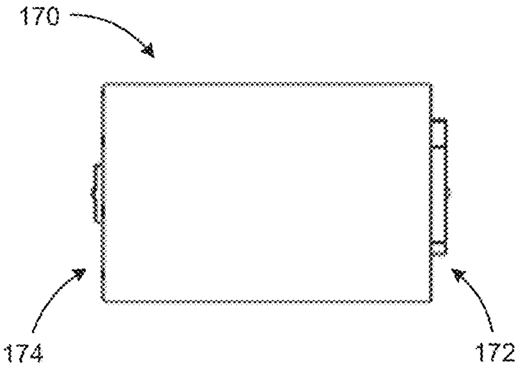
Figure 9F:
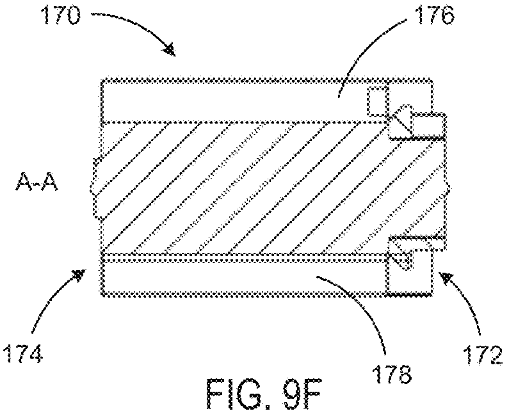

Referring now to FIGS. 9A to 9F, an exemplary magazine is provided. Magazine 170 may be a revolver-like drum with a plurality of chambers 176, each chamber 176 configured to house a different tool tip 160. For example, the tool tips may comprise at least one of a forceps tool having two jaws, a scissors tool, a probe, a dissector, a hook, a grasper, etc. Chambers 176 may be sized and shaped to slidably receive tool activation mechanism 103 therethrough. Moreover, each chamber 176 may comprise a geometry that permits tool tip 160 to be moved in and out of chamber 176 via distal end 174 of magazine 170, while prevent proximal movement of tool tip 160 proximally beyond proximal end 172 of magazine 170. For example, as shown in FIG. 9C, chambers 176 may each have a circular profile at distal end 174, sized and shaped to receive tool tip 160 therethrough, and as shown in FIG. 9D, chambers 176 may have a profile at proximal end 172 having a geometry that prevents passage of tool tip 160 therethrough. For example, the profile of chambers 176 at proximal end 172 may have flat sidewalls, such that tool tip 160 may not be moved proximally beyond proximal end 172 of magazine 170. In addition, at least a portion of the inner wall of chambers 176 may have a geometry that permits longitudinal movement of tool tip 160 therein, while preventing rotational movement of tool tip 160 therein relative to magazine 170. Accordingly, chambers 176 may be sized and shaped to facilitate handling of magazine 170 when magazine 170 is removed from body portion 110, e.g., for removing/replacing the tool tips disposed within the chambers of magazine 170.

As shown in FIGS. 9A to 9D, magazine 170 may comprise eight chambers 176, and slot 178, which is not configured to house a tool tip therein. Chambers 176 may be equally radially spaced from central axis 171 of magazine 171, such that magazine 170 may be selectively rotated about central axis 171, e.g., via actuation of the geared connection of drive gear 115 and driven gear 173 by motor 107*b*, to thereby align the angular position of a select chamber with track 101 of surgical device 100, as described above. As will be understood by a person having ordinary skill in the art, magazine 170 may have more or less than eight chambers 176, and/or more or less than one slot 178. Magazine 170 further may be configured to be movable along at least one translation axis. For example, magazine 170 may be configured to be movable along at least one translation axis along which chambers 176 of magazine 170 are arranged. In other words, chambers 176 of magazine 170 may be arranged along a line, allowing access to chambers 176 by sliding magazine 170. While magazine 170 is described herein as a revolver-like drum, in some embodiments, the magazine may have a different configuration that does not require rotation to align its chambers with track 101. For example, the chambers of the magazine may be arranged in a linear manner such that the magazine drive may be configured to cause the magazine to move translationally to align the chamber holding the selected tool tip with the track of the surgical device.

Figure 10A:
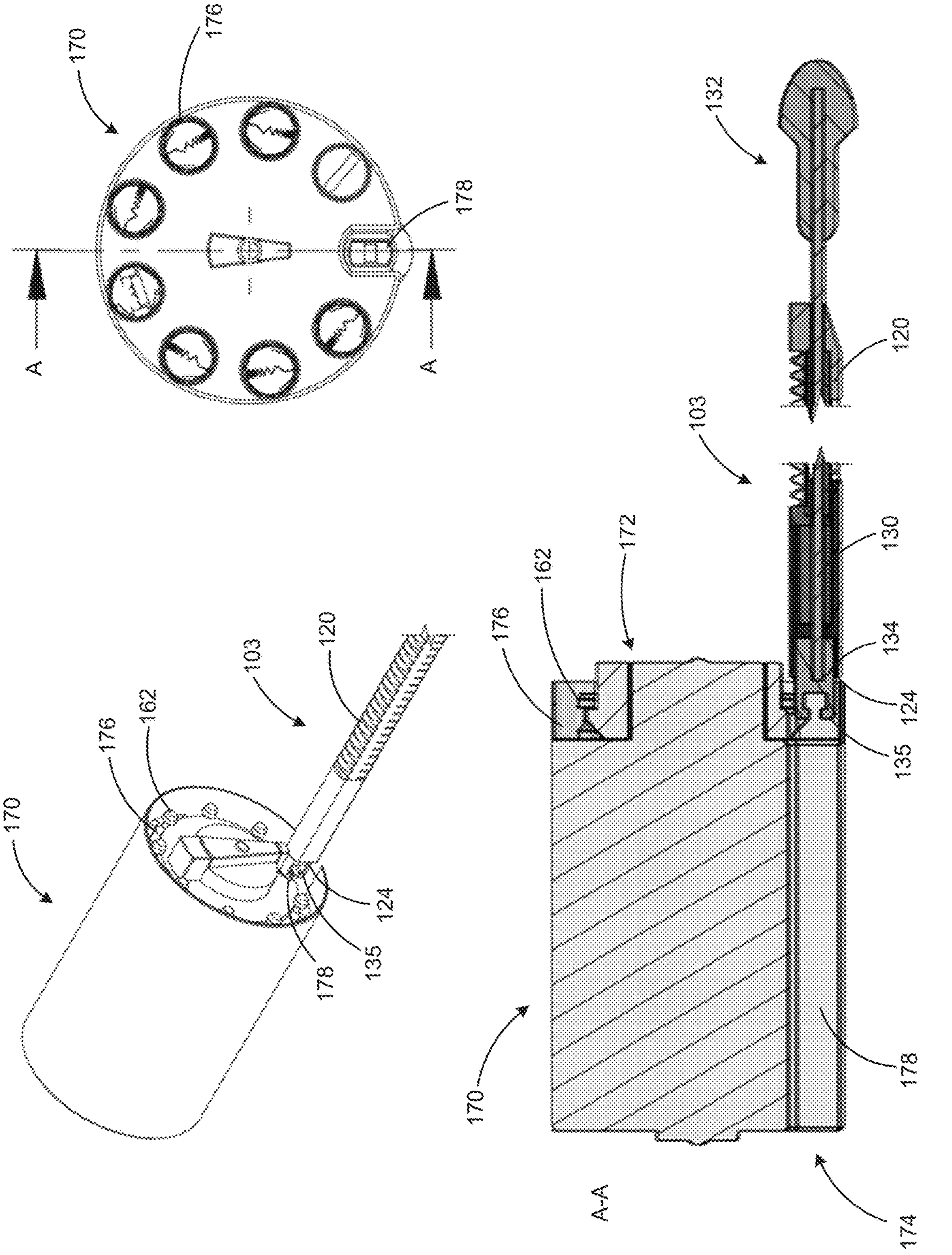
FIGS. 10A to 10C illustrate advancement of a select tool tip from the magazine of the surgical device.
Figure 10B:
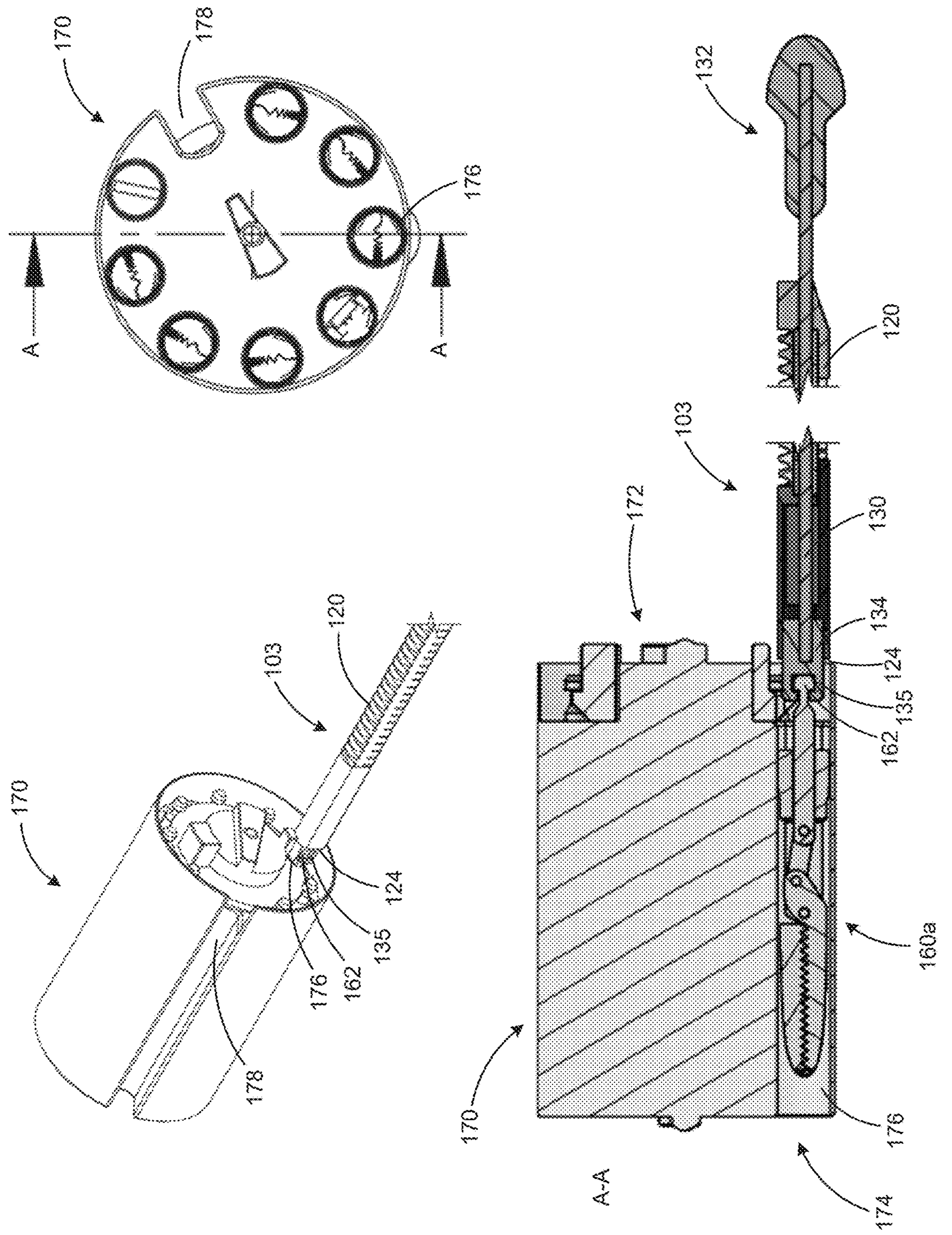
Figure 10C:
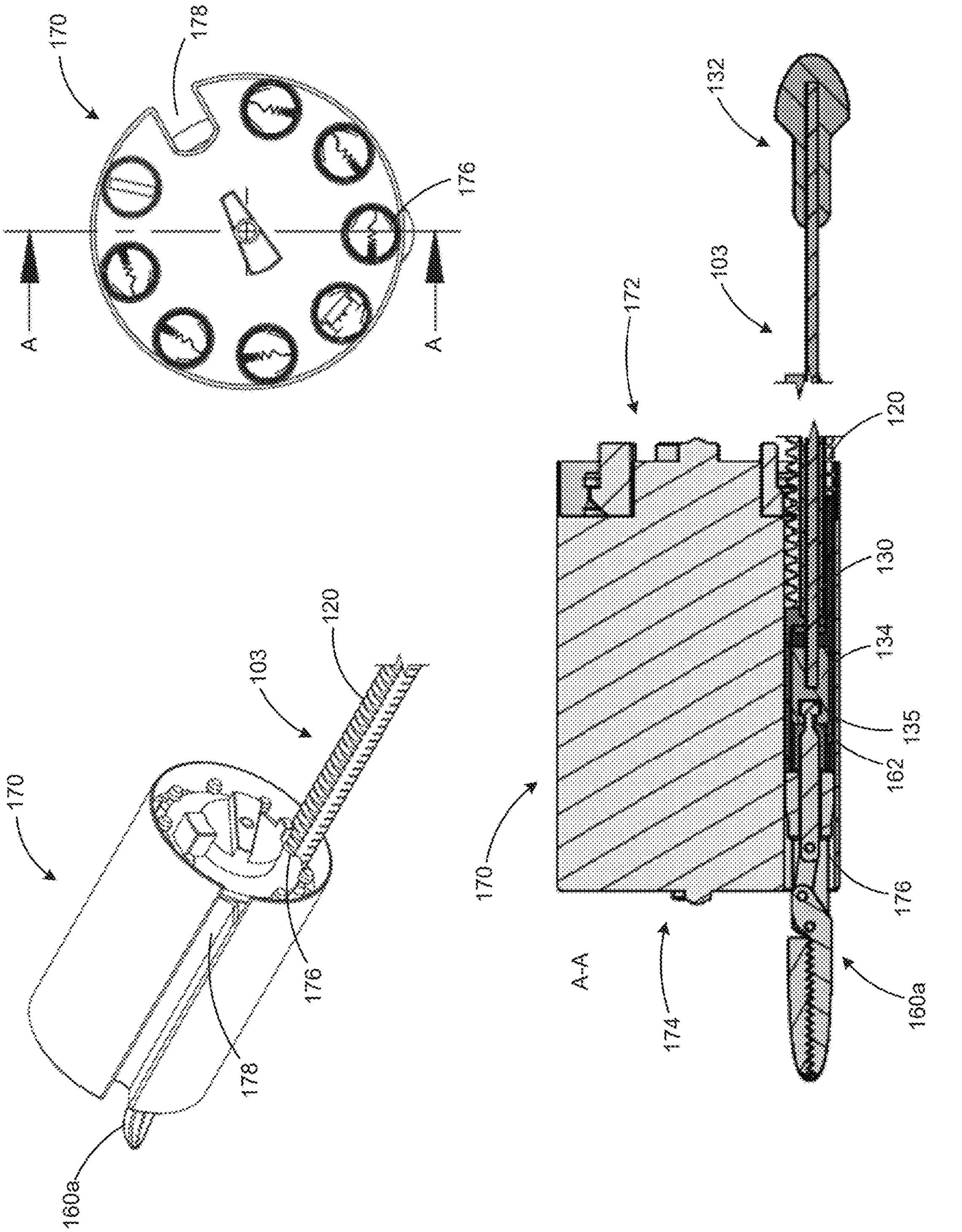

Referring now to FIGS. 10A to 10C, selection of an interchangeable tool tip is provided. In FIG. 10A, empty slot 178 of magazine 170 is aligned with track 101 of surgical device 100, and accordingly, with tool activation mechanism 103 in its retracted position, such that distal end 124 of rack 120 and distal coupling element 134 of rod 130 are positioned within track 101 proximal to slot 178. Upon selection of a desired tool tip, e.g., via display 14 and actuation of actuator 113*b* and actuator 113*c*, the magazine drive may cause selective rotation of magazine 170 until the angular position of the select chamber 176 holding the desired tool tip, e.g., forceps tool tip 160*a*, is aligned with track 101, and accordingly, tool activation mechanism 103, as shown in FIG. 10B, and base 162 of forceps tool tip 160*a* enters the cavity defined by fingers 135 of coupling element 134, as described above. Upon alignment of select chamber 176 and track 101, and accordingly base 162 with coupling element 134 of rod 130, both rack 120 and rod 130 disposed therein may be advanced together distally, e.g., via actuation of the geared connection of geared surface 128 of rack 120 and pinion gear 111 by motor 107*a* of rack drive 121, from its retracted configuration towards its extended configuration to thereby advance forceps tool tip 160*a* distally out of distal end 174 of chamber 176 of magazine and through the lumen of elongated shaft 102 until forceps tool tip 160*a* is disposed at and mounted to distal end 106 of elongated shaft 102, as shown in FIG. 10C. For example, advancement of tool activation mechanism 103 distally along track 101 applies a compressive force to forceps tool tip 160*a* via the engagement of base 162 and coupling element 134 of rod 130.

Referring now to FIGS. 11A to 11D, actuation of tool activation mechanism 103 is provided. Actuation of tool activation mechanism 103 may be further elaborated by referring to FIGS. 12A to 12G, which illustrate the coupling mechanism between tool activation mechanism 103 and actuation bar end piece 118 of surgical device 100 during operation of the surgical device. FIGS. 11A and 11B illustrate the select tool tip 160, e.g., forceps tool tip 160*a*, mounted at distal end 106 of elongated shaft 102, with forceps tool tip 160*a* having jaws 166*a*, 166*b* in a closed state. Forceps tool tip 160*a* is a multi-part tool comprising a plurality of links, e.g., links 168, interconnected via a plurality of joints, between base 162 and jaws 166*a*, 166*b*, such that translational movement of base 162, e.g., via rod 130 while forceps tool tip 160*a* is coupled to distal end 106 of elongated shaft 102 and held in place via distal end 124 of rack 120 within elongated shaft 102, causes jaws 166*a*, 166*b* to transition between a closed state, as shown in FIG. 11A, and an open state, as shown in FIG. 11B. Accordingly, at least one tool part of the multi-part tool may be configured to be moved relative to another part of the multi-part tool, such as a remainder of the multi-part tool or a second moveable part of the multi-part tool. For example, the movable part of the multi-part tool may be, e.g., a cutting edge of a scissors tool or a jaw of a forceps tool, and the remainder or the second moveable part of the multi-part tool may be a corresponding edge or jaw of the multi-part tool. In some embodiments, the second moveable part of the multi-part tool also may be in a kinematic chain with the first moveable part, e.g., a lever that is connected to the first moveable part.

Figure 12A:
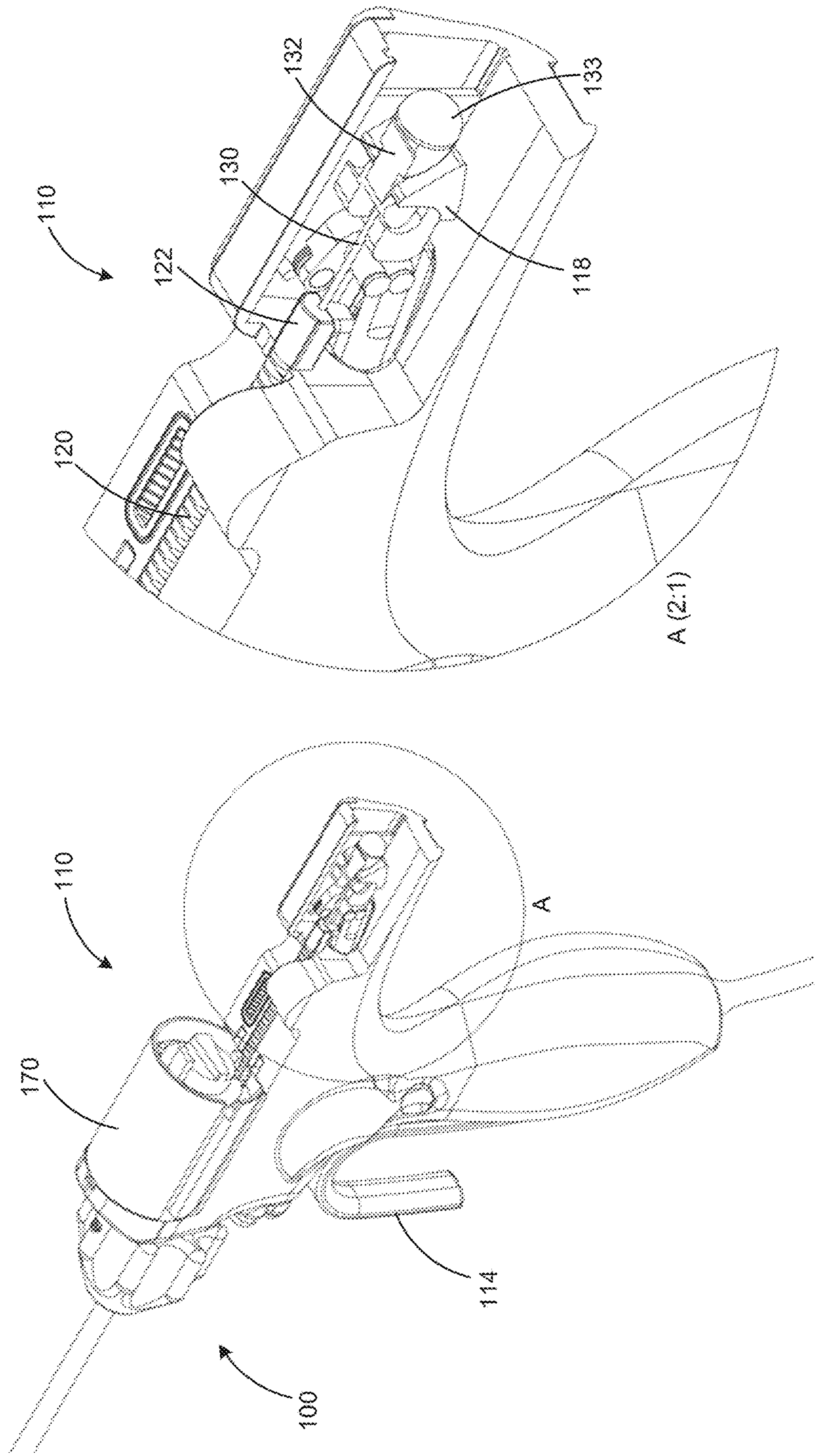
FIGS. 12A to 12G illustrate the coupling mechanism between the tool activation mechanism and an actuation bar of the surgical device during operation of the surgical device.
Figure 12B:
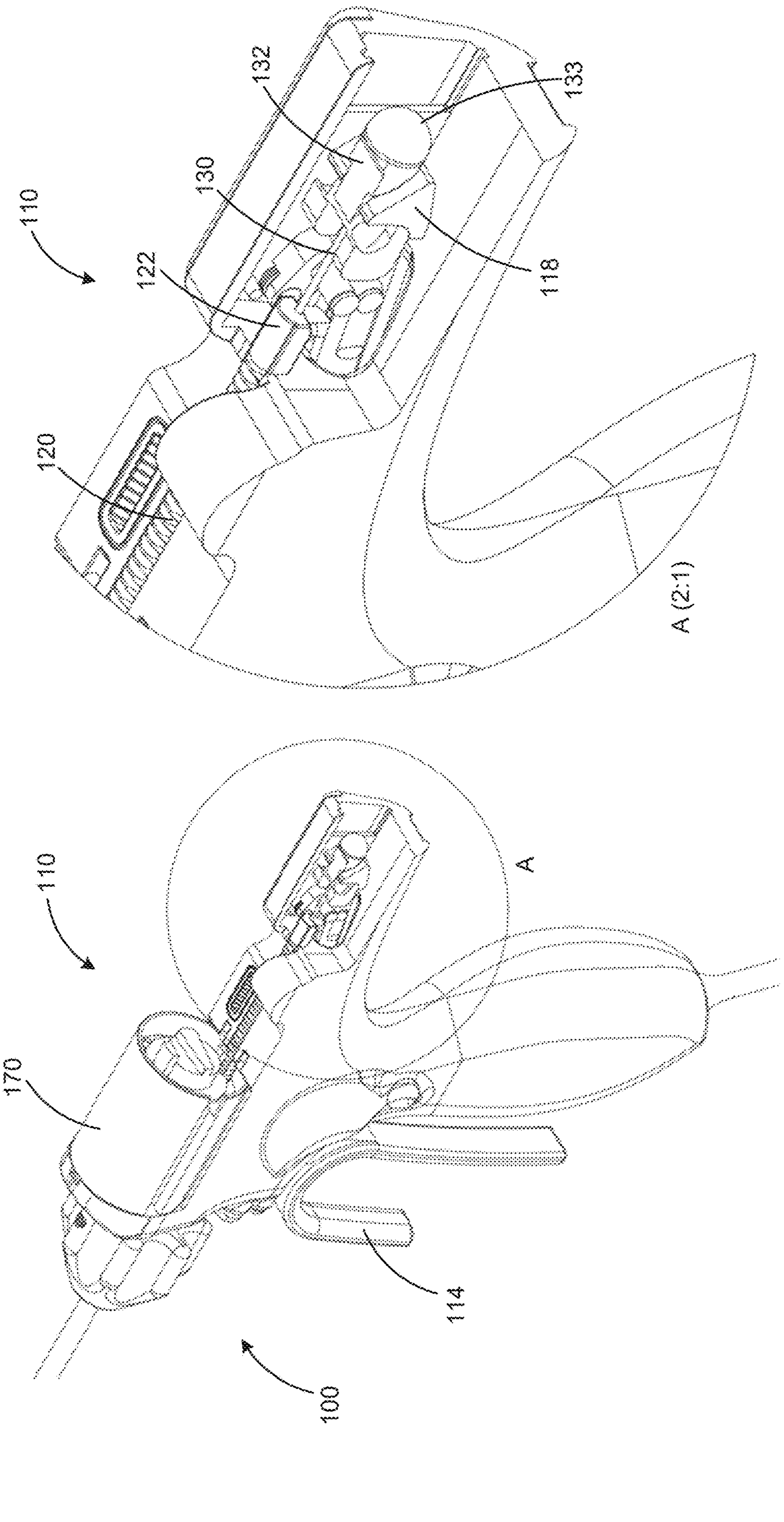

As shown in FIGS. 11A and 11B, actuator 114, e.g., an operating lever, may be operatively coupled to actuation bar end piece 118 via joint-connected actuation bar 119, e.g., an articulated connection. For example, actuator 114 may be spring loaded and biased towards the configuration shown in FIG. 11B. FIG. 12A illustrates body portion 110, particularly the coupling mechanism between the proximal end of tool activation mechanism 103, e.g., proximal end 122 of rack 120 and proximal coupling element 132 of rod 130, and actuation bar end piece 118 when forceps tool tip 160*a* is in the closed state shown in FIG. 11A, and FIG. 12B illustrates body portion 110, particularly the coupling mechanism between the proximal end of tool activation mechanism 103 and actuation bar end piece 118 when forceps tool tip 160*a* is in the open state shown in FIG. 11B. As shown FIGS. 12A and 12B, when forceps tool tip 160*a* mounted to distal end 106 of elongated shaft 102, such that tool activation mechanism 103 is in its fully extended configuration, actuation bar end piece 118 is in an engaged state, e.g., pivoted upward, where actuation bar end piece 118 is releasably engaged with proximal coupling element 132 of rod 130. For example, actuation bar end piece 118 may comprise a hook shape, e.g., comprising a wedge, that engages with proximal coupling element 132. For example, the hook shape of actuation bar end piece 118 may comprise a recess having a geometry configured to releasably lock with proximal coupling element 132. Accordingly, body portion 110 may comprise an internal cavity sized and shaped to hold actuation bar end piece 118 therein, and further to permit rotational and translational movement of actuation bar end piece 118 therein.

Accordingly, upon actuation of actuator 114 in a first direction, as shown in FIGS. 11A and 12A, actuation bar 119 causes actuation bar end piece 118 to move proximally relative to body portion 110 and apply a tensile force to rod 130 via the engagement of proximal coupling element 132 and actuation bar end piece 118, to thereby move rod 130, and accordingly base 162 of forceps tool tip 160*a*, proximally relative to rack 120 and elongated shaft 102. Proximal movement of base 162 of forceps tool tip 160*a* causes jaws 166*a*, 166*b* of forceps tool tip 160*a* to transition towards the closed state via links 168, as shown in FIG. 11A. Moreover, upon actuation of actuator 114 in a second direction, as shown in FIGS. 11B and 12B, actuation bar 119 causes actuation bar end piece 118 to move distally relative to body portion 110 and apply a compressive force to rod 130 via the engagement of proximal coupling element 132 and actuation bar end piece 118, to thereby move rod 130, and accordingly base 162 of forceps tool tip 160*a*, distally relative to rack 120 and elongated shaft 102. Distal movement of base 162 of forceps tool tip 160*a* causes jaws 166*a*, 166*b* of forceps tool tip 160*a* to transition towards the open state via links 168, as shown in FIG. 11B. Actuator 114 may not move rod 130 when no tool tip 160 is mounted to distal end 106 of elongated shaft 102, e.g., when proximal coupling element 132 of rod 130 and actuating bar end piece 118 are disengaged.

Figure 11C:
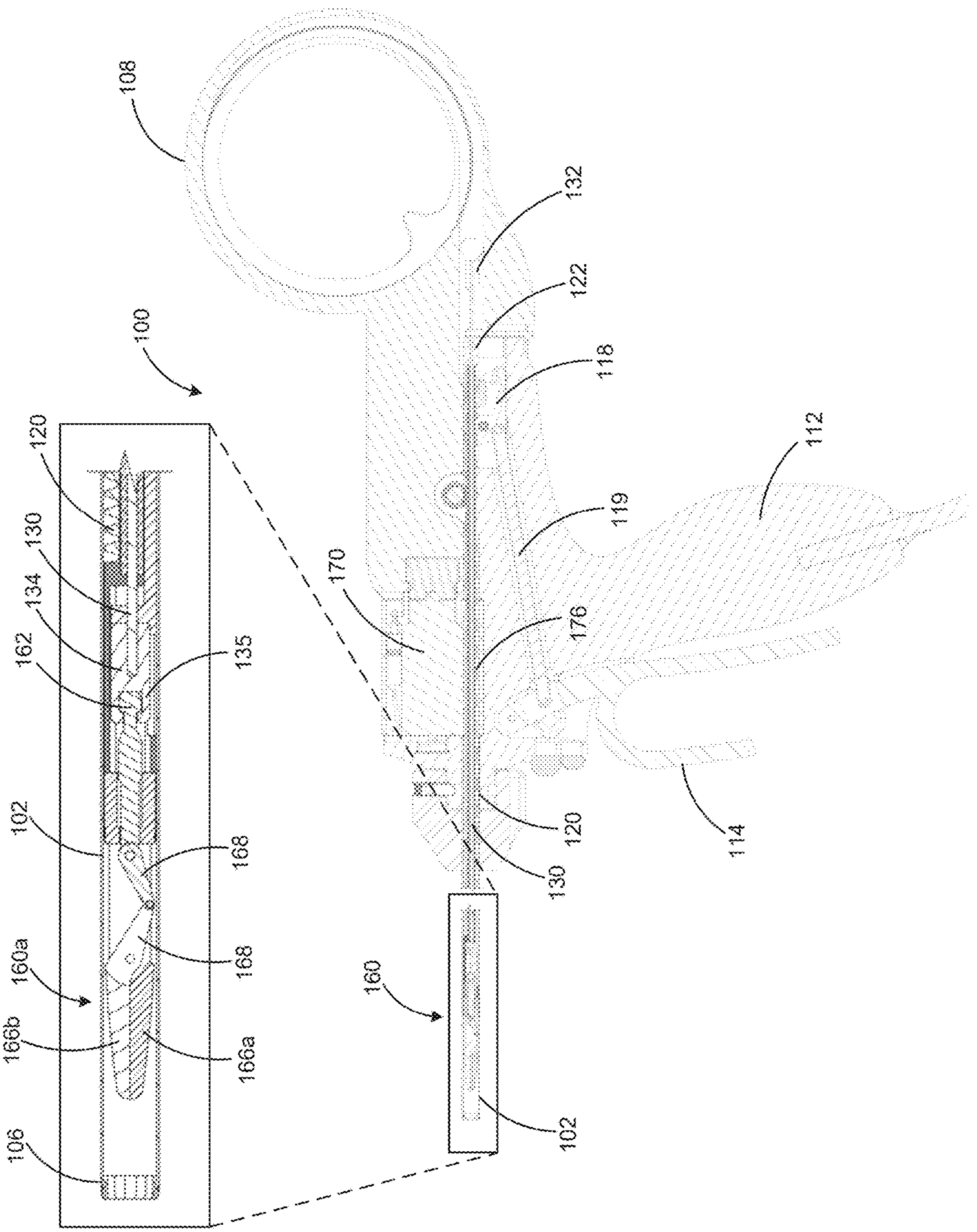
FIGS. 11C and 11D illustrate a tool change.
Figure 11D:
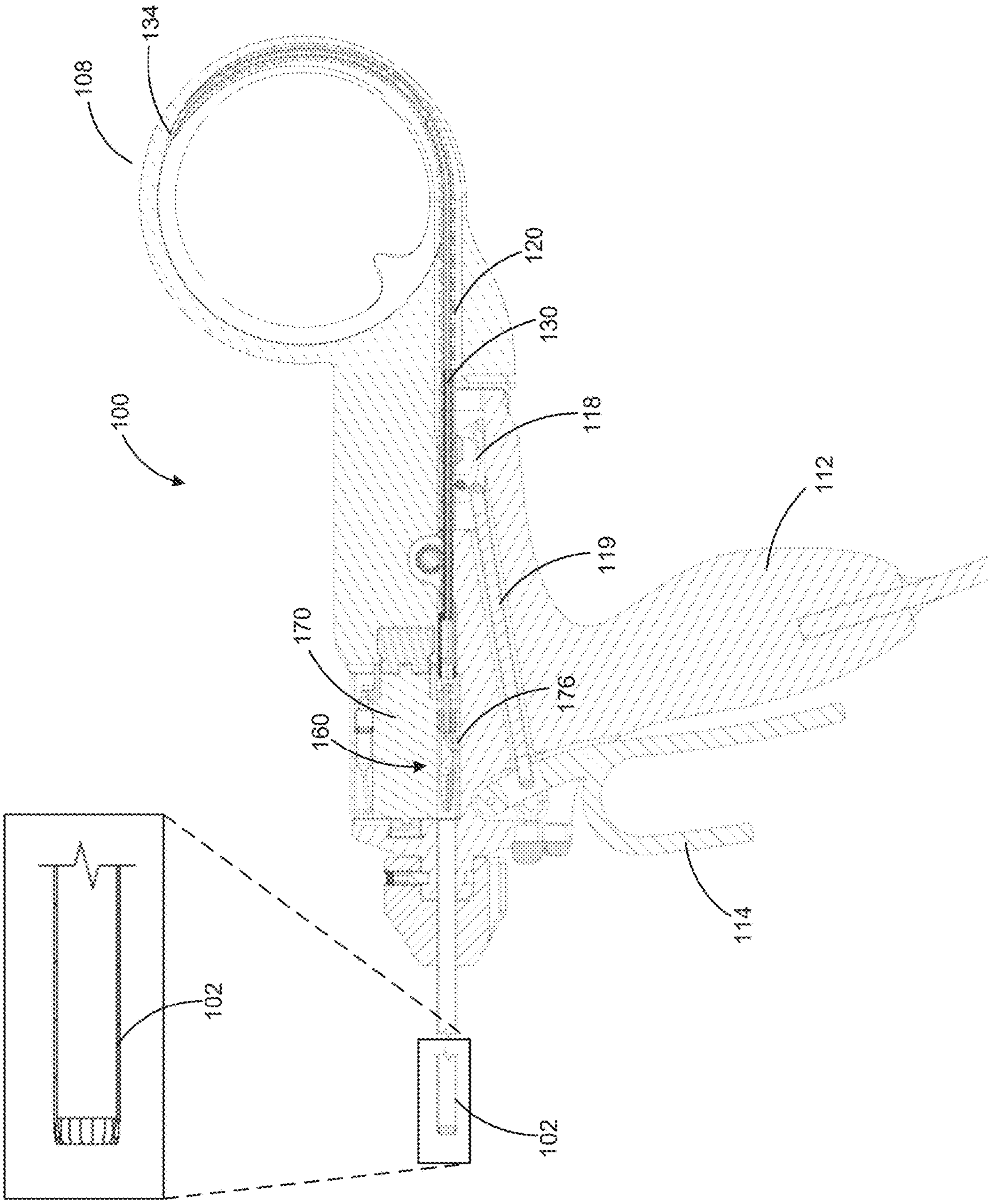

Upon selection of another interchangeable tool tip for mounting at distal end 106 of elongated shaft 102, tool activation mechanism 103 transitions from its extended configuration towards its retracted configuration, thereby pulling the current select tool tip 160, e.g., forceps tool tip 160*a*, proximally through the lumen of elongated shaft 102, as shown in FIG. 11C, until forceps tool tip 160*a* is returned to its corresponding chamber 176 of magazine 170, e.g., in a magazine configuration, and tool activation mechanism 103 is in its fully retracted position, as shown in FIG. 11D. As shown in FIG. 11D, in the fully retracted configuration, at least the proximal portion of tool activation mechanism 103 may bend about a bend axis, e.g., a center of receptacle 108, such that tool activation mechanism 103 is disposed within receptacle 108 in a rolled configuration. Accordingly, by disposing tool activation mechanism 103 in a rolled configuration within receptacle 108 of surgical device 100 in its fully retracted configuration, surgical device 100 provides a more compact device than currently available surgical devices. As described above, upon selection of a different tool tip, e.g., via display 14 and actuation of actuator 113*b* and actuator 113*c*, rack drive 121 causes translational movement of tool activation mechanism 103, e.g., via the geared connection between geared surface 128 of rack 120 and pinion gear 111, proximally along track 101 of surgical device 100.

Figure 12C:
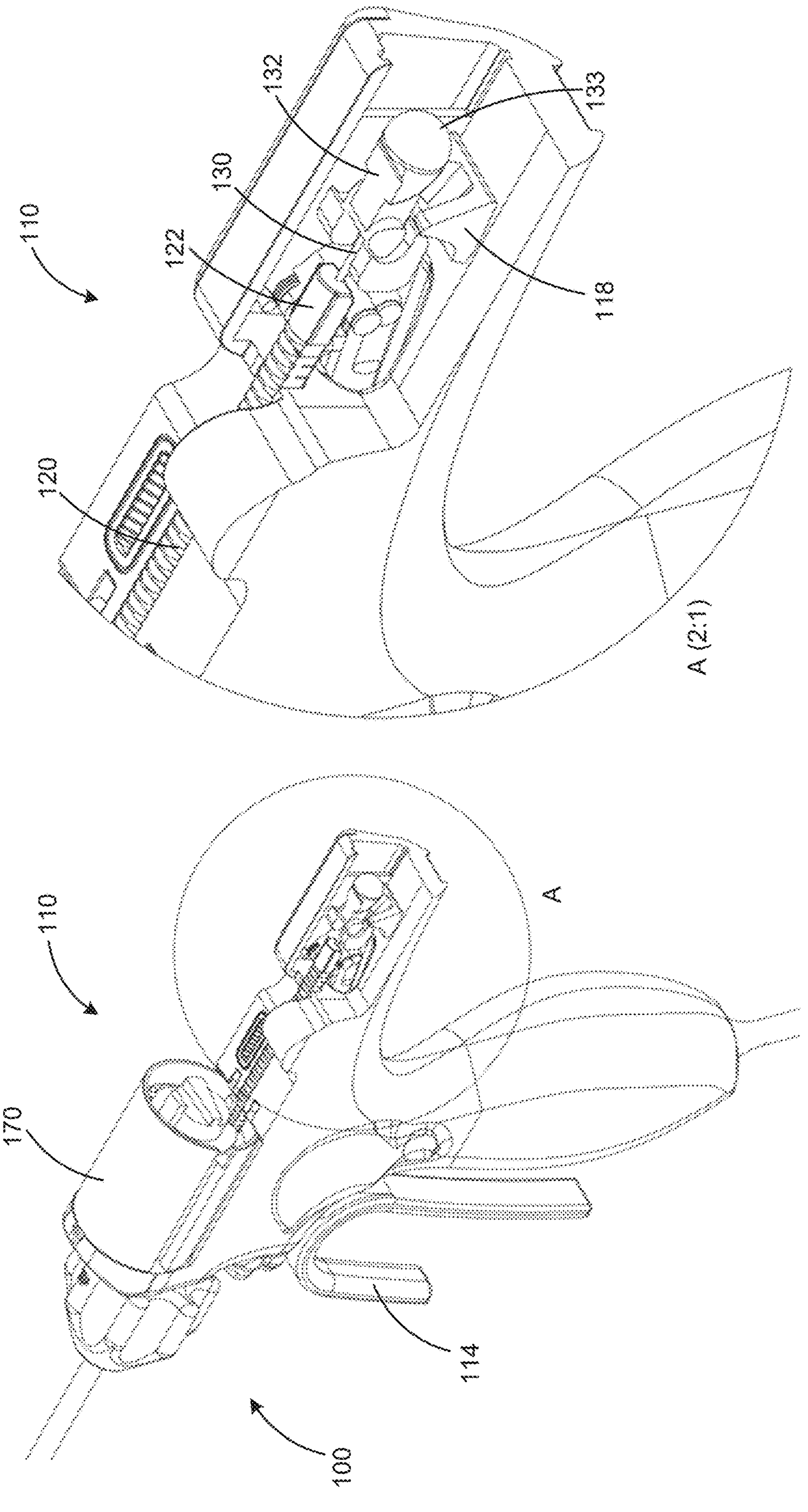
Figure 12D:
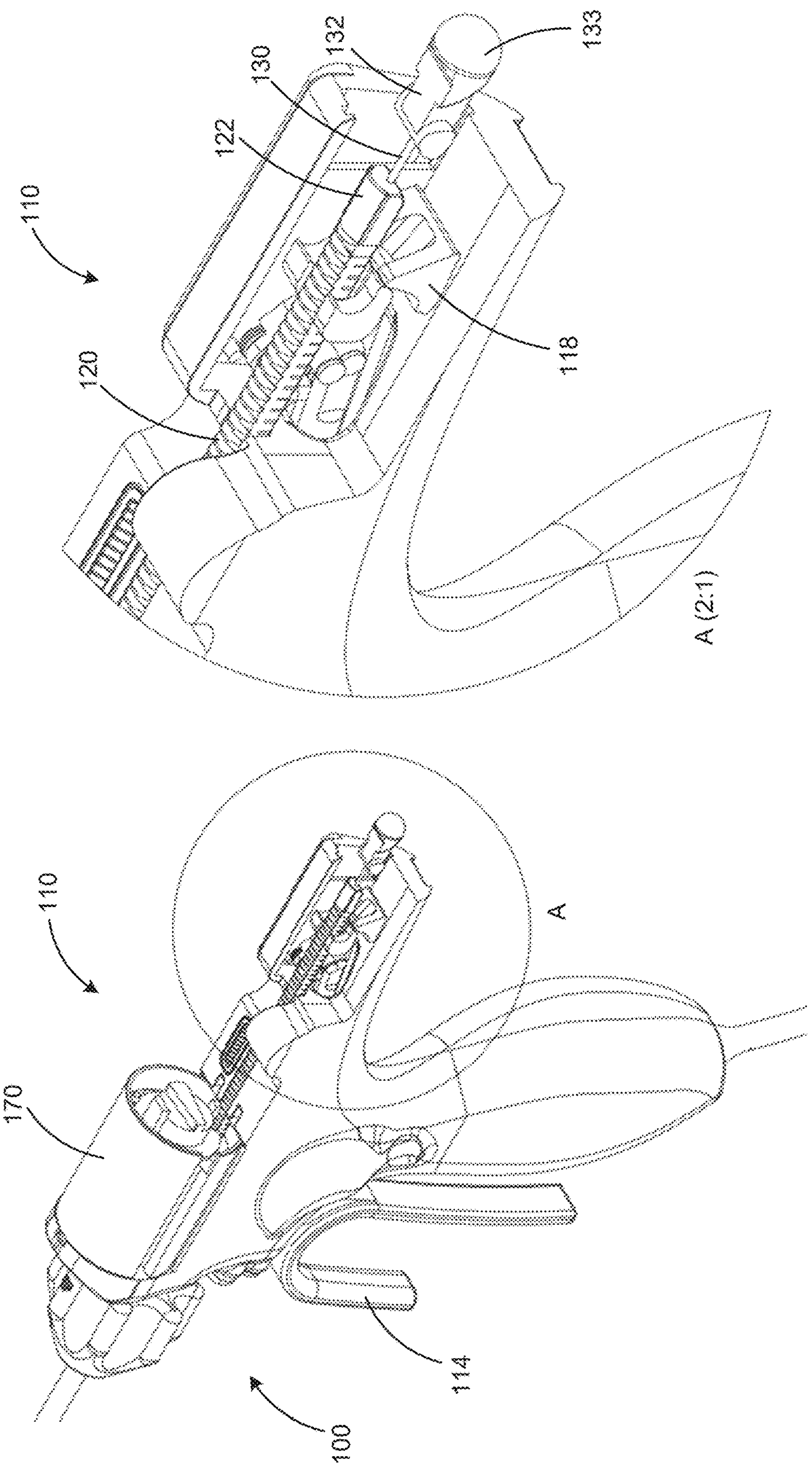

FIG. 12C illustrates the proximal end of tool activation mechanism 103 as tool activation mechanism 103 begins transitioning from its fully extended configuration towards its retracted configuration. For example, proximal end 122 of rack 120 may comprise a wedge shaped profile that engages with a corresponding geometry of actuation bar end piece 118 upon proximal movement of rack 120 relative to actuation bar end piece 118, which causes actuation bar end piece 118 to pivot from the engaged state to a disengaged state, as shown in FIG. 12C. As shown in FIG. 12C, in the disengaged state, actuation bar end piece 118 is disengaged from proximal coupling element 132, such that rod 130 is permitted to move proximally along with rack 120 relative to actuation bar end piece 118 and body portion 110, as shown in FIG. 12D.

Figure 12E:
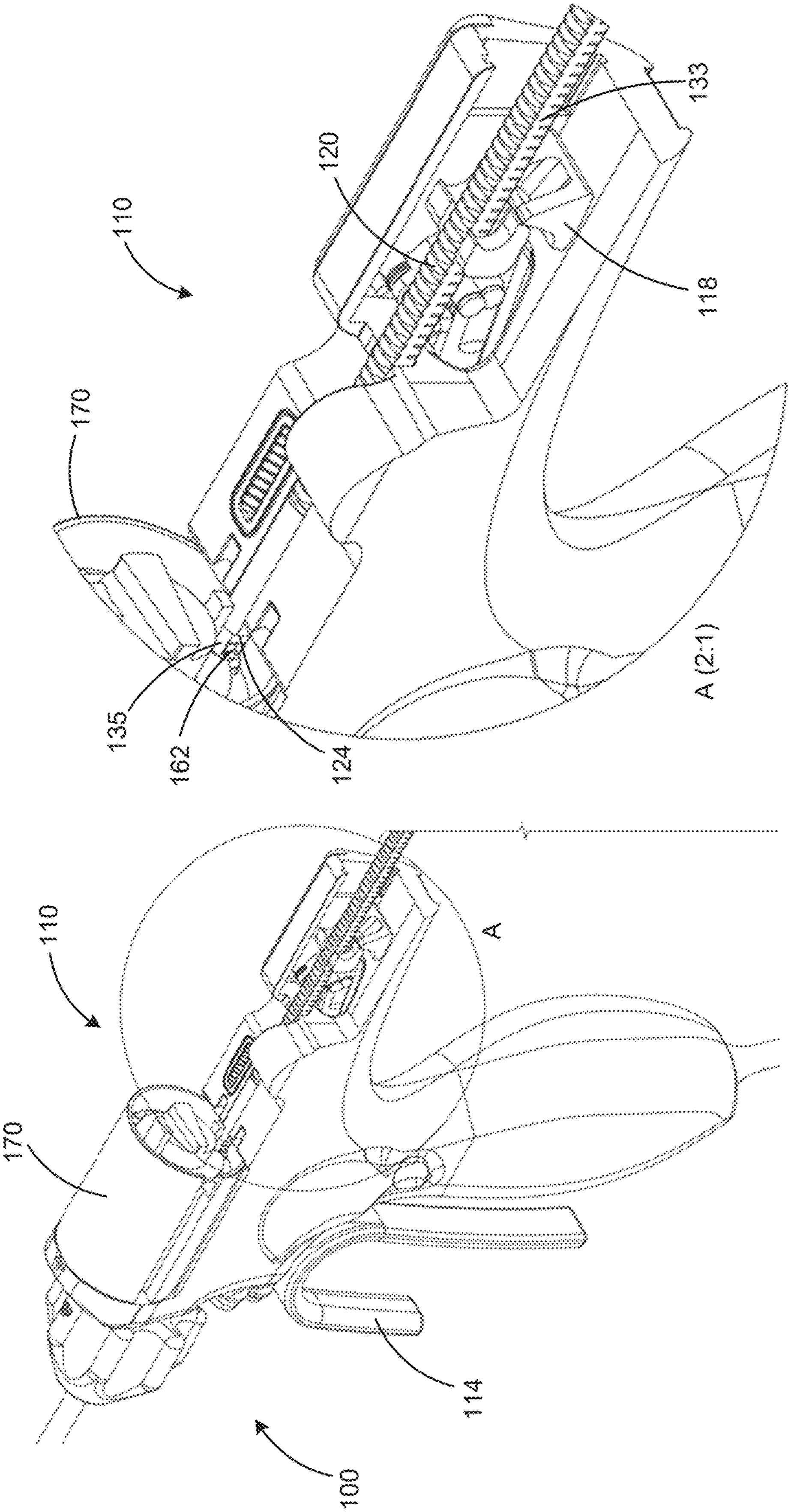

FIG. 12E illustrates body portion 110 when tool activation mechanism 103 is in its fully retracted position, such that the distal end of tool activation mechanism 103, e.g., distal end 124 of rack 120 and distal coupling element 134 of rod 130, is disposed proximal to magazine 170, and accordingly, the chamber of magazine 170 aligned with track 101 of surgical device 100. As described above, proximal end 172 of chamber 176 of magazine 170 may be configured to prevent proximal movement of tool tip 160 proximally beyond proximal end 172 of chamber 176. Accordingly, as tool activation mechanism 103 is moved to its fully retracted configuration and tool tip 160 is returned to its corresponding chamber 176, base 162 of tool tip 160 may be disengaged from coupling element 134 of rod 130 upon rotation of magazine 170, e.g., to thereby receive the base of another selected tool tip within the cavity of coupling element 134.

Figure 12F:
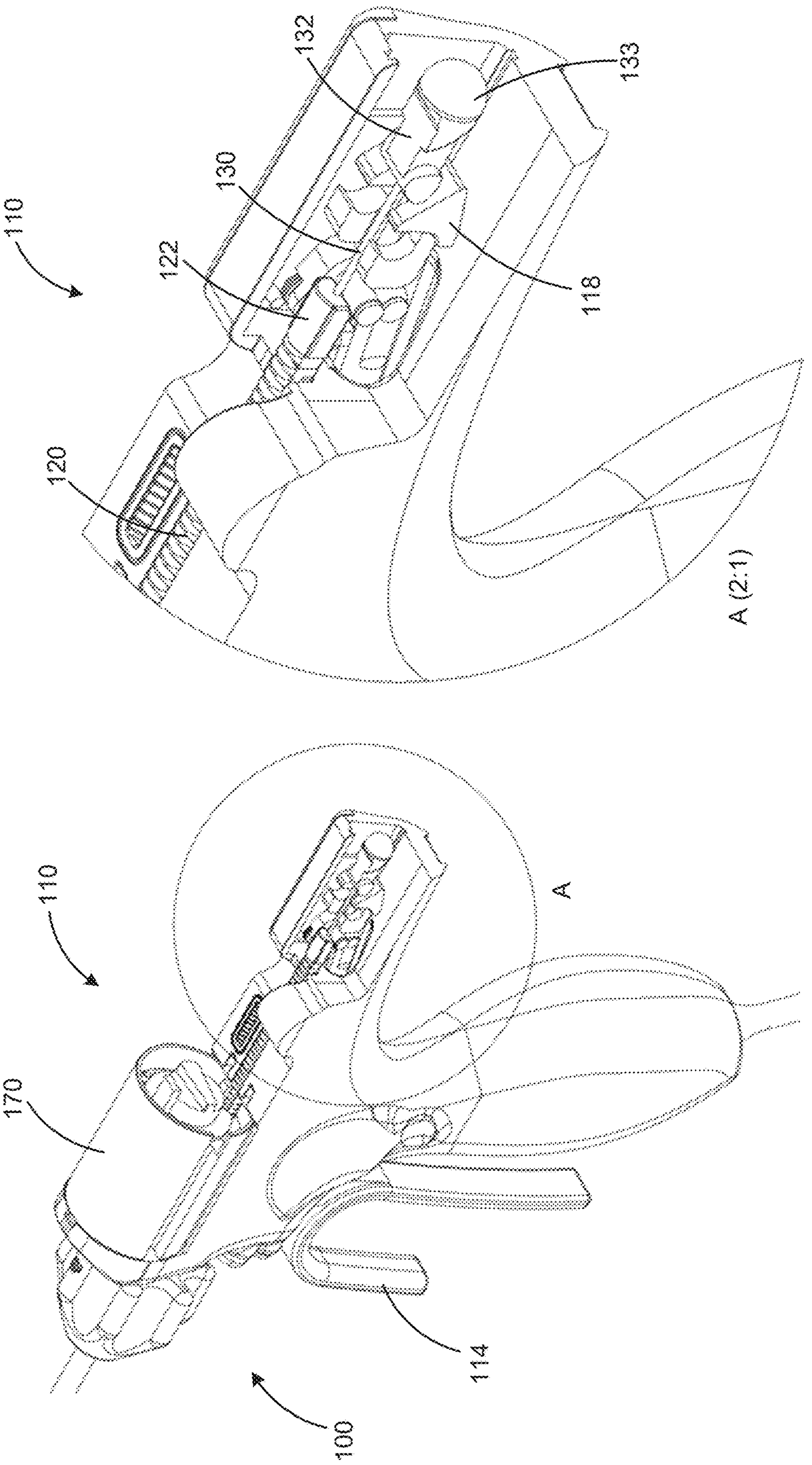
Figure 12G:
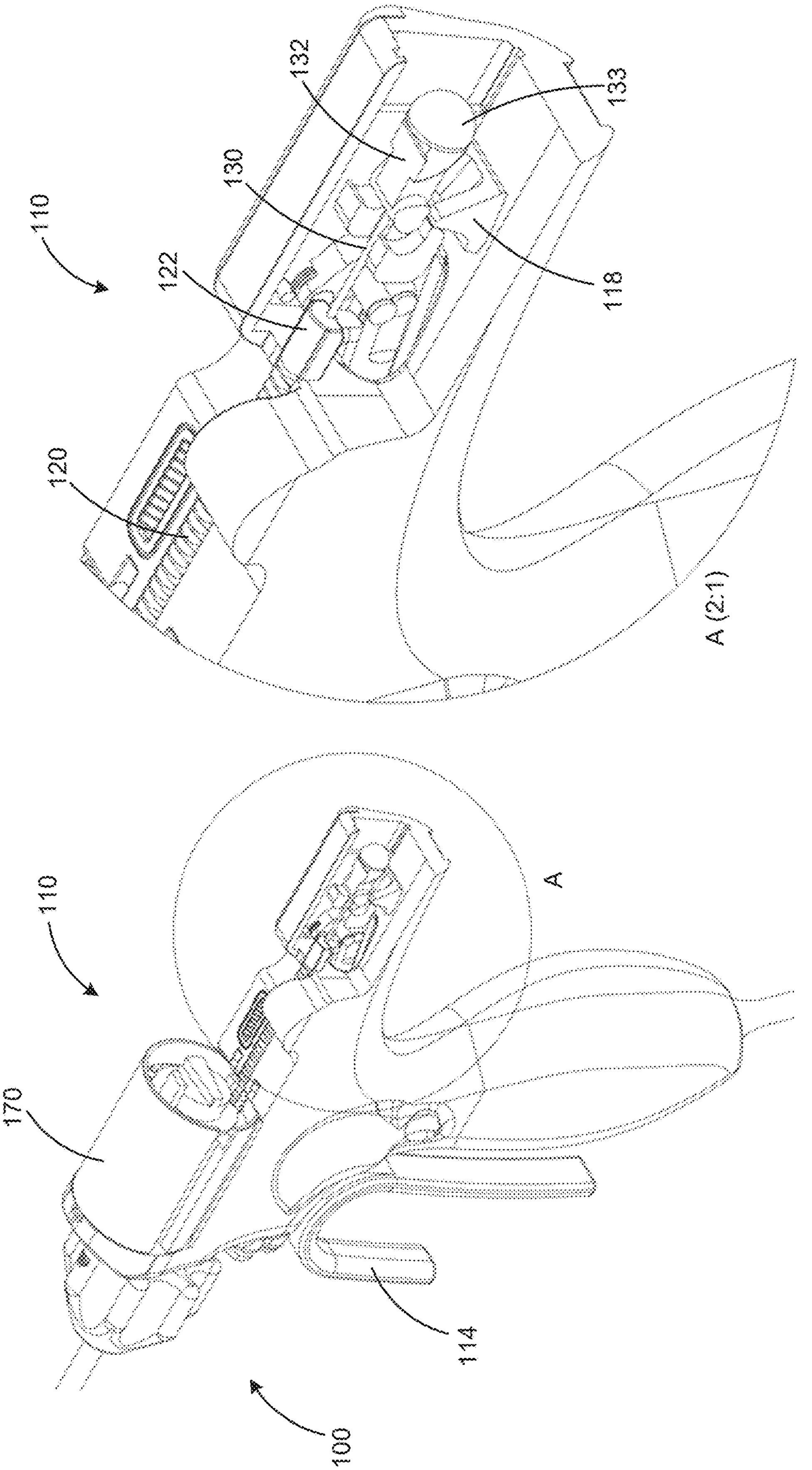

As described above, the magazine drive of surgical device 100 may then cause rotation of magazine 170, e.g., via the geared connection between drive gear 115 and driven gear 173, to align the angular position of the chamber holding the newly selected tool tip with track 101 of surgical device 100. Drive rack 121 of surgical device 100 may then cause translation of tool activation mechanism 103 distally relative to body portion 110 to transition from its retracted configuration towards its extended configuration, and engage and advance the select tool tip 160 from the magazine configuration within chamber 176 of magazine 170 towards distal end 106 of elongated shaft 102, as described above with regard to FIGS. 10B and 10C. As shown in FIG. 12F, when tool activation mechanism 103 is advanced distally such that proximal end 122 of rack 120 is disposed distal to actuation bar end piece 118, actuation bar end piece 118 may transition from its disengaged state towards its engaged state. For example, actuation bar end piece 118 may be spring loaded and biased towards its engaged state. As shown in FIG. 12F, proximal coupling element 132 of rod 130 is still disposed proximally to actuation bar end piece 118. As shown in FIG. 12G, further distal advancement of rack 120 and rod 130 relative to actuation bar end piece 118 causes proximal coupling element 132 to apply a force to actuation bar end piece 118, which causes actuation bar end piece 118 to pivot slightly downward to permit proximal coupling element 132 to move distally relative to actuation bar end piece 118, as shown in FIG. 12G. As described above, when tool activation mechanism 103 is in its fully extended configuration, actuation bar end piece 118 is engaged with proximal coupling element 132 of rod 130 in its engaged state, as shown in FIG. 12B, and tool tip 160 is in its mounted configuration at distal end 106 of elongated shaft 102.

Figure 13:
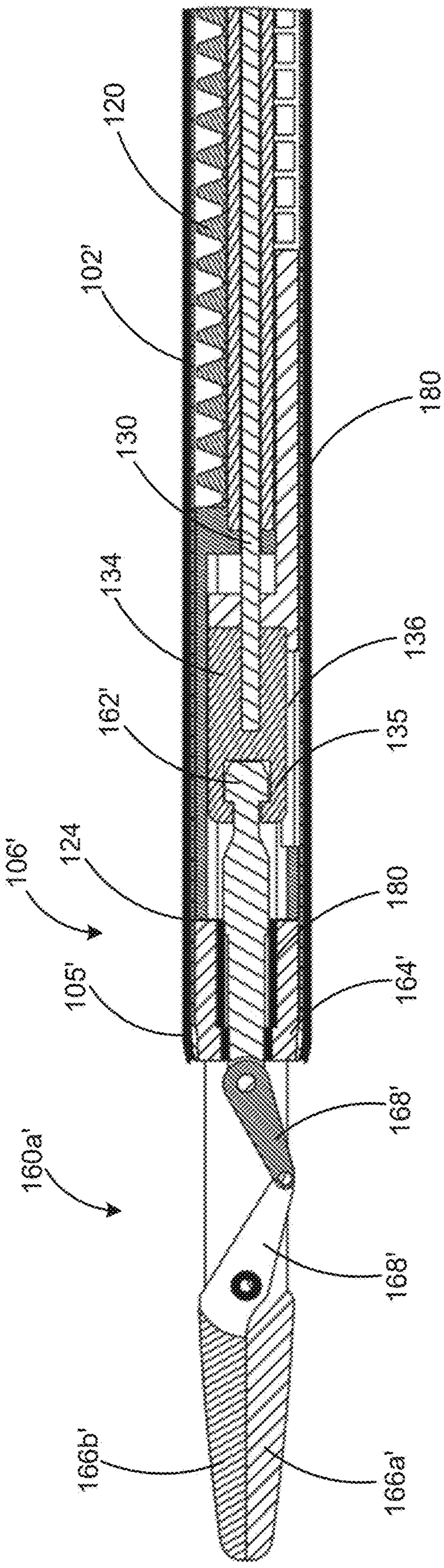
FIG. 13 illustrates a grasper tool tip mounted at the distal region of an alternative exemplary surgical device configured to transmit electrical energy in accordance with some embodiments.

Referring now to FIG. 13, the distal region of an alternative exemplary surgical device having a tool tip configured for electric cauterization mounted thereto is provided.

Distal region 106' of elongated shaft 102' may be constructed similar to distal region 106 of elongated shaft 102, with similar components having like prime reference numerals. For example, tool rotating structure 105' at distal end 106' of elongated shaft 102' corresponds with tool rotating structure 105 at distal end 106 of elongated shaft 102. Distal region 106' differs from distal region 106 in that elongated shaft 102' may be configured to transmit electrical energy to forceps tool tip **160*a*', which may be constructed similar to forceps tool tip 160*a* described above, with similar components having like prime reference numerals. For example, forceps tool tip 160*a*' may be a multi-part tool having links 168' interconnected via a plurality of joints between base 162' and jaws 166*a*', 166*b*', which corresponds to forceps tool tip 160*a* having links 168 interconnected via a plurality of joints between base 162 and jaws 166*a*, 166*b***.

The surgical device may be configured to provide two pole lines for transmitting power to different parts of forceps tool tip **160*a*', e.g., jaws 166*a*' and 166*b*'. For example, elongated shaft 102' may be configured to transmit electric power to forceps tool tip 160*a*', thereby forming a first pole line. In addition, rod 130 may further be configured to transmit electric power to jaws 166*a*', 166*b*' of forceps tool tip 160*a*', thereby forming a second pole line. In another example, elongated shaft 102' may also be configured to transmit electric power to forceps tool tip 160*a*'** via two integrated pole lines, thereby forming both a first and second pole line. Accordingly, the surgical device may be connected to a power generator configured to provide electrosurgical power to the surgical device, and accordingly, the tool tip mounted thereto for monopolar and/or bipolar electric cauterization.

In FIG. 13, electrically insulating layers 180 of forceps tool tip **160*a*' and elongated shaft 102' are indicated by bold lines. Accordingly, as shown in FIG. 13, elongated shaft 102' may comprise an outer electrically insulating layer 180, and parts of forceps tool tip 160*a*' may be insulated from each other via inner electrically insulating layer 180, e.g., when forceps tool tip 160*a*'** is configured for bipolar electric cauterization. In some embodiments, the select tool tip may be configured for monopolar cauterization, such that inner electrically insulating layers for electrically insulating parts of the tool tip may not be necessary.

Moreover, the body portion of the surgical device may comprise a bore configured for receiving the proximal portion of elongated shaft 102' therein, which may form a sleeve bearing. The bore may be made from a conductive material, such as stainless steel, and may be configured for transmitting electric power from the body portion to elongated shaft 102', e.g., the first pole line. In addition, power may be transmitted to rod 130 via the actuation bar end piece of the body portion, e.g., the second pole line. For example, the surgical device may comprise an electrical contact between the actuation bar end piece and the proximal coupling element of rod 130 when the actuation bar end piece engages the proximal coupling element of rod 130, as described above. Further, the surgical device may comprise at least one of a flexible cable, a joint, or a sliding contact for providing an electrical connection of a power line from the body portion and the actuation bar end piece.

Additionally, or alternatively, power may also be transmitted to rod 130 via a section of rack 120. For example, a section of rack 120 disposed within the body portion of the surgical device when the tool tip is mounted to distal region 106' of elongated shaft 102' may be conductive. Accordingly, rack 120 may optionally connect an electrical contact inside the body portion with rod 130. A remainder of rack

120 may comprise at least one insulating layer, such as a toothed layer made from an insulating polymer, to thereby advantageously electrically insulate rod 130 from elongated shaft 102'. In some embodiments, a distal portion of rack 120 and/or sliding member 136 may also be formed from an electrically insulating material. Accordingly, the surgical device may comprise at least two cables insulated from one another, e.g., for providing the two pole lines. For example, when a tool tip for bipolar cauterization is mounted to distal region 106' of elongated shaft 102', the two pole lines may be electrically connected to the output of a power generator, e.g., via a switching module.

In some embodiments, if a tool tip for monopolar cauterization is mounted to distal region 106' of elongated shaft 102', the switching module may automatically disconnect the unused pole line and may connect the other pole line to the monopolar output of the power generator. Similarly, if a tool tip for bipolar cauterization is mounted to distal region 106' of elongated shaft 102', the switching module may automatically connect both pole lines to the bipolar output of the power generator. Alternatively, the switching module may switch between monopolar and bipolar cauterization modalities responsive to user input, e.g., via controller 12. As will be understood by a person having ordinary skill in the art, permutations of the two cables for providing two pole lines, with the consequent permutations of the two voltages, or vice versa, may be encompassed by the other surgical devices described herein. In some embodiments, the surgical device further may comprise a third pole line for transmitting electric power to the tool for electric cauterization, as described in further detail below. For example, the third pole line may be configured to be attached to, and electrically insulated from, elongated shaft 102'. Accordingly, the surgical device may comprise at least three cables insulated from one another, e.g., for providing the three pole lines.

Figure 14:
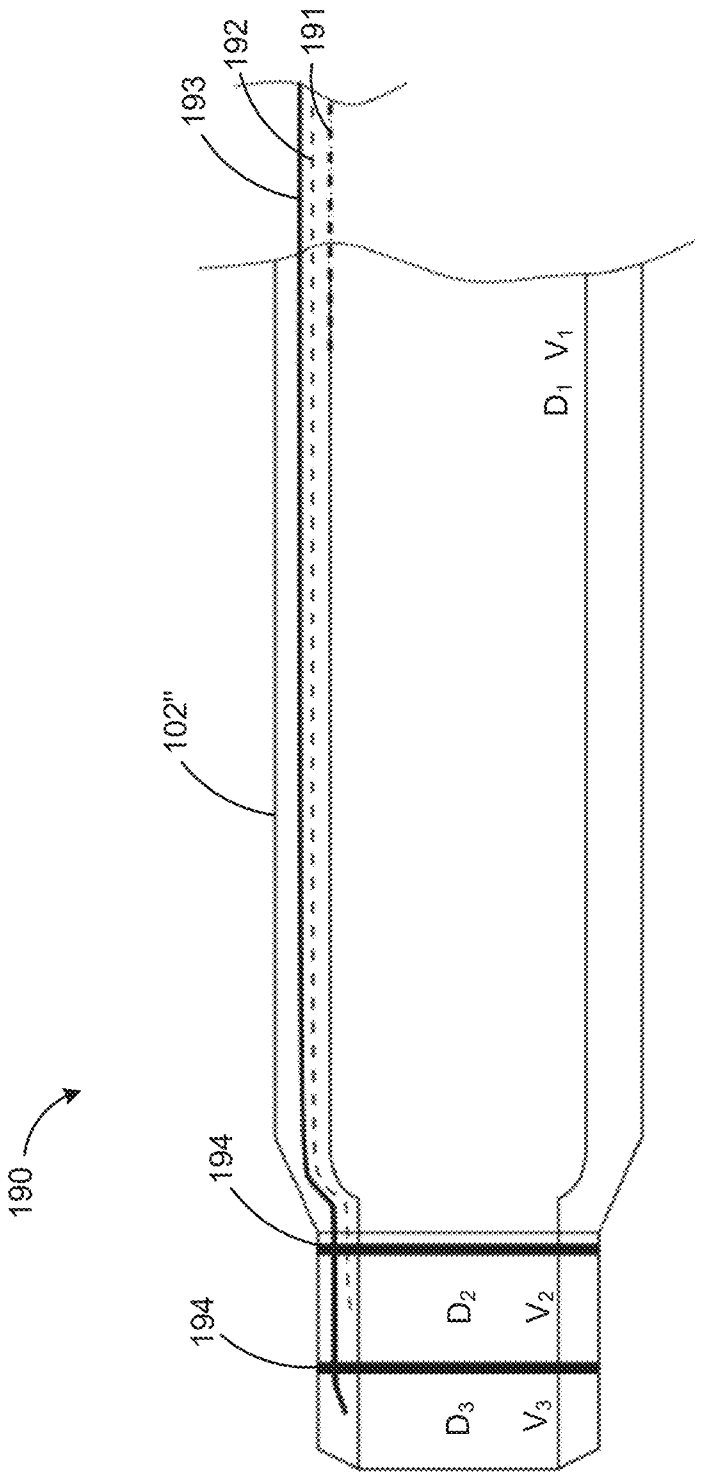
FIG. 14 illustrates the distal region of another alternative exemplary surgical device configured to transmit electrical energy constructed in accordance with some embodiments.

Referring now to FIG. 14, the distal region of the elongated shaft of an alternative exemplary surgical device is provided. Elongated shaft 102" may be constructed similar to elongated shaft 102'. As shown in FIG. 14, the surgical device may comprise three cables (e.g., cables 191, 192, 193) insulated from each other for transmitting electric power to the interchangeable tool tip mounted at distal portion 190 of elongated shaft 102" of the surgical device, e.g., at the distal end of elongated shaft 102" as described above, particularly to an interchangeable tool tip configured for electric cauterization. First cable 191, second cable 192, and third cable 193 may be comprised in elongated shaft 102". The voltages of the three cables may be different, e.g., $V_1$ for first cable 191, $V_2$ for second cable 192, $V_3$ for third cable 193. First cable 191 may contact elongated shaft 102" and/or define a first region $D_1$ of distal portion 190 of elongated shaft 102", such that first region $D_1$ comprises voltage $V_1$. Second cable 192 may contact a second region $D_2$ of distal portion 190, such that second region $D_2$ comprises voltage $V_2$. Third cable 193 may contact a third region $D_3$ of distal portion 190, such that third region $D_3$ comprises voltage $V_3$. Regions $D_1$, $D_2$, and $D_3$ may be electrically insulated from each other via insulating components 194. As will be understood by a person having ordinary skill in the art, permutations of the three cables, with the consequent permutations of the three voltages, or vice versa, may be encompassed by the other surgical devices described herein.

Figure 15A:
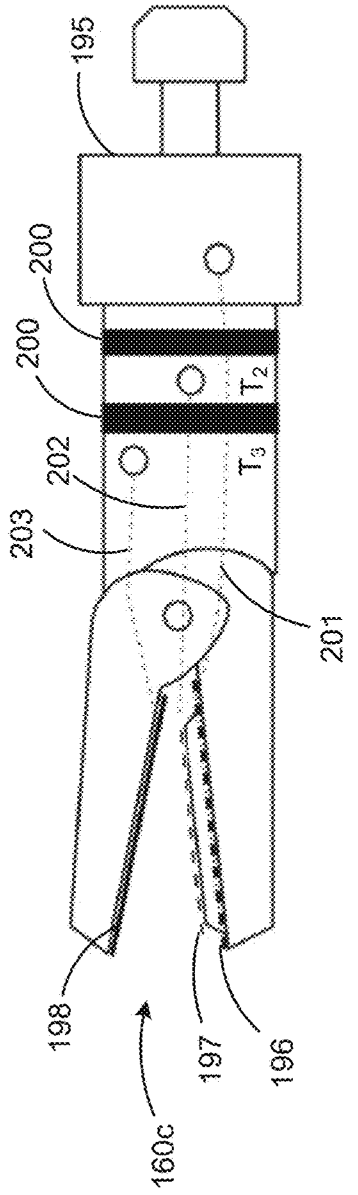
FIG. 15A illustrates an exemplary tool tip configured for tripolar electric cauterization constructed in accordance with some embodiments.
Figure 15B:
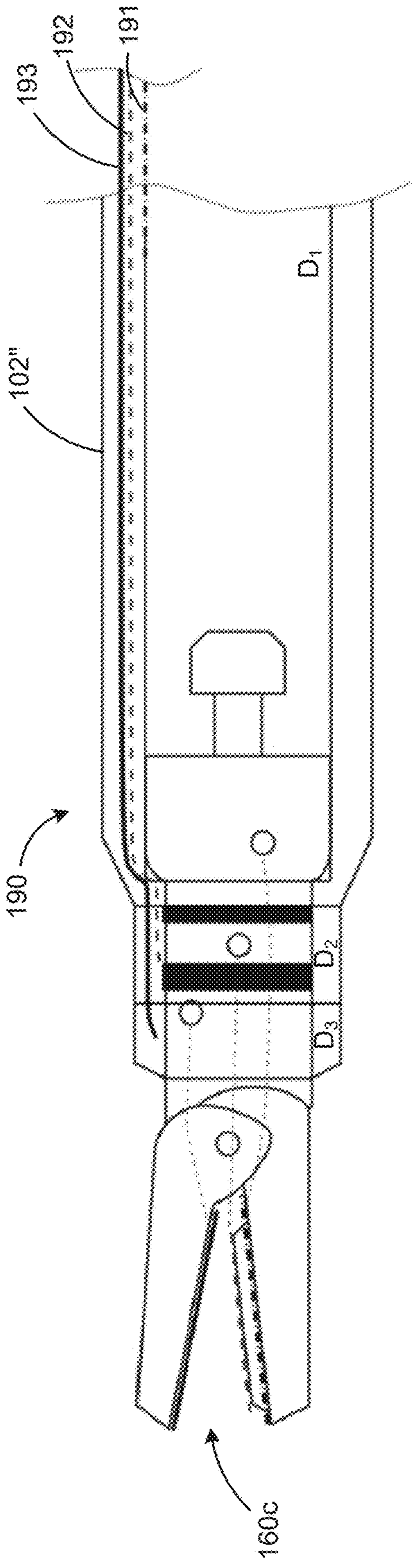
FIG. 15B illustrates the tool tip of FIG. 15A mounted at the distal region of the surgical device of FIG. 14.

Referring now to FIGS. 15A and 15B, an exemplary interchangeable tool tip configured for tripolar electric cauterization is provided. As shown in FIG. 15A, tool tip 160*c* may comprise a tool end portion 195. Tool tip 160*c* further may comprise first tool region $T_2$ and second tool region $T_3$, which may be electrically insulated from each other, and electrically insulated from tool end portion 195, via insulating elements 200. As will be understood by a person having ordinary skill in the art, tool regions $T_2$ and/or $T_3$ and/or tool end portion 195 may be encompassed by the other tool tips described herein. Tool tip 160*c* further may comprise first part 196, second part 197, and third part 198, which may be electrically insulated from each other. At least one of first part 196, second part 197, or third part 198 may be movable. For example, third part 198 may be movable.

In addition, tool tip 160*c* may be configured to have a distinct electrical connection to any of the cables (e.g., cables 191, 192, 193) of the surgical device. For example, the electrical connections may include electrical connections to first part 196, second part 197, and third part 198, e.g., tool tip 160*c* may comprise electrical connection 201 between first part 196 and tool end portion 195, electrical connection 202 between second part 197 and first tool region $T_2$, and electrical connection 203 between third part 198 and second tool region $T_3$, as shown in FIG. 15B. As will be understood by a person having ordinary skill in the art, permutations of connections 201, 202, and 203 may be encompassed by the other tool tips described herein. As shown in FIG. 15B, when tool tip 160*c* is mounted to distal portion 190 of elongated shaft 102", for example, via the tool activation mechanism, tool end portion 195 may generally contact first region $D_1$ of distal portion 190, thus establishing an electrical connection between first part 196 and first cable 191. First part 196 may therefore act as a first electrode. Further, first tool region $T_2$ may contact second region $D_2$ of distal portion 190, thus establishing an electrical connection between second part 197 and second cable 192. Second part 197 may therefore act as a second electrode. Further, second tool region $T_3$ may contact third region $D_3$ of distal portion 190, thus establishing an electrical connection between third part 198 and third cable 193. Third part 198 may therefore act as a third electrode.

Figure 16:
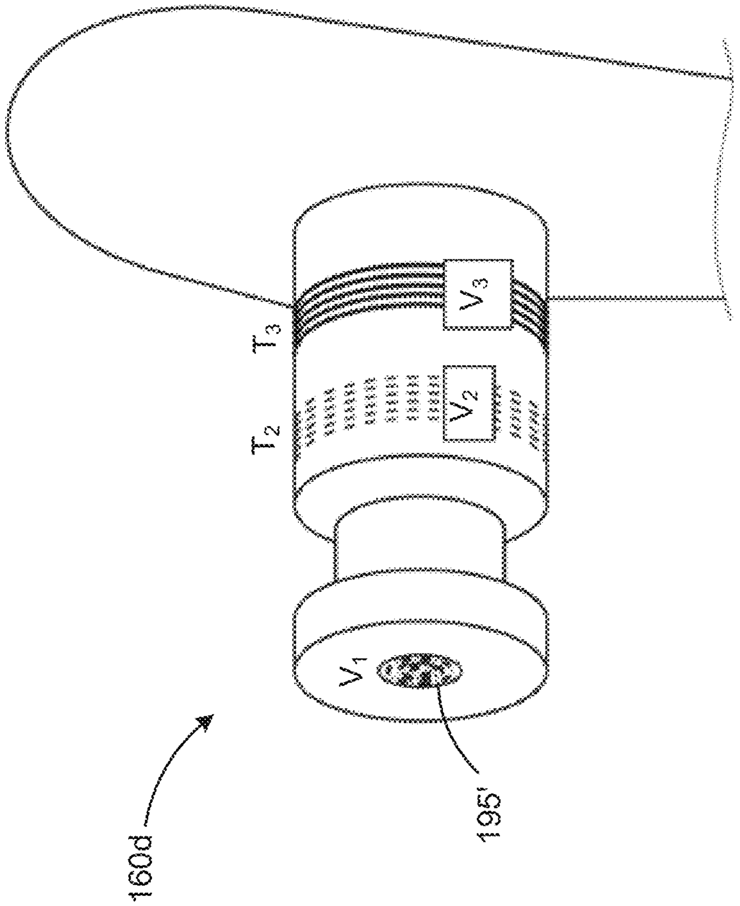
FIG. 16 illustrates the proximal region of an alternative exemplary tool tip configured for tripolar electric cauterization constructed in accordance with some embodiments.

Referring now to FIG. 16, the proximal portion of an alternative exemplary interchangeable tool tip configured for tripolar electric cauterization is provided. Tool tip 160*d* may be constructed similar to tool tip 160*c*. For example, tool end portion 195' of tool tip 160*d* corresponds with tool end portion 195 of tool tip 160*c*. When the tool tip 160*d* is mounted to the distal portion of the elongated shaft of the surgical device (not shown), tool end portion 195' may comprise first voltage $V_1$, first tool region $T_2$ may comprise a second voltage $V_2$, and second tool region $T_3$ may comprise third voltage $V_3$, as shown in FIG. 16.

Figure 17:
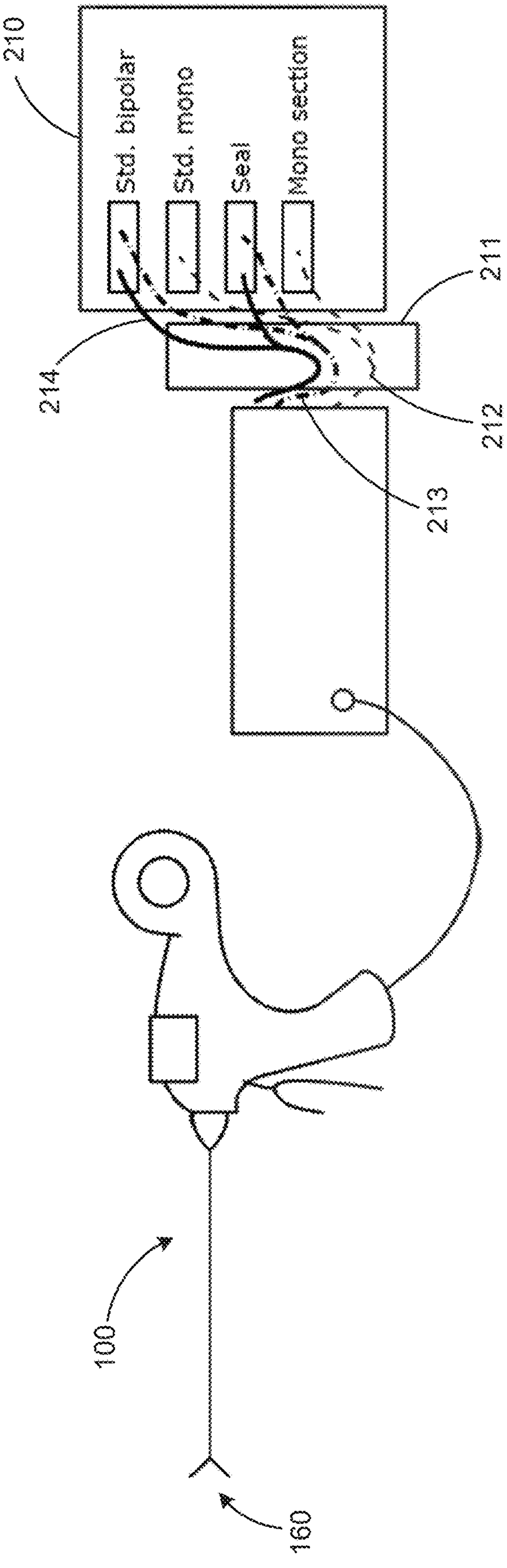
FIG. 17 illustrates an exemplary system for performing microinvasive surgery having a power generator operatively coupled to the surgical device via a switching module in accordance with some embodiments.

Referring now to FIG. 17, an exemplary surgical device is shown connected to a power generator via an exemplary switching module. Generator 210 may be configured to provide electrical power to surgical device 100, particularly to tool tip 160, e.g., an interchangeable tool tip configured for monopolar, bipolar, and/or tripolar cauterization, mounted on the distal portion of the elongated shaft of surgical device 100. Switching module 211 may be configured to manage the electrical connections between generator 210 and surgical device 100, as described above. For example, the connection to surgical device 100 may be achieved with one, two, or three cables (e.g., cables 212, 213, 214). For example, cables 212, 213, 214 may be electrically connected to cables 191, 192, 193, as described above with regard to FIG. 14, respectively. As will be understood by a person having ordinary skill in the art, permutations of the cables and/or their connections may be encompassed by the other surgical devices described herein.

More generally, it will be understood that the specific connections of cables 212, 213, 214 are shown as a preferred embodiment in FIG. 17 for illustrative purpose only and this should by no means be construed to limit the scope of the present invention. For example, the ordinarily skilled person will understand that embodiments of the present invention may encompass a number of cables and/or their connections different than the number of cables and/or their connections shown in FIG. 17.

The utilization of surgical device 100 connected to generator 210, via switching module 211, wherein surgical device 100 may comprise three cables, e.g., three pole lines, and wherein switching module 211 may be adapted for a tripolar setup, may have significant advantages. For example, with this setup, no safety critical switching of connections to the generator may be necessary. Further, as another example, no switching off of connections to the generator may be necessary, other than, for example, when the system's motors run. Moreover, if an interchangeable tool tip is locked in a wrong chamber of the magazine, no further safety risk may be introduced. Additionally, there may be no need for further identification of monopolar tool tips. As will be understood by a person having ordinary skill in the art, if an interchangeable tool tip with three electrodes is used, e.g., where the three electrodes are represented by three parts of the tool tip as described above, then a first couple of electrodes out of the three electrodes may be used to perform, e.g., sealing of tissue, and a second couple of electrodes out of the three electrodes may be used to perform, e.g., cutting of tissues.

Figure 18:
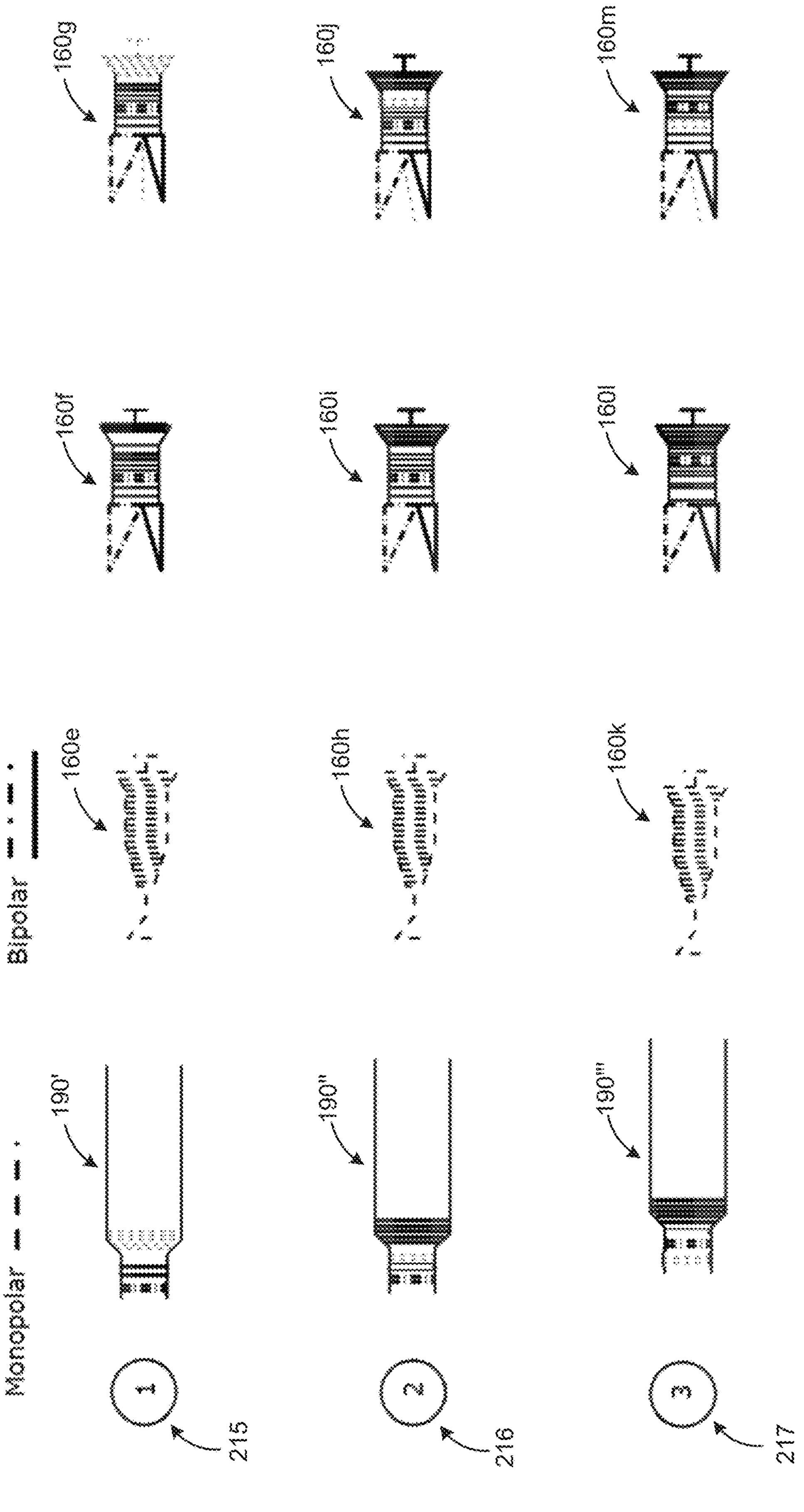
FIG. 18 illustrates exemplary electrode assignment options for various exemplary interchangeable tool tips in accordance with some embodiments.

Referring now to FIG. 18, electrode assignment options for exemplary interchangeable tool tips are provided. The tool tips (e.g., tool tips 160*e*-160*m*) may be adapted, for example, for monopolar, bipolar, and/or tripolar cauterization. The distal portions (e.g., distal portion 190', 190", 190") of the corresponding elongated shafts of the corresponding surgical devices may comprise three cables, as described above with regard to FIG. 14. As explained above, regions $D_1$, $D_2$, and $D_3$ of the each of the distal portions of the elongated shafts may be at different voltages. For example, in a first configuration 215, regions $D_1$, $D_2$, and $D_3$ of distal portion 190' may comprise voltages $V_2$, $V_3$, and $V_1$, respectively. Moreover, in a second configuration 216, regions $D_1$, $D_2$, and $D_3$ of distal portion 190" may comprise voltages $V_3$, $V_2$, and $V_1$, respectively. In a third configuration 217, regions $D_1$, $D_2$, and $D_3$ of distal portion 190" may comprise voltages $V_3$, $V_1$, and $V_2$, respectively.

The interchangeable tool tips (e.g., tool tips 160*e*-160*m*), particularly parts of the tool tips such as terminal parts of the tool tips, some of which may be movable, may be configured to have a distinct electrical connection to at least some of the three cables comprised in the surgical device, e.g., via electrical connections to regions $D_1$, $D_2$, and $D_3$. For example, an electrical connection of the terminal parts of the tool tips to region $T_2$, region $T_3$, and/or the tool end portion may be achieved with cables. The further electrical connection between regions $T_2$ and/or $T_3$, and regions $D_2$ and/or $D_3$ may be achieved with, e.g., spring contacts. The further electrical connection between the tool end portion and region $D_1$ may generally be present in most cases when the tool tip is mounted to the distal portion of the respective elongated shaft, unless insulating elements are used to prevent this. As described above, the terminal parts of the tool tips may act as electrodes. Insulation elements also may be utilized to electrically insulate the electrodes from each other and/or to electrically insulate the terminal parts of the tool tips from at least some of the three cables. The combination of the distinct electrical connection to at least some of the three cables and of the use of insulation elements may allow, e.g., (1) an interchangeable tool tip to be a monopolar hook 160*e*, a bipolar grasper 160*f*, and/or a tripolar grasper 160*g* in the first configuration 215, (2) an interchangeable tool tip to be a monopolar hook 160*h*, a bipolar grasper 160*i*, and/or a tripolar grasper 160*j* in the second configuration 216, and/or (3) an interchangeable tool tip to be a monopolar hook 160*k*, a bipolar grasper 160*l*, and/or a tripolar grasper 160*m* in the third configuration 217.

Figure 19:
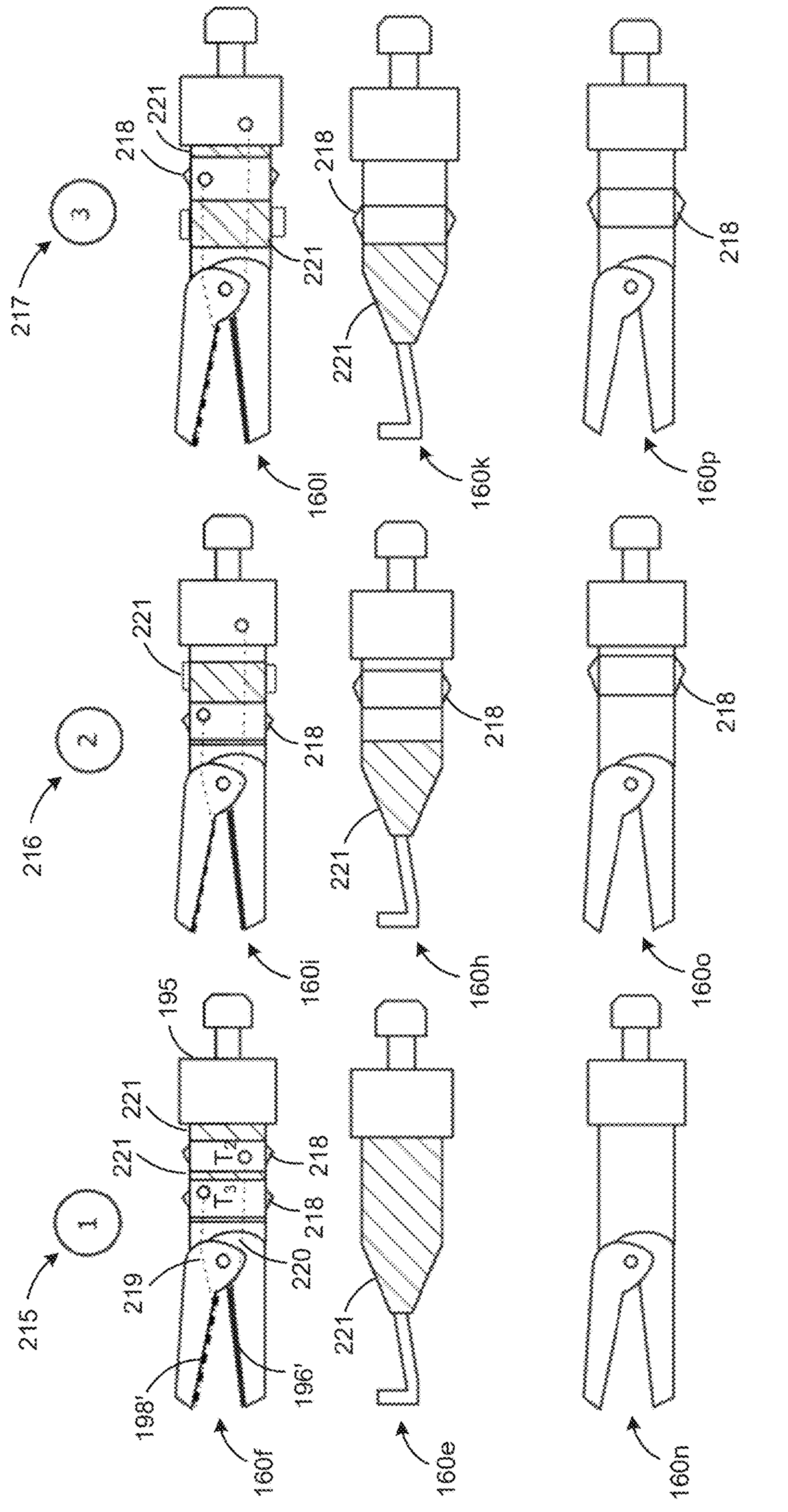
FIG. 19 illustrates additional exemplary interchangeable tool tips constructed in accordance with some embodiments.

Referring now to FIG. 19, additional exemplary interchangeable tool tips are provided. As shown in FIG. 19, the tool tips may be related to the first configuration 215, the second configuration 216, and/or the third configuration 217 as described above with regard to FIG. 18. For example, bipolar grasper 160*f* may be achieved in the second configuration 216 by a distinct connection to three cables comprised in the surgical device. For example, an electrical connection 219 may be present between second part 198' and second region $T_3$ of bipolar grasper 160*f*, and an electrical connection 220 may be present between first part 196' and first region $T_2$ of bipolar grasper 160*f*. One or more of said parts may be movable, for example, second part 198' may be movable. Further, bipolar grasper 160*f* is mounted to the distal portion of the elongated shaft of the surgical device, an electrical connection between second region $T_3$ and region $D_3$ may be present, and an electrical connection between first region $T_2$ and region $D_2$ may be present, wherein said connections may be achieved via spring contacts 218. Further, region $T_3$, region $T_2$, and tool end portion 195 may be electrically insulated via insulating elements 221.

Each of the exemplary interchangeable tool tips of FIG. 19 (e.g., tool tips 160*e*, 160*f*, 160*h*, 160*i*, 160*k*, 1601, and 160*n*-160*p*) may exhibit distinct connection to three cables comprised in the surgical device. Generally, electrical connection between regions of the tool tips, e.g., regions $T_2$, $T_3$, and regions of the distal portion of the elongated shaft, e.g., regions $D_2$, $D_3$, may further be achieved via spring contact rings 218 when the tool tip is mounted to the distal portion of the elongated shaft. As would be understood by a person having ordinary skill in the art, an electrical connection between tool end portion 195 of the respective tool tip and region $D_1$ may generally be present in most cases when the tool tip is mounted to the distal portion of the elongated shaft, unless insulating elements are used to prevent this. For example, in the case of the bipolar grasper 160*f*, insulation elements may be present so that no electrical connection between tool end portion 195 and region $D_1$ is present. Further, insulating elements 221 may be comprised in the distinct electrical connection.

For example, the tool tips may have insulating elements that may electrically insulate the operative portion of the tool tip, e.g., the moving parts of the tool tip, from one (bipolar), two (monopolar), or all three (no electrosurgical function) of the three cables that may be comprised in the surgical device. As described herein, the cables may be referred to as pole lines, and the operative portion of the tool tips, e.g., the moving parts of the tool tip, may be referred to as electrodes. Various electrode configurations may be possible, which would result in different insulation geometries at the tool tips. This may be illustrated, for example, by a bipolar grasper and/or a monopolar hook and/or a monopolar grasper. Moreover, if the tool tip is a hook, the tool tip may comprise an internal electrical connection between the terminal part of the hook and tool end portion.

As would be understood by a person having ordinary skill in the art, the distinct electrical connections, as exemplified in FIG. 19, but not described in detail for the sake of brevity, may allow for a variety of interchangeable tool tips. Accordingly, the ordinarily skilled person will understand how such distinct electrical connections may be achieved based on, for example, FIG. 19. A detailed description is given above in the case of the bipolar grasper **160*f* in the first configuration 215. Similarly, a bipolar grasper 160*i* may be achieved in the second configuration 216, and a bipolar grasper 160*l* may be achieved in the third configuration 217. As shown in FIG. 19, monopolar hooks 160*e*, 160*h*, and 160*k* may be achieved in the first, second, and third configurations 215, 216, 217, respectively. Further, monopolar graspers 160*n*, 1600, and 160*p* may be achieved in the first, second, and third configurations 215, 216, 217**, respectively.

Figure 20A:
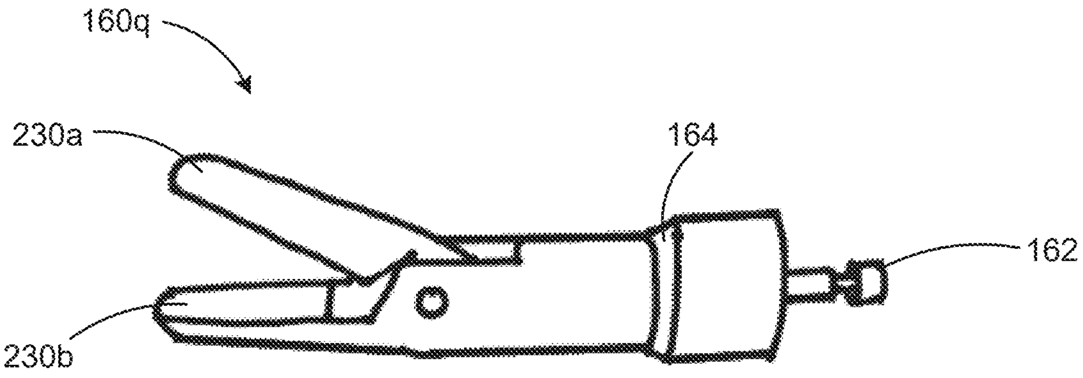
FIG. 20A illustrates an exemplary interchangeable needle driver tool tip.
Figure 20B:
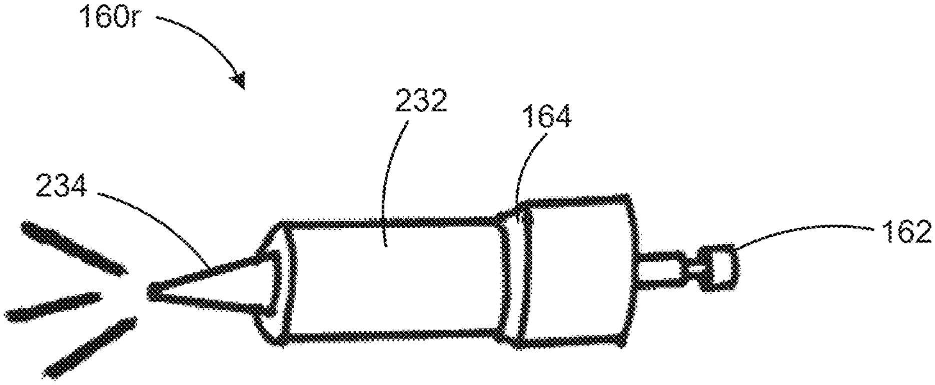
FIG. 20B illustrates an exemplary interchangeable tool tip for delivering a solution in accordance with some embodiments.

Referring now to FIGS. 20A and 20B, additional exemplary interchangeable tool tips configured to be utilized with the surgical devices described herein are provided. Accordingly, the interchangeable tool tips illustrated in FIGS. 20A and 20B may be removably stored within a corresponding chamber of the magazine of the surgical device, and may be selectively mounted at the distal end of the elongated shaft of the surgical device, as described above. FIG. 20A illustrates interchangeable needle driver tool tip **160*q* comprising jaws 230*a*, 230*b* configured to be actuated to hold a surgical needle for intra-operative sewing/suturing. The linkages of needle driver tool tip 160*q* may provide an over-center camming arrangement such that jaws 230*a*, 230*b* are not only closed, but is done so at a forced closure. As shown in FIG. 20A, interchangeable needle driver tool tip 160*q* may comprise proximal portion 164 having a corresponding geometry configured to mate with the tool rotating structure at the distal end of the elongated shaft in a manner such that rotary movement of needle driver tool tip 160*q* relative to the elongated shaft is inhibited when needle driver tool tip 160*q* is mounted thereto, and base 162** sized and shaped to be releasably coupled to the coupling element of the rod of the tool activation mechanism, as described above.

FIG. 20B illustrates interchangeable tool tip **160*r* configured to deliver a solution, e.g., a therapeutic agent such as flowable or fleece-based hemostats, in vivo at the surgical site. As shown in FIG. 20B, tool tip 160*r* similarly may comprise proximal portion 164 having a corresponding geometry configured to mate with the tool rotating structure at the distal end of the elongated shaft in a manner such that rotary movement of tool tip 160*r* relative to the elongated shaft is inhibited when tool tip 160*r* is mounted thereto, and base 162 sized and shaped to be releasably coupled to the coupling element of the rod of the tool activation mechanism, as described above. In addition, tool tip 160*r* further may comprise receptacle 232 configured to store a predetermined amount of solution therein, and nozzle 234 configured to dispense the solution from receptacle 232. For example, tool tip 160*r* may be a syringe-like device. Accordingly, linear translation of base 162 via the actuation rod, as described above, may cause a piston (not shown) of tool tip 160*r* to translate linearly within receptacle 232 to thereby dispense the solution via nozzle 234. In addition, the amount of solution dispensed from tool tip 160*r* may depend on the degree of actuation of the operative lever of the surgical device, e.g., operative lever 114, by the user, which causes a corresponding precise linear movement of the actuation rod and, accordingly, the piston of tool tip 160*r*, so that the desired amount of solution may be delivered to the surgical site. If less than all of the solution within receptacle 232 is dispensed therefrom, tool tip 160*r*** having the remaining solution therein may be returned to the magazine, and subsequently re-mounted to the distal end of the elongated shaft of the surgical device for subsequent use.

Figure 21A:
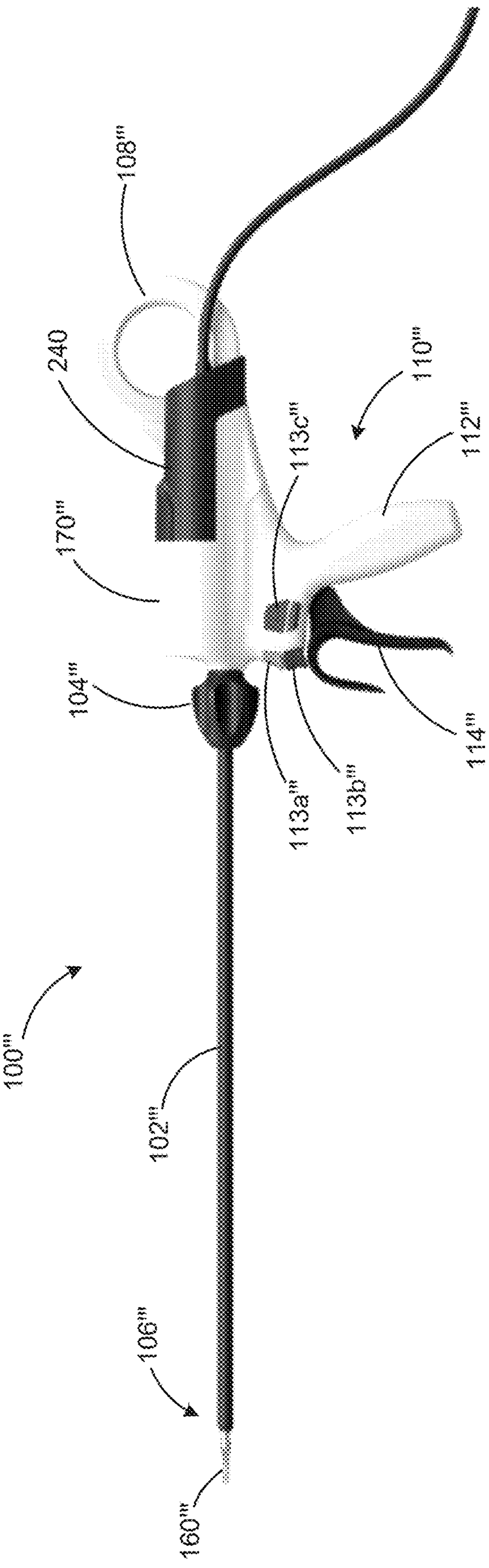
FIGS. 21A and 21B illustrates an alternative exemplary surgical device having a removable motor unit constructed in accordance with some embodiments.
Figure 21B:
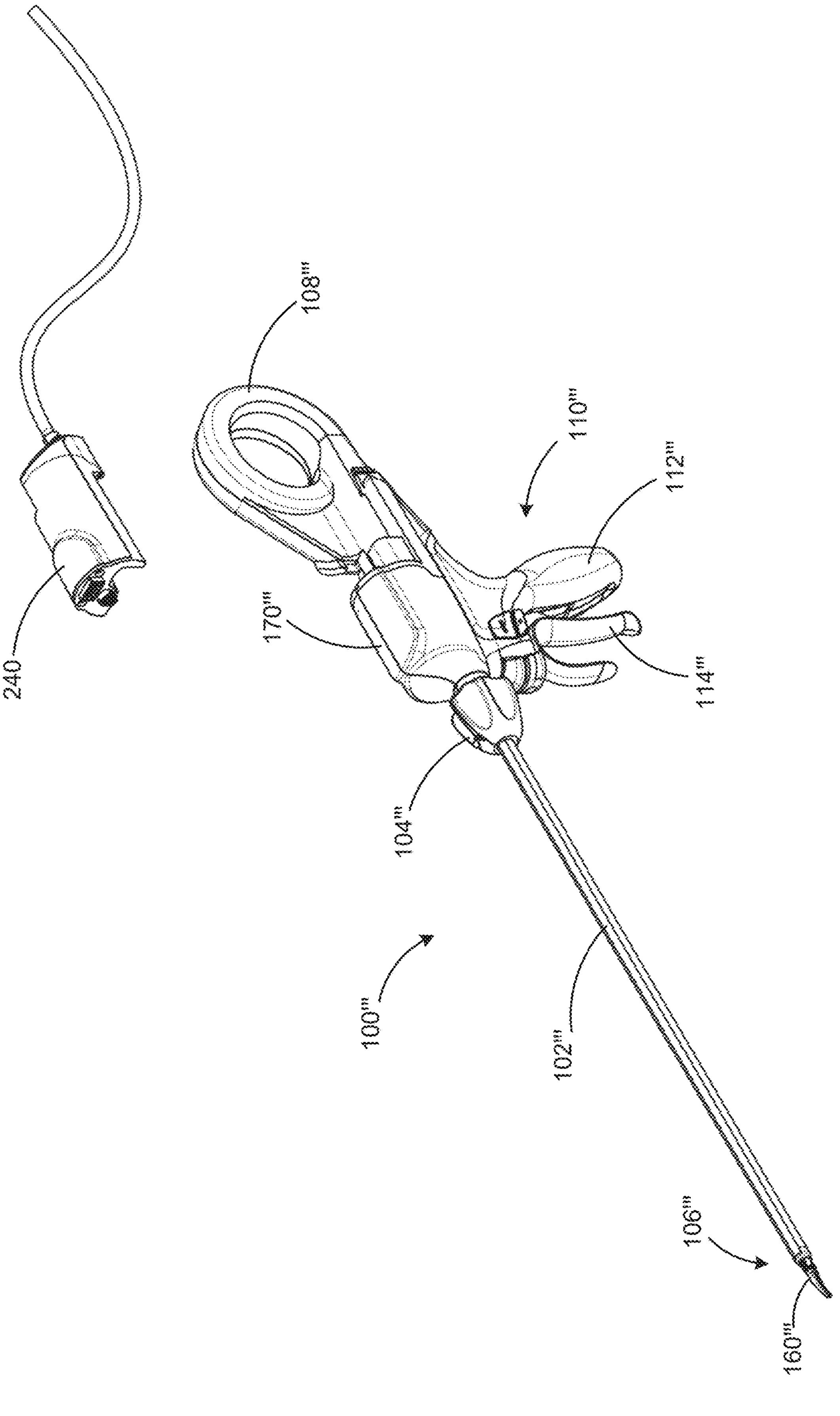

Referring now to FIGS. 21A and 21B, another alternative exemplary surgical device is provided. Surgical device 100''' may be constructed similar to surgical device 100, with similar components having like triple-prime reference numerals. For example, surgical device 100' may comprise elongated shaft 102''' having actuator 104''' and distal end 106''' configured to mount interchangeable tool tip 160''' thereto, and body portion 110''' having handle portion 112''', operative lever 114''', actuators **113*a*'''-113*c*''', magazine 170''', and receptacle 108''' for receiving a tool activation mechanism (not shown) in a retracted, rolled configuration, which correspond to elongated shaft 102 having actuator 104 and distal end 106 configured to mount interchangeable tool tip 160 thereto, and body portion 110 having handle portion 112, operative lever 114, actuators 113*a*-113*c*, magazine 170, and receptacle 108 of surgical device 100. Surgical device 100''' differs from surgical device 100 in that surgical device 100''' may comprise reusable motor unit 240 configured to be removeably coupled to body portion 110''' for actuating magazine 170'''** and the tool activation mechanism.

For example, motor unit 240 may comprise one or more motors configured to be actuated to move magazine 170''' relative to body portion 110''', e.g., to align the selected chamber with the proximal end of elongated shaft 102''' based on the user input, and one or more motors configured to be actuated to drive actuation of the tool activation mechanism, as described above. As described above, a first motor may be configured to drive actuation of magazine 170''', and a separate second motor may be configured to drive actuation of the tool activation mechanism. Preferably, surgical device 100''' may two separate components, a reusable component (e.g., motor unit 240) and a single-use component (e.g., body portion 110''', elongated shaft 102''', magazine 170''', interchangeable tool tip 160''', etc.). Accordingly, magazine 170''' may be permanently integrated with body portion 110'''. As shown in FIGS. 21A and 21B, motor unit 240 may comprise a cable for electrical connection with, e.g., controller 12 and, accordingly, a power generator coupled thereto, to thereby provide electrosurgical power to the electrical components of surgical device 100'''.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A method for performing a surgical procedure, the method comprising:

positioning a first tool tip of a plurality of interchangeable tool tips at a distal end of an elongated shaft of a surgical device for performing a first type of surgical task, the first tool tip releasably coupled to a distal region of a tool activation mechanism;

receiving, via a user interface, user input indicative of a second tool tip of the plurality of interchangeable tool tips for performing a second type of surgical task, the second tool tip disposed within a magazine comprising a plurality of chambers and positioned at a proximal end of the elongated shaft;

retracting the first tool tip into a first chamber of the plurality of chambers using the tool activation mechanism;

selectively actuating, via at least one motor operatively coupled to the magazine, the magazine to align a second chamber of the plurality of chambers with the proximal end of the elongated shaft based on the user input, the second chamber having the second tool tip therein; and transitioning the tool activation mechanism between a retracted configuration where the distal region of the tool activation mechanism is disposed proximal to the second chamber and an extended configuration where the distal region is releasably coupled to the second tool tip and advanced such that the second tool tip is mounted at the distal end of the elongated shaft for performing the second type of surgical task.

2. The method of claim 1, wherein the surgical device comprises a body portion coupled to the proximal end of the elongated shaft, and wherein the magazine is coupled to the body portion.

3. The method of claim 2, wherein the plurality of chambers are equally radially disposed about a longitudinal axis of the magazine, and wherein selectively actuating the magazine comprises rotating the magazine relative to the body portion about the longitudinal axis.

4. The method of claim 2, wherein transitioning the tool activation mechanism to the retracted configuration comprises receiving the tool activation mechanism within a receptacle of the body portion.

5. The method of claim 4, wherein receiving the tool activation mechanism within the receptacle of the body portion comprises substantially bending the tool activation mechanism about a bend axis, the bend axis substantially orthogonal to a longitudinal axis of the elongated shaft.

6. The method of claim 2, further comprising:

actuating an actuator to rotate the elongated shaft and the second tool tip mounted thereon relative to the body portion, wherein the distal end of the elongated shaft is configured to prevent rotation of the second tool tip relative to the elongated shaft.

7. The method of claim 6, wherein the actuator comprises a rotatable knob disposed on the body portion, and wherein actuating the actuator comprises rotating the knob to rotate the elongated shaft and the second tool tip mounted thereon relative to the body portion.

8. The method of claim 1, wherein the tool activation mechanism is substantially rigid against compression and elongation and flexible against bending as the tool activation mechanism transitions between retracted the configuration and the extended configuration.

9. The method of claim 1, wherein selectively actuating the magazine comprises selectively actuating the magazine via a first motor of the at least one motor, and wherein transitioning the tool activation mechanism between the retracted configuration and the extended configuration comprises actuating the tool activation mechanism via a second motor of the at least one motor.

10. The method of claim 1, wherein the tool activation mechanism comprises a rack and an actuation rod disposed within a lumen of the rack, and wherein transitioning the tool activation mechanism between the retracted configuration and the extended configuration comprises moving the rack and the actuation rod together.

11. The method of claim 10, wherein the rack comprises a plurality of joint-connected rack elements.

12. The method of claim 10, wherein releasably coupling the distal region of the tool activation mechanism to the second tool tip comprises releasably engaging a distal end of the rack with a proximal portion of the second tool tip and releasably coupling a coupling element at a distal end of the actuation rod to an engagement portion of the second tool tip.

13. The method of claim 12, further comprising moving the actuation rod axially relative to the rack when the coupling element is coupled to the engagement portion to thereby actuate the second tool tip.

14. The method of claim 13, wherein moving the actuation rod axially relative to the rack comprises actuating, in the extended configuration, an actuation bar releasably coupled to a proximal coupling element of the actuation rod.

15. The method of claim 14, wherein actuating the actuation bar comprises actuating an interface of the surgical device to move the actuation rod axially relative to the rack.

16. The method of claim 10, wherein moving the rack comprises substantially bending the rack about a single bend axis.

17. The method of claim 10, wherein moving the rack comprises actuating a worm gear to cause rotation of a pinion gear operatively coupled to a geared outer surface of the rack to thereby cause translational movement of the rack via a geared connection between the pinion gear and the geared outer surface.

18. The method of claim 1, wherein transitioning the tool activation mechanism between the retracted configuration and the extended configuration comprises advancing the tool activation mechanism through a lumen of the elongated shaft.

19. The method of claim 1, wherein transitioning the tool activation mechanism between the retracted configuration and the extended configuration to retract the first tool tip into the first chamber and to mount the second tool tip at the distal end of the elongated shaft occurs while the distal end of the elongated shaft remains inserted in a patient via a trocar port.

20. The method of claim 1, further comprising:

receiving the plurality of interchangeable tool tips within the plurality of chambers of the magazine, wherein proximal movement of the plurality of interchangeable tool tips is prevented beyond a proximal end of the plurality of chambers.

21. The method of claim 1, further comprising receiving the plurality of interchangeable tool tips within the plurality of chambers of the magazine in a predetermined aligned manner.

22. The method of claim 21, wherein the predetermined aligned manner prevents rotation of the plurality of interchangeable tool tips relative to the plurality of chambers.

23. The method of claim 1, further comprising actuating, when the first tool tip of the plurality of interchangeable tool tips is mounted at the distal end of the elongated shaft, the first tool tip in an open and close degree of freedom.

24. The method of claim 1, further comprising transmitting, when the first tool tip of the plurality of interchangeable tool tips is mounted at the distal end of the elongated shaft, electric power from a generator to the first tool tip.

25. The method of claim 24, further comprising performing electric cauterization via the first tool tip.

26. The method of claim 1, wherein the surgical device comprises a handle at the proximal end of the elongated shaft, the handle configured to be held by a user for performing surgery.

27. The method of claim 1, further comprising using the surgical device with a surgical robot system for performing robot-assisted surgery.

28. The method of claim 1, further comprising:
displaying, via a display, the plurality of interchangeable tool tips within the plurality of chambers,
wherein the display displays a selection of the plurality of interchangeable tool tips based on the user input.

29. The method of claim 28, wherein displaying the plurality of interchangeable tool tips within the plurality of chambers comprises displaying, via the display, a hook, a grasper, and scissors.

30. The method of claim 1, wherein the first tool tip comprises a hook or a grasper and the second tool tip comprises scissors.

* * * * *